US009873113B2

(12) United States Patent
Schmidt et al.

(10) Patent No.: US 9,873,113 B2
(45) Date of Patent: Jan. 23, 2018

(54) METHODS FOR PRODUCING CRYSTALLINE MICROPOROUS SOLIDS WITH A NEW CIT-7 TOPOLOGY AND COMPOSITIONS DERIVED FROM THE SAME

(71) Applicant: California Institute of Technology, Pasadena, CA (US)

(72) Inventors: Joel E. Schmidt, Pasadena, CA (US); Mark E. Davis, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 127 days.

(21) Appl. No.: 14/602,433

(22) Filed: Jan. 22, 2015

(65) Prior Publication Data

US 2015/0203357 A1   Jul. 23, 2015

Related U.S. Application Data

(60) Provisional application No. 61/930,326, filed on Jan. 22, 2014, provisional application No. 61/969,963, (Continued)

(51) Int. Cl.
*C01B 39/48* (2006.01)
*B01J 29/70* (2006.01)
(Continued)

(52) U.S. Cl.
CPC ............. *B01J 29/70* (2013.01); *B01D 53/02* (2013.01); *B01J 29/035* (2013.01); *B01J 29/041* (2013.01);
(Continued)

(58) Field of Classification Search
None
See application file for complete search history.

(56) References Cited

U.S. PATENT DOCUMENTS 3,140,249 A   7/1964   Plank et al.
3,140,251 A   7/1964   Plank et al.
(Continued)

FOREIGN PATENT DOCUMENTS

| WO | WO/1999/008961 | 2/1999 |
| WO | WO 2006/033470 A2 | 3/2006 |
| WO | WO 2010/118377 A2 | 10/2010 |

OTHER PUBLICATIONS

Zones et al. "Diquaternary structure-directing agents built upon charged imidazolium ring centers and their use in synthesis of one-dimensional pore zeolites", published as an Advance Article on the web Aug. 17, 2005. Journal of Materials Chemistry, copyright to The Royal Society of Chemistry in 2005, 15, pp. 4215-4223.*

(Continued)

*Primary Examiner* — Katie L Hammer
(74) *Attorney, Agent, or Firm* — Baker & Hostetler LLP

(57) ABSTRACT

This disclosure relates to new crystalline microporous solids (including silicate- and aluminosilicate-based solids), the compositions comprising 8 and 10 membered inorganic rings, particularly those having CIT-7 topologies having a range of Si:Al ratios, methods of preparing these and known crystalline microporous solids using certain quaternized imidazolium cation structuring agents.

39 Claims, 23 Drawing Sheets

Related U.S. Application Data filed on Mar. 25, 2014, provisional application No. 62/054,247, filed on Sep. 23, 2014, provisional application No. 62/013,167, filed on Jun. 17, 2014, provisional application No. 62/077,719, filed on Nov. 10, 2014.

(51) Int. Cl.

| | | |
|---|---|---|
| C01B 39/08 | (2006.01) | |
| C01B 39/06 | (2006.01) | |
| B01J 29/068 | (2006.01) | |
| C01B 39/12 | (2006.01) | |
| B01J 29/064 | (2006.01) | |
| B01J 29/06 | (2006.01) | |
| B01J 29/86 | (2006.01) | |
| B01J 29/89 | (2006.01) | |
| B01J 29/072 | (2006.01) | |
| B01J 29/87 | (2006.01) | |
| B01J 29/88 | (2006.01) | |
| B01J 29/04 | (2006.01) | |
| B01J 37/08 | (2006.01) | |
| C01B 39/00 | (2006.01) | |
| C07C 1/20 | (2006.01) | |
| B01D 53/02 | (2006.01) | |
| C07C 2/00 | (2006.01) | |
| C07C 2/12 | (2006.01) | |
| C07C 5/25 | (2006.01) | |
| C07C 5/27 | (2006.01) | |
| C07C 6/06 | (2006.01) | |
| C07C 7/13 | (2006.01) | |
| C07C 209/14 | (2006.01) | |
| C10G 11/05 | (2006.01) | |
| C10G 35/00 | (2006.01) | |
| C10G 47/04 | (2006.01) | |
| C07C 209/16 | (2006.01) | |
| C10G 29/20 | (2006.01) | |
| C10G 35/06 | (2006.01) | |
| C10G 47/16 | (2006.01) | |
| C10G 49/08 | (2006.01) | |
| C10G 50/00 | (2006.01) | |
| B01J 29/035 | (2006.01) | |
| C07C 67/37 | (2006.01) | |
| B01J 29/85 | (2006.01) | |

(52) U.S. Cl.
CPC ........... *B01J 29/061* (2013.01); *B01J 29/064* (2013.01); *B01J 29/068* (2013.01); *B01J 29/072* (2013.01); *B01J 29/86* (2013.01); *B01J 29/87* (2013.01); *B01J 29/88* (2013.01); *B01J 29/89* (2013.01); *B01J 37/08* (2013.01); *B01J 37/082* (2013.01); *C01B 39/00* (2013.01); *C01B 39/06* (2013.01); *C01B 39/065* (2013.01); *C01B 39/08* (2013.01); *C01B 39/082* (2013.01); *C01B 39/085* (2013.01); *C01B 39/087* (2013.01); *C01B 39/12* (2013.01); *C01B 39/48* (2013.01); *C07C 1/20* (2013.01); *C07C 2/00* (2013.01); *C07C 2/12* (2013.01); *C07C 5/2518* (2013.01); *C07C 5/2737* (2013.01); *C07C 5/2775* (2013.01); *C07C 6/06* (2013.01); *C07C 7/13* (2013.01); *C07C 209/14* (2013.01); *C07C 209/16* (2013.01); *C10G 11/05* (2013.01); *C10G 29/205* (2013.01); *C10G 35/00* (2013.01); *C10G 35/065* (2013.01); *C10G 47/04* (2013.01); *C10G 47/16* (2013.01); *C10G 49/08* (2013.01); *C10G 50/00* (2013.01); *B01D 2253/106* (2013.01); *B01D 2253/108* (2013.01); *B01D 2253/1085* (2013.01); *B01D 2253/1124* (2013.01); *B01D 2253/20* (2013.01); *B01D 2256/12* (2013.01); *B01D 2257/102* (2013.01); *B01D 2257/404* (2013.01); *B01J 29/7015* (2013.01); *B01J 29/85* (2013.01); *C07C 67/37* (2013.01); *C07C 2529/70* (2013.01); *Y02P 30/42* (2015.11)

(56) References Cited

U.S. PATENT DOCUMENTS

| | | |
|---|---|---|
| 3,140,253 A | 7/1964 | Plank et al. |
| 3,565,788 A | 2/1971 | Foucher et al. |
| 4,016,245 A | 4/1977 | Plank et al. |
| 4,483,835 A | 11/1984 | Zones |
| 4,503,023 A | 3/1985 | Breck |
| 4,503,024 A | 3/1985 | Bourgogne et al. |
| 4,873,067 A | 10/1989 | Valyocsik et al. |
| 4,910,006 A | 3/1990 | Zones et al. |
| 4,925,548 A | 5/1990 | Rubin |
| 5,316,753 A | 5/1994 | Nakagawa |
| 5,614,166 A | 3/1997 | Gies et al. |
| 6,605,267 B1 | 8/2003 | Lee |
| 6,676,732 B2 | 1/2004 | Lee et al. |
| 6,960,327 B2 | 11/2005 | Navrotsky et al. |
| 7,138,099 B1 | 11/2006 | Zones et al. |
| 7,527,782 B2 | 5/2009 | Corma et al. |
| 7,713,512 B2 | 5/2010 | Zones et al. |
| 2003/0206844 A1 | 11/2003 | Lee et al. |
| 2006/0110321 A1 | 5/2006 | Corma et al. |
| 2008/0118431 A1* | 5/2008 | Vermeiren ............ C01B 37/005 423/713 |
| 2009/0005600 A1 | 1/2009 | Bosch et al. |
| 2009/0299121 A1* | 12/2009 | Corma ..................... B01J 29/04 585/830 |
| 2010/0119736 A1* | 5/2010 | Yan ......................... C01B 39/36 427/595 |
| 2010/0260665 A1* | 10/2010 | Archer .................. C01B 37/007 423/706 |
| 2010/0305335 A1 | 12/2010 | Palmer et al. |
| 2012/0178615 A1* | 7/2012 | Corma ................ B01J 29/7042 502/64 |
| 2013/0052125 A1* | 2/2013 | Moini ..................... C01B 39/48 423/700 |
| 2015/0202603 A1 | 7/2015 | Schmidt |
| 2015/0202612 A1 | 7/2015 | Schmidt |
| 2015/0203357 A1 | 7/2015 | Schmidt |
| 2015/0203358 A1 | 7/2015 | Schmidt |

OTHER PUBLICATIONS

Accardo, et al., "Peptide-based Targeting Strategies for Simultaneous Imaging and Therapy with Nanovectors" Polymer J., May 2013, 45, 481-93.

Agadjanian et al, "Specific Delivery of Corroles to Cells via Noncovalent Conjugates with Viral Proteins", Pharmaceutical Research, Feb. 2006, 23(2), 367-377.

Aina, et al., "Therapeutic Cancer Targeting Peptides", Biopolymers, Oct. 2002, 66(3), 184-99.

Allen, "Ligand-Targeted Therapeutics in Anticancer Therapy", Nature Rev. Cancer, Oct. 2, 2002, 2(10), 750-63.

Almadhoun et al, "Nanocomposites of Ferroelectric Polymers With Surface-Hydroxylated BaTiO3 Nanoparticles for Energy Storage Applications", Chem., May 2012, 22, 11196.

Arkles, "Silane Coupling Agents Connecting Across Boundaries", 2006, Version 2.0, 60 pages.

Autret et al, "Synthesis and Electrochemistry of Iron (111) Corroles Containing a Nitrosyl Axial Ligand. Spectral Characterization of [(OEC)FeTlI(NO)]nW here n=0, 1, 2, or −1 and OEC Is the Trianion of 2,3,7,8,12,13,17,18-Octaethylcorrol", J. Am. Chem. Soc., 1994, vol. 116, 9141-9149.

(56) References Cited

OTHER PUBLICATIONS

Aviv et al, "Corrole-Based Applications", Chemical Communications, May 28, 2007, 1987-1999.
Baerlocher, et al., "Charge Flipping Combined with Histogram Matching to Solve Complex Crystal Structures from Powder Diffraction Data", 2007, 222, 47-53.
Barata et al., "Corrole-Silica Hybrid Particles: Synthesis and Effects on Singlet Oxygen Generation", RSC Adv., Oct. 24, 2012, vol. 3, 274-80.
Barbe et al, "Metallocorroles as Sensing Components for Gas Sensors: Remarkable Affinity and Selectivity of Cobalt(III) Corroles for CO vs. O2 and N2", The Royal Society of Chemistry, Mar. 23, 2004, 1208-1214.
Basabe, et al., "Locattion of Extra-Framework Co2, Ni2, Cu2, and Zn2 Cations in Natural and Dealuminated Clinoptilolite", Micro and Meso Materials, 2012, vol. 155, 233-239.
Blumenfeld et al, "Decorating Metal Oxide Surfaces with Fluorescent Chlorosulfonated Corroles", Inorganic Chemistry, Apr. 2013, vol. 52, 4774-4776.
Bravo-Suarez, et al., "Design of Heterogeneous Catalysts for Fuels and Chemicals Processing: An Overview", Ameri Chem. Society, 2013, Chapter 1, 1-66.
Burton, et al., "Organic Molecules in Zeolite Synthesis: Their Preparation and Structure-Directing Effects", Zeolite Science and Practice, 2007, vol. 3, 137-179.
Camblor, M.A. et al. "Synthesis of all-silica and high-silica molecular sieves in fluoride media" Topics in Catalysis, 1999, vol. 9, 59-76.
Corma, "State of the Art and Future Challenges of Zeolites as Catalysts", Journal of Catalysis, 2003, vol. 216, 298-312.
Corma, et al., "Zeolites and Catalysis" Wiley-VCH Verlag GmbH & Co., Czech Republic, 2010, 911 pgs.
Davis, M.E., "Ordered porous materials for emerging applications" Nature 417, 2002, 813-821.
Degnan, "Applications of Zeolites in Petroleum Refining", Topics in Catalysis, 2000, vol. 13, 349-356.
Dorset, et al., "P-Derived Organic Cations as Structure-Directing Agents: Synthesis of High-Silica Zeolite (ITQ-27) with a Two-Dimensional 12-Ring Channel System", J. Am. Chem. Soc., Jun. 16, 2006, vol. 128, 8862-8867.
Framework Type STW. Available from: www.iza-structure.org/databases, retrieved Oct. 16, 2014.
Grosse-Kunstleve, et al., "Powder Diffraction Data and Crystal Chemical Information Combined in an Automated Structure Determination Procedure for Zeolites", J. Appl. Crystallogr., 1997, 30, 985-995.
Haber et al, "Protecting the Beneficial Functionality of Lipoproteins by 1-fe, A Corrole-Based Catalytic Antioxidant", Chem. Sci., 2011, vol. 2, 295-302.
Hathaway, P.E. et al. "High resolution, quasi-equilibrium sorption studies of molecular sieves" Catalysis Letters, 1990, vol. 5, 333-347.
Hong, et al., "Synthesis Structure Solution, Characterization, and Catalytic Properties of TNU-10: A High-Silica Zeolite with the STI Topology", J. Am. Chem. Soc., 2004, 126, 5817-26.
Hori, T. and Osuka, A., "Nucleophilic Substitution Reactions of meso-5,10,15-Tris(pentafluorophenyl)-Corrole; Synthesis of ABC-Type Corroles and Corrole-Based Organogels", Eur. J. Org. Chem., 2010, 2379-2386.
Hwang et al, "Photoexcitation of Tumor-Targeted Corroles Induces Singlet Oxygen-Mediated Augmentation of Cytotoxicity", Journal of Controlled Release, 2012, vol. 163, 368-373.
Ikeda, et al., "Lateral Distribution of N3 Dye Molecules on TiO2 (110) Surface", Journal of Photochemistry, 2009, vol. 202, 185-190.
Jackowski, et al., "DiquaternaryAmmoniumCompounds in Zeolite Synthesis: Cyclic and Polycyclic N-Heterocycles Connected by Methylene Chains", J. Am. Chem. Soc. Jan. 7, 2009, 131, 1092-100.
Jaracz, et al., "Recent Advances in Tumor-Targeting Anticancer Drug Conjugates" Bioorg. Med. Chem., Dec. 2005, vol. 13(17), 5043-54.
Jin, et al., "Targeted Delivery System of Nanobiomaterials in Anticancer Therapy from Cells to Clinics", BioMed. Res. Inti., Feb. 2014, 24 pages.
Kanamoril et al, "Neuroprotection Against Superoxide Anion Radical by Metallocorroles in Cellular and Murine Models of Optic Neuropathy", Journal of Neurochemistry, 2010, vol. 114, 488-498.
Kim, et al., "A Case Study of Divergent Structure Directing Effects of Geometric Isomers The Discovery of a New Structure Directing Agent for an All-Silica RTH Zeolite Prepared in Fluoride Media", Microporous and Mesoporous Materials, Apr. 11, 2008, vol. 116, 227-32.
Kubota, et al., "Properties of Organic Cations that Lead to the Structure-Direction of High-Silica Molecular Sieves", Microporous Materials, 1996, vol. 6, 213-229.
Lee, et al., "Polymethylated Octanes Leading to Zeolote SSZ-50", Journ. of Solid State Chem., Mar. 1, 2002, vol. 167, 289-98.
Lee, et al., "Synthesis of Zeolite ZSM-57 and it's Catalytic Evaluation for the 1-Butene Skeletal Isomerization and N-Octane Cracking", J. Catal., 2000, 196, 158-166.
Li, et al., "Metal Exchanged Ferrierites as Catalysts for the Selective Reduction of NO with Methane", Appl. Catal B Environ.,1993, 3, L1-L11.
Lin, L.C., et al., "In Silico screening of carbon-capture materials" Nature Materials, 2012, vol. 11, 633-641.
Liu, et al., Differences in AL Distribution and Acidic Properties Between RTH-Type Zeolites Synthesized with OSDAs and without OSDAs, Nov. 8, 2014, vol. 16, 4155-64.
Mahammed et al, "Highly Selective Chlorosulfonation of Tris(Pentafluorophenyl) Corrole as a Synthetic Tool for the Preparation of Amphiphilic Corroles and Metal Complexes of Planar Chirality", Organic Letters, Nov. 1, 2001, vol. 3(22), 3443-3436.
Martens, et al., "Tailored Alkene Oligomerization with H-ZSM-57 Zeolite", Angew Chemie. 2000, 39(23), 4376-4379.
Martinez, et al., "Inorganic Molecular Sieves: Preparation, Modification and Industrial Application in Catalytic Processes" Chem. Reviews, Mar. 2011, vol. 255, 1558-1580.
Meng, et al., "Green Routes for Synthesis of Zeolites", Chemical Reviews, 2014, vol. 114, 1521-43.
Moliner, et al. "Towards the rational design of efficient organic structure—No directing agents for zeolite synthesis" Angew Chern tnt Ed Eng, 2013, 52, 13880-13889.
Nakagawa, et al. "Guest/host Relationships in Zeolite Synthesis: Ring-Substituted Piperidines and the Remarkable Adamantane Mimicry by 1-azonio spiro [5.5] Undecanes" Microporous and Mesoporous Materials, 1998, vol. 22, 69-85.
Okun et al, "Manganese Corroles Prevent Intracellular Nitration and Subsequent Death of Insulin-Producing Cells", ACS Chemical Biology, Aug. 28, 2009, vol. 4(11), 910-914.
Palatinus, et al., "SUPERFLIP—A Computer Program for the Solution of Crystal Structures by Charge Flipping in Arbitrary Dimensions", J. Appl. Cryst., Aug. 2007,40(4), 786-790.
Palmer, "Transition Metal Corrole Coordination Chemistry", Struct. Bond, Sep. 14, 2011, vol. 142, 49-90.
Pophale, et al. "Computational Prediction of Chemically Synthesizable Organic No structure Directing Agents for Zeolites" Journal of Materials Chemistry A, Apr. 26, 2013, 6750-6760.
Pophale, et al., "A Database of New Zeolite-Like Materials" Phys. Chem. Phys., Jul. 21, 2011, vol. 13, 12407-12412.
Robson, "Verified Synthesis of Zeolitic Materials", Elsevier, Netherlans, 2001.
Rojas, et al., "Synthesis, Structure, and Optical Activity of HPM-1, 34-36 a Pure Silica Chiral Zeolite", Journal of the American Chemical Society, Jul. 18, 2013, vol. 135(32), pp. 11975-11984.
Roman-Leshkov, et al., "Impact of Controlling the Site Distribution of Al Atoms on Catalytic Properties in Ferrierite-Type Zeolites", J. Chem. C., 2011, 115 1096-1102.
Rossini, "The Impact of Catalytic Materials on Fuel Reformation", Elsevier, 2003, vol. 77, 467-484.
Saltsman et al, "Selective Substitution of Corroles: Nitration, Hydroformylation, and Chlorosulfonation", J. Am. Chem. Soc. Jun. 26, 2002, 124(25):7411-20.

(56) References Cited

OTHER PUBLICATIONS

Sapsford, et al., "Functionalizing Nanoparticles with Biological Molecules: Developing Chemistires that Facilitate Nanotechnology", American Chemical Society, Feb. 22, 2013, pp. 1904-2074.
Schmidt, et al., "Synthesis of a Specified, Silica Molecular Sieve 1-3,22-27,34-36 by Using Computationally Predicted Organic Structure-Directing Agents", Angewandte Chemic, Jun. 24, 2014, vol. 126(32), 8512-8514.
Schmidt, et al., "Facile Preparation of Aluminosilicate RTH Across a Wide Composition Rabge Using a New Organic Structure-Directing Agent", Chem. of Materials, Nov. 18, 2014, 7 pgs.
Schreyeck, et al., "PREFER: A New Layered (Alumino) Silicate Precursor of FER-Type Zeolite", Microporous Matter, 1996, 6, 259-71.
Simkhovich et al, "Mono- and Binuclear Ruthenium Corroles: Synthesis, Spectroscopy, Electrochemistry, and Structural Characterization", Chem. Eur. J. 2003, vol. 9(1), 201-208.
Simkhovich et al, "Synthesis and Characterization of Germanium, Tin, Phosphorus, Iron, and Rhodium Complexes of Tris(pentafluorophenyl) Corrole, and the Utilization of the Iron and Rhodium Corroles as Cyclopropanation Catalysts", Chem. Eur. J., 2001, vol. 7(5), 1041-1055.
Smeets, et al., "SSZ-45: A High-Silica Zeolite with Small Pore Openings, Large Cavities and Unusual Adsorption Properties", Chem. Mater, May 30, 2014, 12 pgs.
Tamura, et al, "Mechanism of Hydroxylation of Metal Oxide Surfaces", Journal of Colloid and Interface Sci., Nov. 2001, vol. 243(1), 202-207.
Tang, L., et al., "A Zeolite Family with Chiral and Achiral Structures Built from the Same Building Layer" Nature Materials, 2008, vol. 7, 381-385.
Tijsebaert, et al., "Shape-Selective Synthesis of Methylamines Over the RRO Zeolite Al-RUB-41", J. Catal., 2011, 278, 246-252.
Toby, "CMPR—A Powder Diffraction Toolkit", Appl. Cryst., Aug. 13, 2005, 38, 1040-1041.
Tortora et al, "Supramolecular Sensing Mechanism of Corrole Thin Films", Sensors and Actuartors B, 2013, vol. 187, 72-77.
Vermeiren, et al., "Impact of Zeolites on the Petroleum and Petrochemical Industry", Top Catal., May 15, 2009, vol. 52, 1131-1161.
Vidavsky, et al., "Light-Induced Olefin Metathesis", J. Org. Chem, Nov. 23, 2010, vol. 6, 1106-19.
Viskota, et al., "Surface Functionalization of Barium Titanate SHG Nanoprobes for In Vivo Imaging in Zebrafish", Protocol, vol. 7(9), Aug. 9, 2012, pp. 1618-1633.
Vortmann, et al., "Synthesis and Crystal Structure of the New Borosilicate Zeolite RUB-13", Microporous Materials, 1995, vol. 4, 111-21.
Wagner et al., Guest/Host Relationships in the Synthesis of the Novel Cage-Based Zeolites SSZ-35, SSZ-36, and SSZ-39, J. Am. Chem. Soc., 2000, 122, 263-73.
Wan, et al., "Three-Dimensional Rotation Electron Diffraction: Software RED for Automated Data Collection and Date Processing" J. Appl. Cryst., Dec. 2013, 46, 1863-1873.

Wang, et al., "Characteristics of High Efficiency Dye-Sensitized Solar Cells." Journal of Physical Chemistry B, vol. 110, 2006, pp. 25210-25221.
Wang, et al., "Synthesis and Crystal Structure of Zeolite RUB-41 Obtained as Calcination Product of a Layers Precursor: A Systematic Approach to a New Synthesis Route", Chem. Matter, 17, 2005, 43-49.
Weaver. "Corrales." PhD Thesis—California Institute of Technology, May 5, 2005. pp. i-xvi and 1-116.
Werner, et al., "TREOR, A Semi-Exhaustive Trial- and Error Powder Indexing Program for all Symmetries", J. Appl. Cryst., Oct. 1985, 18, 367-370.
Yilmaz, et al., "Al-RUB-41: A Shape-Selective Zeolite Catalyst froma Layered Silicate" Chem. Commun., 47, Nov. 22, 2011, 1812-4.
Yilmaz, et al., "Catalytic Applications of Zeolites in Chemical Industry", Top Catal, 2009, vol. 52, 888-895.
Yokoi, et al., "Diversification of RTH-Type Zeolite and it's Catalytic Application", Angew Chem., 2009, vol. 48, 9884-87.
Yoshioka, et al., "Preperation of RTH-Type Zeolites with the Amount and/or Kind of Organic Structure-Directing Agents (OSDA): Are OSDA'S Indispensable for the Crystallization?", Microporous and Mesoporous Materials, 2012, vol. 153, 70-78.
Zeolyst, "New Perspectives and Challenges for the Zeolite Industry", Annual Meeting in Seoul, Aug. 29, 2013, 24 pgs.
Zhang, et al., "Collecting 3D Electron Diffraction Data by the Rotation Method", 2010, 225, 94-102.
Zhao, et al., "Characteristics of the Synthetic Heulandite-Clinoptilolite Family of Zeolites", Micro and Meso Materials, Feb. 4, 1998, vol. 21, 371-379.
Zones, et al. "Translating new materials discoveries in zeolite research to commercial manufacture" Microporous and Mesoporous Materials, 2011, vol. 144, 1-8.
Zones, et al., "Searching for New High Silica Zeolites Through a Synergy of Organic Templates and Novel Inorganic Conditions", Micro and Meso Materials, 1998, vol. 21, 199-211.
Zones, et al., "Strategies in Developing Routes to Commercialization of Novel High Silica Zeolites", Studies in Surface Science and Catalysis, 2005, vol. 158, 10 pgs.
Zones, et al., "Synthesis of High Silica Zeolites Using a Mixed Quaternary Anunonium Cation, Amine Approach: Discovery of Zealite SSZ-47", Chemistry of Materials, 2002, vol. 14(1), 313-320.
Clinoptilolite XRD Table, "Powder Pattern for Clinoptilolite (HEU)", Mar. 15, 2017, http://europe.iza-structure.org/IZA-SC/xrd_plot.php, 46 pages.
Jacobs et al., "Preparation and Properties of Hydrogen Form of Stilbite, Heulandite and Clinoptilolite Zeolites", J. Chem. Soc., Faraday Trans. 1, 1979, 883-891.
Koyama et al., "Clinoptilolite: the distribution of potassium atoms and its role in thermal stability", Zeitschrift für Kristallographie, Bd., 1977, 145, S., 216-239.
Lee et al., "Dealumination of Sodium Y Zeolite with Hydrochloric Acid", J. Chem. Soc., Faraday Trans. 1, 1987, 83, 1531-1537.

* cited by examiner

FIG. 4B-C
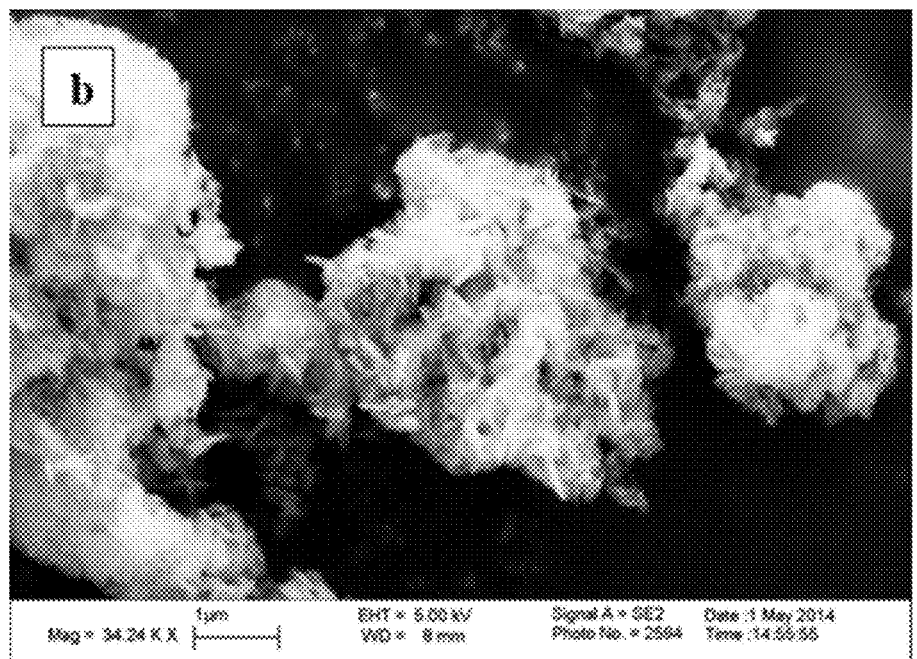
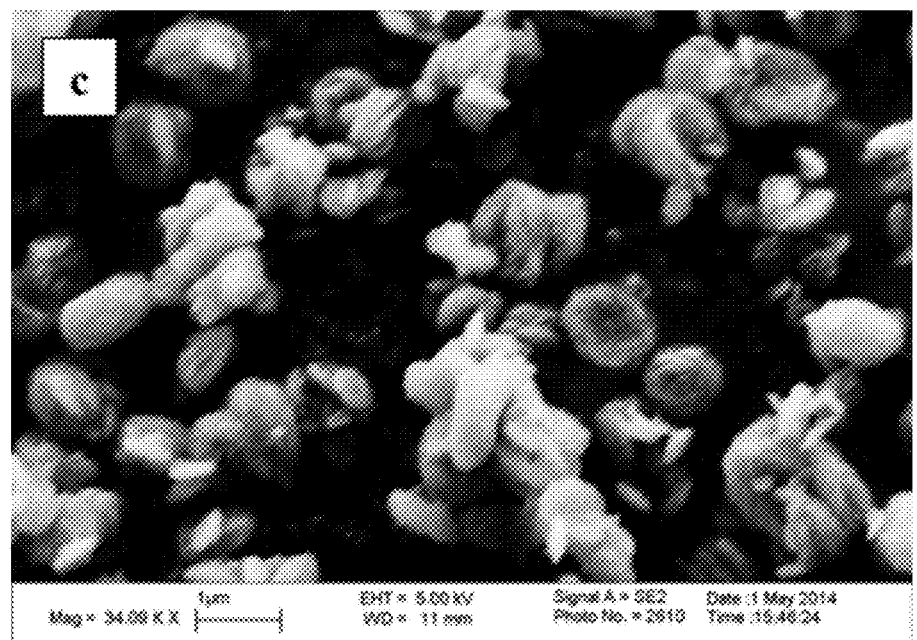

cse          mtw

METHODS FOR PRODUCING CRYSTALLINE MICROPOROUS SOLIDS WITH A NEW CIT-7 TOPOLOGY AND COMPOSITIONS DERIVED FROM THE SAME

CROSS REFERENCE TO RELATED APPLICATIONS

This application claims the benefit of priority to U.S. Provisional Patent Application Nos. 61/930,326, filed Jan. 22, 2014; 61/969,963, filed Mar. 25, 2014; 62/054,247, filed Sep. 23, 2014; 62/013,167, filed Jun. 17, 2014; and 62/077,719, filed Nov. 10, 2014, the contents of each of which are incorporated by reference in their entirety herein.

TECHNICAL FIELD

This disclosure relates to new crystalline microporous solids (including silicate- and aluminosilicate-, and other metal-silicate-based solids), the various compositions comprising 8, 10, 12, and 14-membered inorganic rings, particularly those having RTH, HEU, CIT-7, and IWV topologies having a wide range of Si:Al ratios. This disclosure also provides methods of preparing these and known crystalline microporous solids using certain quaternized imidazolium cation organic structure directing agents, and intermediates used in these methods.

BACKGROUND

It is estimated that over 90% of chemical processes use a catalyst, with 80% being a heterogeneous catalyst, with a global demand of $15 to $20 billion per year. Microporous materials (pores less than 2 nm) are an important type of heterogeneous catalyst as they offer shape and size selective environments for catalysis to occur. Additionally, they often exhibit robust hydrothermal stability which allows them to be used under demanding process conditions, such as fluid catalytic cracking. Synthetic aluminosilicate zeolites are produced on a scale 1.7-2 million metric tons per year, and their use as catalysts comprises 27% of the world market for zeolites. As the cost of the catalyst is estimated to be only 0.1% of the cost of the final product, the demand to innovate in this area remains high. There currently exist over 200 known microporous material frameworks, but of these less than 20 have been commercialized and the market is dominated by only five major frameworks. In many applications, there is only a single structure and composition to achieve optimal performance, motivating much of the research directed at creating new materials.

In recent years there has been considerable interest in 8-MR systems for catalysis and separations. Some of the most promising catalytic applications are the methanol to olefins (MTO) conversion and deNOx. Other 8-MR materials of interest are LEV, CHA and AFX. It has been found that the cage size and connectivity are critical in determining the product distribution for these reactions in 8-MR systems. As RTH possesses a unique connectivity as well as cage size it exhibits unique catalytic performance, which has been shown for MTO using the aluminosilicate material. The RTH topology has 8-MR openings and a 2-dimensional ("2-D") channel system with pore sizes of 4.1×3.8 Å and 5.6×2.5 Å, leading to larger cages. See also C. Baerlocher, L. B. Mccusker, Database of Zeolite Structures, approved by the Structure Commission of the International Zeolite Association, and available at <http://www.izastructure.org/databases/>, (2014).

The molecular sieve (zeolite) with the framework topology of RTH was first described in 1995. It was produced as a borosilicate (RUB-13) using the relatively simple organic structure directing agent ("OSDA") 1,2,2,6,6-pentamethylpiperidinium. Although the borosilicate requires a less exotic OSDA, the small pores of the material prevent the replacement of boron with aluminum. However, in order to produce an aluminosilicate material with the necessary acid strength for the MTO reaction, a more complicated OSDA was required. The next RTH microporous material was produced as an aluminosilicate (SSZ-50) using 2-ethyl-2,5,7,7-tetramethyl-2-azabicyclo[4.1.1]octan-2-ium as the structure directing agent.

But this OSDA requires an elaborate multi-step synthesis adding to the cost and complexity of the preparation, so as to be unlikely this material would be used in commercial production. Some progress has been made to synthesize a OSDA-free version of RTH using seed crystals, but materials so-produced have a very limited compositional range. Additionally, the high Si/Al ratios (Si/Al=41 and 108) may be less than optimal for a catalyst. For all of these reasons an alternative SDA to produce RTH is desired so that it can be tested for applications.

Microporous solids having 2-dimensional channels and 8-MR and 8-/10-MR frameworks are finding increasing utility as catalysts, ion exchange, and adsorption systems. The heulandite (HEU) framework is another topology having a 2-dimensional channel system, and relatively large pore sizes. In the [001] directing there are 10-membered rings (MRs) as well as 8-MRs. Additionally, there is another set of 8-MRs along with [100] direction.

Heulandite materials are divided into two distinct classes based on Si/Al ratio. Those with Si/Al of less than 4 are known as heulandite and those with Si/Al greater than 4 are known as clinoptilolite, or silica-rich heulandite. The key difference in these materials is that those with Si/Al of less than 4 are not thermally stable to calcination above 350° C. A method to produce a high-silica heulandite was first reported by removing aluminum from natural clinoptilolite to make a material with Si/Al=5.5, known as LZ-219. Later, methods were developed to produce synthetic heulandite across a range of Si/Al=2.5-6 using various sources of silica and alumina and a wide range of inorganic cations (Li, Na, K, Rb, Ca) under hydrothermal synthesis (without the use of OSDAs) or acid leaching conditions. These materials have been considered for applications such as gas cleaning and separations, ion exchange, isomerization of 1-butene and xylene, methanol dehydration and acetylene hydration. In any of these applications, the ability to tailor the framework composition is important for material properties such as exchange capacity, hydrothermal stability and pore accessibility.

Crystalline microporous solids of the IWV framework were first prepared as the ITQ-27 framework using the phosphorus-containing structure-directing agent, dimethyldiphenylphosphonium. Its structure comprises seven unique T-sites forming a framework with straight 12-MR channels that are connected by 14-MR openings between them. Since access from one 14-MR opening to the next is through the 12-MR channel, the structure is best described as a two-dimensional, 12-MR framework. Other ITQ structures are known to have larger (e.g., 12-/14-MR) and smaller ring openings, making these materials useful for hydrocarbon processing.

Much of the discovery of new microporous material frameworks and compositions in recent years has resulted from the use of organic structure directing agents (OSDAs), which are normally alkylammonium cations. While OSDAs have led to many new materials, their cost contributes a significant portion of the material cost, which often cannot be recovered as they are normally removed from the material using combustion. In some systems it is possible to partially replace high cost OSDAs with cheaper organics, such as with SSZ-13 where it has been shown that over 80% of the expensive trimethyl-N-1-adamantammonium hydroxide OSDA can be replaced with the much cheaper benzyl trimethyl ammonium hydroxide. Another way is to find methods to synthesize the materials in the absence of OSDAs, but this can often lead to limited product compositions and still does not eliminate processing steps such as ion exchange and calcination. Therefore, an attractive route to lower OSDA costs is to find new, simpler OSDAs to synthesize desired materials.

For at least these reasons, interest is currently high in developing new molecular sieves having 2-dimensional channel systems with 8-MR and 8-/10-MR openings and 12-MR openings.

SUMMARY

The present invention is directed to several new crystalline microporous solids, having 2-dimensional channel systems with 8-MR, 8-/10-MR, and 12-MR channels, and methods of preparing the same. One set comprises crystalline material having an RTH topology generally (including SSZ-50), and especially aluminosilicate compositions having low Si:Al ratios, and methods for preparing these types of materials across a wide range of Si/Al including low Si/Al ratios. A second set, described herein as CIT-7, is a new crystal form, and includes a broad range of compositions having 2-dimensional channels with 8-MR and 10-MR. A third set of materials comprises solids having HEU topology, having 2 dimensional channels and 8-MR and 8-/10-MR openings, especially aluminosilicate materials having high Si:Al ratios. High silica HEU, denoted CIT-8 (California Institute of Technology number 8) can be prepared via topotactic condensation of a layered aluminosilicate material containing an organic structure directing agent. This layered material is denoted CIT-8P. CIT-8 can also be prepared by direct synthesis in hydroxide media using an imidazolium organic structure directing agent (OSDA). A fourth material, which has the IWV framework structure contains a 2-dimensional system of 12-MR channels, which lead to internal 14-MR rings and is prepared at previously unknown compositions.

Also described are the processes and intermediates used in making such compositions. Such compositions and methods include the use of organic structure defining agents (OSDAs) including quaternized imidazolium cations ("quats") and linked pairs of quaternary imidazolium cations ("diquats"). These materials have shown good activity for the methanol-to-olefins reaction (MTO) and have also been proposed as a material for catalytic $NO_X$ reduction. Industrially, imidazoles are produced using the Radziszewski reaction or by dehydrogenation of imidazolines and are available in high purity. The quaternary imidazolium cations of the present invention can then be prepared by standard alkylation methods.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, processes, devices, and systems disclosed. In addition, the drawings are not necessarily drawn to scale. In the drawings:

FIG. 3 and FIG. 4A-C show Scanning Electron Micrographs (SEMs) for materials prepared in Example 1.3. FIG. 4A shows SEM of calcined RTH prepared in fluoride media (sample F4). FIG. 4B shows SEM of calcined RTH synthesized in hydroxide media with sodium (sample H4). FIG. 4C shows SEM of calcined RTH synthesized in hydroxide media without sodium (sample H5).

FIG. 8A shows data for SSZ-13 with Si/Al=19; FIG. 8B shows data for SAPO-34; FIG. 8C shows data for fresh Si/Al=17 RTH (sample H6); FIG. 8D shows data for Si/Al=17 RTH (sample H6; regenerated one time); FIG. 8E shows data for Si/Al=17 RTH (sample H6; regenerated two times); FIG. 8F shows data for Si/Al=29 RTH (sample H8); FIG. 8G shows data for Si/Al=59 (sample H10), showing methanol conversion (open diamonds) to $C_2$ olefins (solid squares), $C_3$ olefins (solid triangles), $C_4$ olefins (solid diamonds), total $C_1$-$C_4$ alkanes (open circles), and $C_5$'s+$C_6$'s (solid circles).

FIG. 26A shows a pattern for calcined IWV produced in hydroxide media at Si/Al=15. FIG. 26B shows a pattern for as-made (lower) and calcined (upper) IWV produced in fluoride media at gel Si/Al=50

DETAILED DESCRIPTION OF ILLUSTRATIVE EMBODIMENTS

Figure 1:
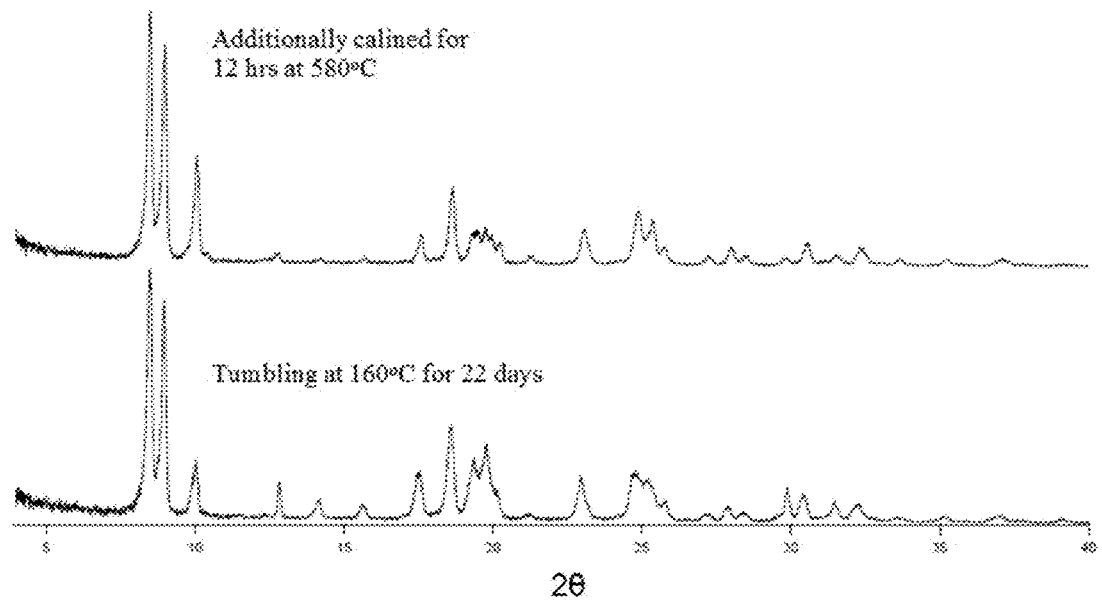
FIG. 1 shows representative powder X-ray diffraction (XRD) patterns of one of the RTH compositions produced by the present methods: as-made (lower) and calcined (upper) aluminosilicate RTH zeolites for composition prepared using 1 $SiO_2$:0.5 Al:0.5 ROH:0.5 HF:14 $H_2O$, where ROH is pentamethylimidazolium hydroxide.

The present invention is directed to crystalline microporous solids of HEU, RTH, CIT-7, and IWV topologies, and processes and intermediates used in making such crystalline materials. Such compositions and methods include the use of organic structure defining agents including quaternized imidazolium cations and linked pair of quaternary imidazolium cations.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) of a process is the ability to provide a microporous material having the designated topologies, and of a product or intermediate, one having the designated topology.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled in the relevant art. However, so as to avoid misunderstanding, the meanings of certain terms will be specifically defined or clarified.

The terms "halo" and "halogen" are used in the conventional sense to refer to a chloro, bromo, fluoro, or iodo substituent.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

Unless otherwise indicated, the term "isolated" means physically separated from the other components so as to be free of solvents or other impurities; additional embodiments include those where the compound is substantially the only solute in a solvent or solvent fraction, such a analytically separated in a liquid or gas chromatography phase.

"Optional" or "optionally" means that the subsequently described circumstance may or may not occur, so that the description includes embodiments where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target molecule or other material is separated and where the target material is not separated, such that subsequence steps are conducted on isolated or in situ generated product.

The terms "separating" or "separated" carries their ordinary meaning as would be understood by the skilled artisan, insofar as it connotes separating or isolating the product material from other starting materials or co-products or side-products (impurities) associated with the reaction conditions yielding the material. As such, it infers that the skilled artisan at least recognizes the existence of the product and takes specific action to separate or isolate it. Absolute purity is not required, though preferred, as the material may contain minor amounts of impurities and the separated or isolated material may contain residual solvent or be dissolved within a solvent used in the reaction or subsequent purification of the material.

As used herein, the term "crystalline microporous solids" or "crystalline microporous silicate or aluminosilicate solids," sometimes referred to as "molecular sieves," are crystalline structures having very regular pore structures of molecular dimensions, i.e., under 2 nm. The term "molecular sieve" refers to the ability of the material to selectively sort molecules based primarily on a size exclusion process. The maximum size of the species that can enter the pores of a crystalline microporous solid is controlled by the dimensions of the channels. These are conventionally defined by the ring size of the aperture, where, for example, the term "8-MR" or "8-membered ring" refers to a closed loop that is typically built from eight tetrahedrally coordinated silicon (or aluminum) atoms and 8 oxygen atoms. In the present case, the structures described comprise 8- or 8- and 10-membered rings or 12-membered rings (designated 8-MR, 8-/10-MR, and 12-MR, respectively). These rings are not necessarily symmetrical, due to a variety of effects including strain induced by the bonding between units that are needed to produce the overall structure, or coordination of some of the oxygen atoms of the rings to cations within the structure. The term "silicate" refers to any composition including silica. It is a general term encompassing, for example, pure-silica, aluminosilicate, borosilicate, or titanosilicate structures. The term "zeolite" refers to an aluminosilicate composition that is a member of this family.

The present invention is directed to several new crystalline microporous solids, having 2-dimensional channel systems with 8-MR, 8-/10-MR openings and 12-MR openings, and methods of preparing the same. One set comprises crystalline material having an RTH topology generally (including SSZ-50), and especially aluminosilicate compositions having low Si:Al ratios, and methods for preparing these types of materials. A second set, described herein as CIT-7, is a new crystal form, and includes a broad range of compositions having 2 dimensional channels and 8-/10-MR openings. A third set of materials comprises solids having HEU topology, having 2-dimensional channels and 8-/10-MR openings, especially aluminosilicate materials having high Si:Al ratios. A fourth set of material comprises solids having IWV topologies, having 2-dimensional channels and 12-MR framework, especially those compositions having high Si:Al ratios. Additional embodiments are directed to methods of making these new compositions. These new methods may also be used to prepare compositions having known Si:Al ratios.

In some embodiments, the crystalline microporous solids may be characterized by the dimensions and directions of the rings (Table 1).

titanium oxide, indium oxide, vanadium oxide, zirconium oxide, or combination or mixture thereof; and (b) a linked pair of quaternary imidazolium cations of a structure:

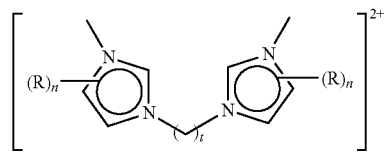

under conditions effective to crystallize a crystalline microporous solid;

wherein t is 3, 4, 5, or 6, preferably 4 or 5; and

R is independently methyl or ethyl, preferably methyl or mainly methyl, and n is independently 1, 2, or 3; said linked pair of quaternary imidazolium cations having associated fluoride or hydroxide ions, preferably substantially free of other halide counterions, i.e., bromide, chloride, or iodide. As used herein, the term "linked pair of quaternary imidazolium cations" is intended to connote that two quaternary

TABLE 1

Representative dimensions of the compositions described herein (from IZA)

| | 8-MR [001]$^a$ | 10-MR [001]$^a$ | 8-MR [100]$^a$ | 8-MR [010] | 12-MR [001]$^a$ | 12-MR [011]$^a$ |
|---|---|---|---|---|---|---|
| CIT-7 | | 5.1 × 6.2 Å | | 2.9 × 5.5 Å | | |
| HEU (CIT-8) | 3.6 × 4.6 Å | 3.1 × 7.5 Å | 2.8 × 4.7 Å | | | |
| RTH | 2.5 × 5.6 Å | | 3.8 × 4.1 Å | | | |
| IWV | | | | | 6.2 × 6.9 Å | 6.2 × 6.9 Å |

$^a$[001], [100], [010], and [011] refer to crystallographic directions. Such directions are provided for guidance only, and may vary slightly in some embodiments. It is understood that these ring directions are for ideal materials. In real materials, small deviations occur.

The inventive processes may be described, at least in part, in terms of hydrothermally treating a composition comprising a silicate source, aluminosilicate source, or metallosilicate source in the presence of an Organic Structure Directing Agent ("OSDA"), described herein and selected depending on the nature of the desired product, under conditions sufficient to form the desired crystalline product, and optionally recovering and further processing the crystalline products. These as-synthesized crystalline materials may contain occluded OSDA within their pore structures, which can be removed by thermal or oxidative treatments. One of the many advantages of the OSDAs of the present invention over phosphorus-containing OSDAs is that they avoid the inclusion of P atoms or oxides on calcining which inevitably occur on use of the phosphorus-containing OSDAs. Similarly, the compositions associated with these processes are also considered within the scope of the invention.

Some embodiments include processes (and compositions) for preparing crystalline microporous solids, each process comprising hydrothermally treating a composition comprising:

(a) (i) at least one source of a silicon oxide, germanium oxide, or combination thereof; and optionally (ii) at least one source of aluminum oxide, boron oxide, gallium oxide, hafnium oxide, iron oxide, tin oxide, imidazolium cations are linked by the carbon linker, and not that the two quaternized cations are necessarily identical, though this is preferred.

Subsets of this embodiment include those where (a) comprises only at least one source of a silicon oxide, germanium oxide, or combination thereof, preferably only at least one source of a silicon oxide. Such methods are useful for producing crystalline silicate microporous solids having an RTH, or CIT-7 topology. Additional subsets of this embodiment include those where (a) comprises only at least one source of a silicon oxide and at least one source of aluminum or titanium oxide. Such methods are useful for producing crystalline microporous solids, especially aluminosilicates or titanosilicates having CIT-7, HEU, RTH or IWV topologies.

In preferred embodiments, the composition being hydrothermally treated comprises only at least one source of silicon oxide or at least one form of silicon oxide and at least one source of aluminum oxides, for the preparation of crystalline microporous silicate and aluminosilicate solids, respectively. In some specific cases, sources of titanium oxide may be substituted or used in conjunction with the sources of aluminum oxide.

As described in the Examples below, depending on specific reaction conditions, particularly temperature and water:Si ratio, the product crystalline microporous silicate solid may independently have an RTH or HEU (e.g., designated CIT-8 or CIT-8P) or IWV or a topology designated as CIT-7.

As used throughout, the counterions of the organic structure directing agents are fluoride or hydroxide, and substantially free of other halide counterions, i.e., bromide, chloride, or iodide. In this context, the term "substantially free" refers to a condition where no bromide, chloride, or iodide are added to the composition or process, and in fact, reasonable efforts are taken to remove these from the composition or process, e.g., by ion exchange methods. It does not require absolute absence of these anions, as for example, as may result from incidental residual bromide, chloride, or iodide contained within the inorganic materials.

In other embodiments, it may be desirable to hydrothermally treat at least one source of a silicon oxide, germanium oxide, or combination thereof under analogous conditions.

The dication designation shown in Formula (I) may also be characterized by the resonance structures shown here, reflecting the nature of the cationic charge distribution over the imidazolium cations.

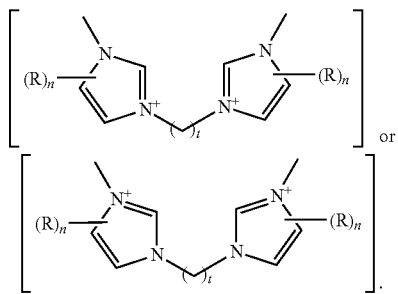

In certain preferred embodiments, the linked pair of quaternary imidazolium cations has a structure:

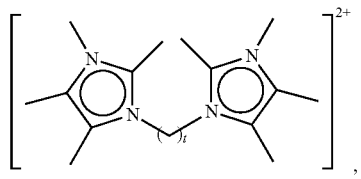

where t is 3, 4, 5, or 6; and the associated ions are preferably hydroxide. When t=3, 4, or 5, in some cases, compositions of the CIT-8P type morphology can be prepared. When t=3, 4, or 5, in some cases, the formation of CIT-7 type morphology appears to be favored, whereas when t=5, in some cases, the formation of the RTH topology is favored. IWV can be formed when t=4, 5, or 6 (see, e.g., Tables 9, 9B, 14, and 15 and Example 7.2).

In some embodiments, the a linked pair of quaternary imidazolium cations may be described not only with respect to ethyl and methyl groups, but also in terms of a C/N+ ratio, where the C represents the number of carbon atoms and N+ represents the number of quaternized nitrogen atoms associated with each imidazolium cation. In these embodiments, the C/N+ ratio for each imidazolium can be independently in the range of from t 6:1 to 10:1, preferably from 6:1, from 7:1, or from 8:1 to 9:1, more preferably 8:1. For the purpose of counting carbon atoms, the linking carbon chain is considered to provide a single carbon atom to each imidazolium cation. For example, in the embodiment where t is 5, and the linked pair of quaternary imidazolium cations has associated hydroxide ions, the linked pair of quaternary imidazolium cations may be represented by the structure:

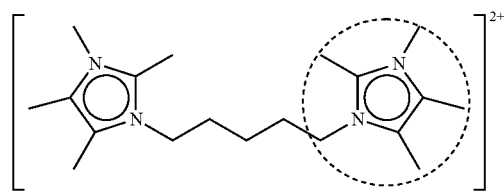

each imidazolium cation would have eight associated carbon atoms (3 ring carbons, 4 methyl carbons, and one linking carbon) and one charged quaternary nitrogen atom, for a C/N+ ratio of 8:1. Since, by this definition, the linking carbon chain provides only a single carbon to each imidazolium cation, this ratio would be independent of the value of t. (Note that other definitions sometimes used in the art provide for an accounting of all of the carbons in the linking chain. In this convention, the values for C/N+ ratio are correspondingly higher to account for all of the linking carbon atoms. For example, by this convention, the example above would have nineteen associated carbon atoms (6 ring carbons, 8 methyl carbons, and five linking carbons) and two charged quaternary nitrogen atoms, for a C/N+ ratio of 19:2 or 9.5:1).

Other embodiments relate to processes for the preparation of crystalline microporous solids, each process comprising hydrothermally treating a composition comprising:
  (a) (i) at least one source of silicon oxide and
    (ii) at least one source of aluminum oxide, boron oxide, gallium oxide, hafnium oxide, iron oxide, tin oxide, titanium oxide, indium oxide, vanadium oxide, zirconium oxide, or combination or mixture thereof in the presence of an organic complex comprising
  (b) an imidazolium cation comprising methyl and ethyl groups and having a C/N+ ratio in a range of from 6:1 to 10:1, preferably from 6:1, from 7:1, or from 8:1 to about 9:1, or 8:1, such that the imidazolium has, for example,
    (i) 3, 4, or 5 methyl groups or
    (ii) 2, 3, or 4 methyl groups and one ethyl group and
  (c) an associated hydroxide or fluoride anion, preferably hydroxide and preferably substantially free of other halide counterions, i.e., bromide, chloride, or iodide;
under conditions effective to crystallize an RTH-, HEU, CIT-7-, or IWV-type crystalline microporous solid.

In some preferred embodiments, the processes are used to prepare crystalline aluminosilicate solids. Such embodiments include those comprising hydrothermally treating a composition comprising:
  (a) (i) at least one source of a silicon oxide, germanium oxide, or combination thereof;
    (ii) at least one source of aluminum oxide; and optionally
    (iii) at least one source of boron oxide, gallium oxide, hafnium oxide, iron oxide, tin oxide, titanium oxide, indium oxide, vanadium oxide, zirconium oxide, or combination or mixture thereof; and
  (b) an imidazolium cation comprising methyl and ethyl groups and having a C/N+ ratio in a range of from 6:1 to 10:1, preferably from 6:1, from 7:1, or 8:1 to 9:1, more preferably 8:1, such that the imidazolium, for example, has (i) 3, 4, or 5 methyl groups or (ii) 2, 3, or 4 methyl groups and one ethyl group, and (iii) a hydroxide or fluoride anion, preferably substantially free of other halide counterions, i.e., bromide, chloride, or iodide;

under the conditions effective to crystallize an RTH-, HEU-, CIT-7, or IWV-type crystalline microporous solid, preferably an aluminosilicate solid (described herein; see Examples 3-9 for exemplary conditions).

Again, the separate formation of each of the RTH-, HEU, CIT-7, or IWV-type crystalline microporous solid can be directed by the separate choice of temperature, water:Si ratios, and other parameters, some of which are described in the Examples as specific embodiments. For example, the RTH topology can be obtained using HF or hydroxide-mediated conditions, at temperatures ranging from about 100° C. to about 200° C., preferably from about 150° C. to about 180° C., or more preferably from about 160° C. to about 175° C. and a water:Si ratio ranging from about 2:1 to about 20:1, preferably from about 4:1 to about 10:1 in fluoride mediated syntheses or from about 2:1 to about 40:1, preferably from about 15:1 to about 20:1 in hydroxide mediated syntheses. Non-limiting, exemplary conditions are shown, e.g., in Examples 3, 5 and 7.

The CIT-7-type topology can be obtained using HF or hydroxide-mediated conditions, at temperatures ranging from about 150° C. to about 180° C., or preferably from about 160° C. to about 175° C. and at lower water:Si ratios (e.g., from about 2:1 to about 5:1), with silicates in HF mediated syntheses, or with aluminosilicates (Si:Al ratios from about 15:1 to about 250:1, preferably about 20:1) in HF- or hydroxide-mediated syntheses, using OSDAs comprising monoquat imidazolium cations or preferably those having linked pairs of quaternized imidazolium cations, where the linking chain length is 3-5 carbons, preferably about 4 carbons. Non-limiting, exemplary conditions are shown, e.g., in Examples 3 and 8.

The HEU topology can be obtained using HF or hydroxide-mediated conditions, at temperatures ranging from about 100° C. to about 200° C., preferably from about 150° C. to about 180° C., or more preferably from about 160° C. to about 175° C. and at lower water:Si ratios (e.g., from about 4:1 to about 7:1) and Si:Al ratios (e.g., from about 5:1 to about 50:1, preferably from about 5:1 to about 20:1), using OSDAs having linked pairs of quaternized imidazolium cations, where the linking chain length is 3-5 carbons. Non-limiting, exemplary conditions are shown, e.g., in Examples 3 and 9.

While the pure silicate-containing crystalline microporous solids and the HEU and CIT-7 topologies appear to require, or at least favor, the use of the linked pair of quaternary imidazolium cations, other crystalline materials appear to favor the use of mono-quaternary imidazolium cations having the parameters described above. Exemplary imidazolium cations include those aromatic structures described by a resonance form that is:

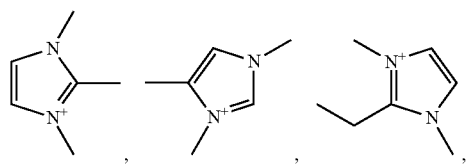

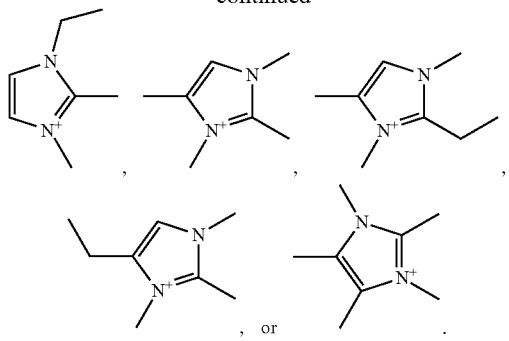

Typical sources of silicon oxide for the reaction mixtures include alkoxides, hydroxides, or oxides of silicon, or combination thereof. Exemplary compounds also include silicates (including sodium silicate), silica hydrogel, silicic acid, fumed silica, colloidal silica, tetra-alkyl orthosilicates, and silica hydroxides.

Typical sources of aluminum oxide for the reaction mixture include aluminates, alumina, aluminum colloids, aluminum alkoxides, aluminum oxide coated on silica sol, hydrated alumina gels such as Al(OH)$_3$ and a sodium aluminate. Sources of aluminum oxide may also comprises an alkoxide, hydroxide, or oxide of aluminum, or combination thereof. Additionally, the sources of alumina may also comprise other ligands as well, for example acetylacetonate, carboxylates, and oxalates; such compounds are well known as useful in hydrothermal or sol-gel syntheses.

Sources of boron oxide, gallium oxide, hafnium oxide, iron oxide, tin oxide, titanium oxide, indium oxide, vanadium oxide, and/or zirconium oxide can be added in forms corresponding to their aluminum and silicon counterparts.

In other embodiments, a source inorganic reagent may also provide a source of aluminum. In some cases, the source inorganic also provides a source of silicate. The source zeolite in its dealuminated form may also be used as a source of silicate, with additional silicon added using, for example, the conventional sources listed above. Use of a source zeolite reagent as a source of alumina for the present process is more completely described in U.S. Pat. No. 4,503,024, the disclosure of which is incorporated herein by reference.

In those cases where the source of silicon or aluminum is an alkoxide, their respective empirical formulae are preferably Si(OR)$_4$ and Al(OR)$_3$, where R is an alkyl group of 1-6 carbon atoms, including methyl, ethyl, n-propyl, isopropyl, n-butyl, sec-butyl, tert-butyl, n-pentyl, isopentyl, hexyl Some of these compounds, especially Al(OR)$_3$, form complicated bridging structures in solution, even before hydrolysis. In some embodiments, the silicon alkoxide is tetraethyl orthosilicate (TEOS) and the aluminum alkoxide is Al(i-OPr)$_3$.

In the processes directed to preparing the aluminosilicate zeolites, some embodiments provide that the ratio of Si:Al in the composition is in a range of from about 5:1 to about 250:1. Additional embodiments include those where the ratio is in a range bounded at the lower end by a value of about 5:1, 10:1, 15:1, 20:1, or 25:1 and bounded at the upper end by a value of about 250:1, 100:1, 50:1, 30:1, 25:1, 20:1, 15:1, or about 10:1. In those embodiments where some of the Al are substituted by B, Ga, Hf, Fe, Sn, Ti, In, V, or Zr, these ratios refer to the ratio of Si:(Al+B, Ga, Hf, Fe, Sn, Ti, In, V, and/or Zr). In some cases, these lead to crystalline compositions having Si:Al ratios which are lower than the forming compositions (see, e.g., Table 5). In other cases, the crystalline compositions may have Si:Al ratios which are higher than the forming compositions (see, e.g., Table 15).

The compositions of these processes may also include mineralizing media including aqueous HF or aqueous hydroxide. Where the media comprise aqueous hydroxide, the source of the hydroxide may be an alkali metal hydroxide and/or an alkaline earth metal hydroxide, such as the hydroxide of sodium, potassium, lithium, cesium, rubidium, barium, calcium, and magnesium, is used in the reaction mixture. The OSDA may be used to provide hydroxide ion, thereby reducing or eliminating the alkali metal hydroxide quantity required. The alkali metal cation or alkaline earth cation may be part of the as-synthesized crystalline oxide material, in order to balance valence electron charges therein.

In some embodiments, the ratio of imidazolium cation:Si is in a range of from about 0.05:1 to about 1:1. In the embodiments where the OSDA is a linked pair of quaternary imidazolium cations, each imidazolium moiety is considered individually. Certain embodiments provide preferred ratios, depending on the nature of the mineralizing system; i.e., whether it is hydroxide mediated or fluoride mediated. In the fluoride mediated systems, certain preferred embodiments include those where the range of the imidazolium cation:Si ratio is in a range of from about 0.2:1 to about 1:1, more preferably about 0.5:1. In hydroxide mediated systems, the preferred imidazolium cation:Si is typically in a range of from about 0.05:1 to about 1:1, preferably about 0.2:1.

In other embodiments, the ratio of water:Si is in a range of from about 2:1 to about 20:1, preferably in a range of from about 4:1 to about 10:1. Additional embodiments include those where the range is bounded at the lower end by a value of about 2:1, 3:1, 4:1, 5:1, 6:1, 7:1, 8:1, 9:1, 10:1, 12:1, 14:1, 16:1, 18:1, or 20:1 and bounded at the upper end by a value of about 20:1, 18:1, 16:1, 14:1, 12:1, or about 10:1. As with some of the other parameters, the preferred water:Si ratio may depend on the inorganic system, whether it is hydroxide mediated or fluoride mediated. In the fluoride mediated systems, a preferred water:Si range is from about 2:1 to 20:1 and most preferably 4:1 to 10:1. In hydroxide mediated system, a preferred water: Si range is from about 2:1 to 40:1 and most preferably about 15-20:1.

In processing the crystalline microporous solids, the reaction mixture is maintained at an elevated temperature until the crystals of the desired product form are formed. The hydrothermal crystallization is usually conducted under autogenous pressure, at a temperature between 100° C. to about 200° C., preferably about 140° C. to about 180° C. or from about 160° C. to about 180° C., for a time effective for crystallizing the desired crystalline microporous solid. The crystallization period is typically greater than I day and preferably from about 1 day to about 40 days, or from about 3 days to about 20 days. Preferably, the zeolite is prepared using mild stirring or agitation.

During the hydrothermal crystallization step, the crystalline microporous solids can be allowed to nucleate spontaneously from the reaction mixture. The use of product crystals as seed material can be advantageous in decreasing the time necessary for complete crystallization to occur. In addition, seeding can lead to an increased purity of the product obtained by promoting the nucleation and/or formation of the desired crystalline microporous solid over any undesired phases. When used as seeds, such seed crystals are added in an amount between 0.1 and 5% or between 0.1 and 10% of the weight of silicate-source used in the reaction mixture.

Once the crystals have formed, the solid product can be separated from the reaction mixture by standard mechanical separation techniques such as filtration or centrifugation. The crystals can be water-washed and then dried, e.g., at 90° C. to 150° C. for from 8 to 24 hours, to obtain the as-synthesized crystalline microporous solids. The drying step can be performed at atmospheric pressure or under vacuum.

In various embodiments, the processes described herein produce or are capable of producing compositionally "clean" crystalline microporous materials. That is, in various embodiments, the crystalline microporous materials described herein are at least 75%, 80%, 85%, 90%, 95%, or 98% by weight of the nominal topology. In some embodiments, the crystalline microporous materials exhibit XRD patterns where other crystalline topologies are undetectable.

Similarly, in various embodiments the as-formed, calcined, or doped microporous materials that are free from phosphorus atoms or oxides.

The hydrothermal processes provide as-synthesized crystalline materials having the desired topology which contain the imidazolium OSDAs used to prepare the materials occluded in the pore structures, and these compositions are considered within the scope of the present invention.

The crystalline microporous solids can be used as-synthesized, but preferably are thermally treated (calcined), in part to remove the occluded organic OSDAs. For example, in certain embodiments, the isolated as-synthesized crystalline intermediate are treated under oxidative (e.g., air or oxygen) or inert atmosphere at at least one temperature in a range of from about 350° C. to about 850° C. or about 1000° C. When a strongly oxidizing atmosphere is uses (e.g., ozone), the temperature is generally lower, for example, in a range from about 25° C. to about 200° C. In some embodiments, the as-synthesized intermediates are calcined first under an inert atmosphere to pyrolyze the organic occlusions, then calcined in air (optionally including added $O_2$ or ozone) to remove the deposited carbon. In other embodiments, the as-synthesized zeolites are calcined directly under oxidizing conditions. Representative ramp rates are provided in the Examples. Note that the calcining or pyrolysis reactions result in the formation of crystalline microporous materials that are free from P atoms or oxides, a distinguishing feature over materials made from some other methods.

It is also often desirable to remove any alkali metal cation by ion exchange and replace it with hydrogen, ammonium, or any desired metal ion. The zeolite can be leached with chelating agents, e.g., EDTA or dilute acid solutions, to increase the silica to alumina mole ratio. The crystalline microporous solid can also be steamed; steaming helps stabilize the crystalline lattice to attack from acids. Alternatively, or additionally, the calcined materials may be treated with aqueous ammonium salts (e.g., $NH_4NO_3$) to remove any residual inorganic cations in the pores of the crystalline solid.

The crystalline microporous solids can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired.

Metals may also be introduced into the crystalline microporous solid by replacing some of the cations in the crystalline microporous solid with metal cations via standard ion exchange techniques. (see, for example, U.S. Pat. No. 3,140,249 issued Jul. 7, 1964 to Plank et al.; U.S. Pat. No.

3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group 1, Group 2 and Group 8 metals, as well as their mixtures. Cations of metals such as rare earth, Mn, Ca, Mg, Zn, Cd, Pt, Pd, Ni, Co, Ti, Al, Sn, and Fe are particularly preferred.

Following contact with the salt solution of the desired replacing cation, the crystalline microporous solid is typically washed with water and dried at temperatures ranging from 65° C. to about 200° C. After washing, the crystalline microporous solid can be calcined in air or inert gas at temperatures ranging from about 25° C. to about 200° C. or from about 200° C. to about 850° C. or about 1000° C., as described above and depending on the nature of the calcining atmosphere, for periods of time ranging from 1 to 48 hours or more, to produce a catalytically active product especially useful in hydrocarbon conversion processes. Regardless of the cations present in the synthesized form of the crystalline microporous solid, the spatial arrangement of the atoms which form the basic crystal lattice of the crystalline solid remains essentially unchanged.

The crystalline microporous solids may also be treated under conditions so as to incorporate at least one type of transition metal or transition metal oxide catalyst into the pore structure, for example by vapor or chemical deposition or precipitation. As used herein, the term "transition metal" refers to any element in the d-block of the periodic table, which includes groups 3 to 12 on the periodic table. In actual practice, the f-block lanthanide and actinide series are also considered transition metals and are called "inner transition metals. Scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof are preferred.

The as-synthesized or calcined crystalline microporous solids can be formed into a wide variety of physical shapes. Generally speaking, the zeolite can be in the form of a powder, a granule, or a molded product, such as extrudate. In cases where the catalyst is molded, such as by extrusion with an organic binder, these crystalline solids can be extruded before drying, or, dried or partially dried and then extruded. The crystalline microporous solids can be composited with other materials resistant to the temperatures and other conditions employed in organic conversion processes. Such matrix materials include active and inactive materials and synthetic or naturally occurring crystalline solids, including zeolites, as well as inorganic materials such as clays, silica and metal oxides.

To this point, the embodiments have been described mainly in terms of processes to prepare the crystalline microporous solids, but the compositions used in these processes are also considered within the scope of the present invention(s). For the sake of completeness, some of these are repeated here, but this partial listing should not be interpreted as abandoning those embodiments not specifically listed.

Certain embodiments include those compositions, especially useful for preparing crystalline microporous silicate solids, comprising:
(a) at least one source of a silicon oxide (optionally including germanium oxide, or combination thereof);
(b) a linked pair of quaternary imidazolium cations of a structure:

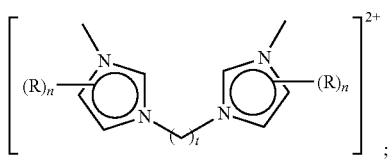

wherein t is 3, 4, 5, or 6, preferably 4 or 5; and
R is independently methyl or ethyl, and n is independently 1, 2, or 3;
said linked pair of quaternary imidazolium cations having associated fluoride or hydroxide ions, and as more broadly described as above; and
(c) optionally at least one crystal of a compositionally consistent crystalline HEU, RTH, CIT-7, or IWV solid. In this regard, the compositions preferably, but not necessarily, contain crystals of any one of the compositionally consistent crystalline HEU, RTH, or CIT-7 solid. In some of these embodiments, a portion of the linked pair of quaternary imidazolium cations is occluded in the pores of the crystals.

Certain additional embodiments include those compositions, especially useful for preparing other crystalline microporous solids, said compositions comprising:
(a) at least one source of a silicon oxide (germanium oxide, or combination thereof);
(b) at least one source of aluminum oxide, boron oxide, gallium oxide, hafnium oxide, iron oxide, tin oxide, titanium oxide, indium oxide, vanadium oxide, zirconium oxide, or combination or mixture thereof; and
(c) an imidazolium cation comprising methyl and ethyl groups and having a C/N+ ratio in a range of from 6:1 to 10:1, preferably from 6:1, from 7:1, or from 8:1 to 9:1 or 8:1, such that the imidazolium has, for example,
(i) 3, 4, or 5 methyl groups or
(ii) 2, 3, or 4 methyl groups and one ethyl group and
(c) a hydroxide or fluoride anion, preferably substantially free of other halide counterions, i.e., bromide, chloride, or iodide; and
(d) optionally a compositionally consistent crystalline HEU, RTH, CIT-7, or IWV solid. Again, in this regard, a preferred embodiment is a composition useful for creating aluminosilicate products—i.e., where at least one source of source of aluminum oxide is present. Also, and again, the compositions preferably, but not necessarily, contain crystals of any one of the compositionally consistent crystalline HEU, RTH, CIT-7, or IWV solid. In some of these embodiments, a portion of the imidazolium cation is occluded in the pores of the crystals.

Additional embodiments include those described above, as well as embodiments where the composition does independently contain a crystalline HEU, RTH, CIT-7, or IWV composition, and particularly a compositionally consistent crystalline HEU, RTH, CIT-7, or IWV composition. As used herein, the term "compositionally consistent crystalline HEU, RTH, CIT-7, or IWV composition" describes a crystalline composition that has the same topology of the named framework, and preferably is a silicate version of that topology or the crystalline composition contains the same types of oxides as do the sources of oxides, albeit not necessarily in the same atomic or molecular proportions—e.g., derived from added seed crystals, hydrothermally formed crystals, or both. Here, the term "substantially free" refers to the absence of added materials having different topologies than the present RTH, HEU, or CIT-7 crystals, again which may be present either as added seed crystals or as formed during hydrothermal treatment of the composition.

The imidazolium cations used in the compositions, especially useful for preparing these crystalline materials, may be described by a resonance form that is:

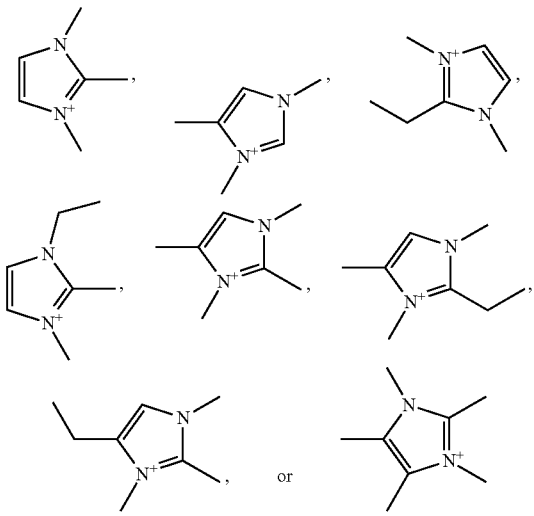

The sources of silicon oxide, aluminum oxides, boron oxide, gallium oxide, hafnium oxide, iron oxide, tin oxide, titanium oxide, indium oxide, vanadium oxide, and/or zirconium oxide used in these compositions are as described above in terms of the processes.

Similarly, the specific chemistries associated with the HF and hydroxide mediated processes (including ratios of imidazolium cation to Si, water to Si, and Si to Al) and described above are also considered within the description of the corresponding compositions.

In certain separate embodiments, the compositions are solutions or gels, as understood by those of ordinary skill in this art.

Also considered within the scope of the present invention(s) are those crystalline compositions comprising a crystalline microporous solid, prepared by any of the processes described herein, either as-synthesized, calcined, or otherwise modified. Some of these embodiments include those crystalline silicate compositions having an RTH structure, an HEU structure, a CIT-7 structure, or an IWV structure and having pores at least some of which are occluded with a linked pair of quaternary imidazolium cations of a structure:

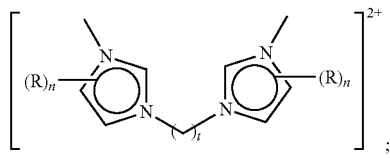

including those OSDAs as more fully described above, and those crystalline compositions having pores, at least some of which are occluded with an organic complex comprising (a) an imidazolium cation comprising methyl and ethyl groups and having a C/N+ ratio in a range of from 6:1 to 10:1, preferably from 6:1, from 7:1, or from 8:1 to 9:1, more preferably 8:1.

As described below, specific embodiments include those crystalline compositions having an RTH structure, an HEU structure, a CIT-7 structure, or an IWV structure where the occluded linked pair of imidazolium cations ("diquat") or mono-quaternized imidazolium cations according ("monoquats") can be described by a resonance form that is:

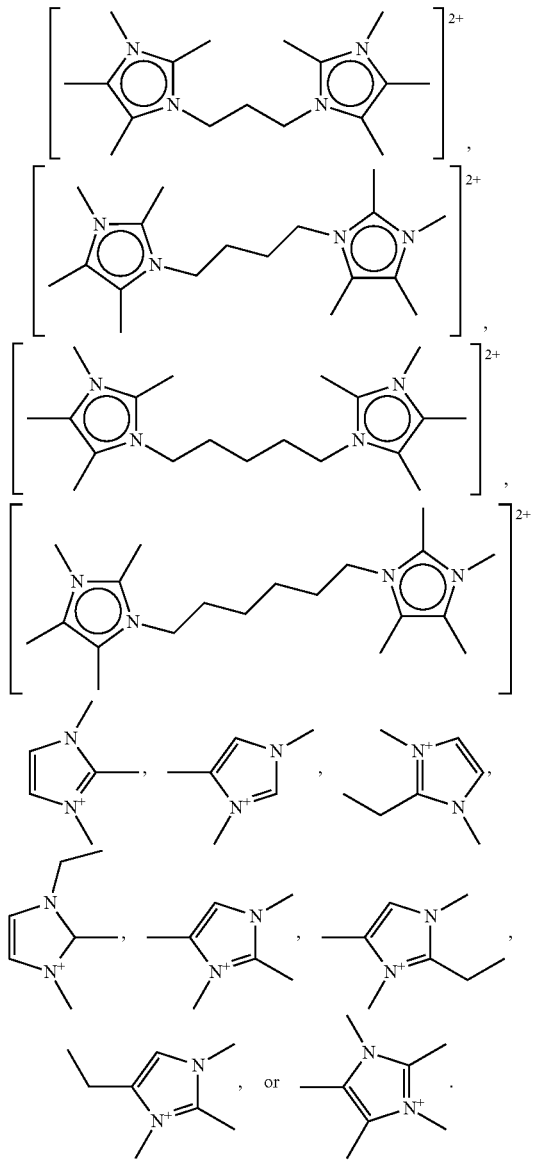

The specific nature of the occluded linked pair of imidazolium cations ("diquat") or mono-quaternized imidazolium cations according ("monoquats") in each case reflects that OSDA used in in the preparation of the specific crystalline microporous material.

The crystalline compositions containing the occluded linked pair of quaternary imidazolium cations or quaternized imidazolium cation include those compositions where the ratio of Si:Al is in a range of from about 5:1 to about ∞:1 (i.e., pure silicate). Additional independent embodiments include those crystalline compositions with the occluded OSDA where the ratio of Si:Al is in a range from about 4:1 to 5:1, from about 5:1 to about 7.3:1, from about 7.3:1 to about 10:1, from about 10:1 to about 12.3:1, from about 12.3:1 to about 15:1, from about 15:1 to about 17.3:1, from about 17.3:1 to about 20:1, from about 20:1 to about 25:1, from about 25:1 to about 30:1, from about 30:1 to about 50:1, from about 50:1 to about 75:1, from about 75:1 to about 100:1, from about 100:1, from about 100:1 to about 250:1, from about 250:1 to about ∞:1, or a combination of two or more of these ranges. Note that a Si:Al ratio of infinity (∞) corresponds to a silicate composition substantially free of Al.

Still further embodiments include those calcined, doped, or otherwise modified crystalline compositions having RTH, HEU, CIT-7, or IWV structures prepared by these inventive methods, and absent the occluded linked pair of quaternary imidazolium cations or imidazolium cations, that exhibit Si:Al ratios over one or more of these ranges.

Figure 6:
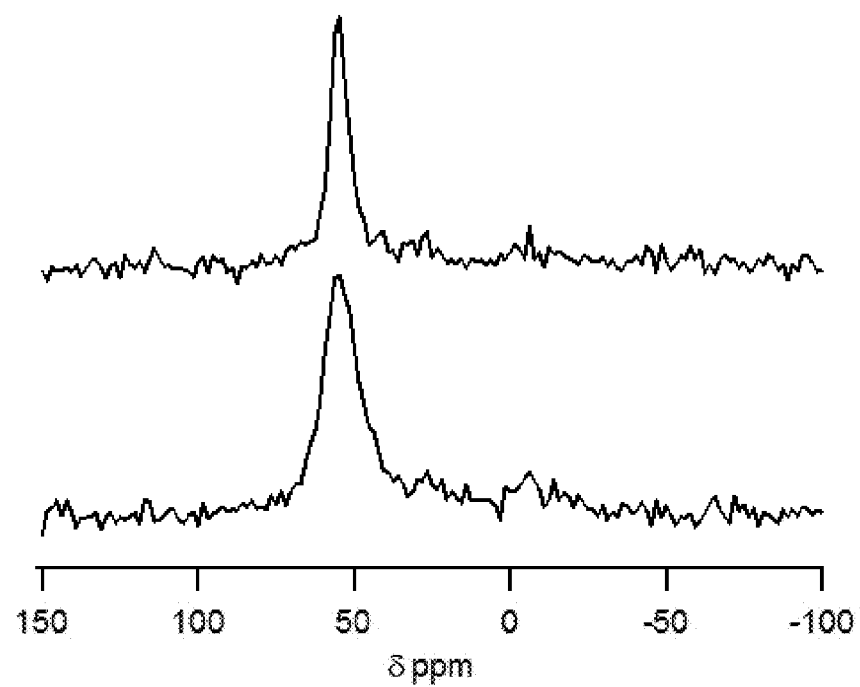
FIG. 6 shows $^{27}Al$ MAS NMR spectra of low silica RTH synthesized in hydroxide media (lower, sample H1) and prepared in fluoride media (upper, sample F2). The single resonance is at 54 ppm.

Additional embodiments include those crystalline microporous solids having an RTH structure, absent the occluded linked pair of quaternary imidazolium cations or imidazolium cations (i.e., where these organic materials have been removed) comprising (a) silicon oxide and (b) aluminum oxide, boron oxide, gallium oxide, hafnium oxide, iron oxide, tin oxide, titanium oxide, indium oxide, vanadium oxide, zirconium oxide, or combination thereof, wherein the molar ratio of (a) to (b) is in a range of from about 5 to about 20, from about 5 to about 15, from about 5 to about 10, or from about 10 to about 15. In certain of these embodiments, the frameworks of these crystalline aluminosilicate zeolites contain oxides of silicon and at least aluminum. In certain of these embodiments, the solids exhibit an XRD diffraction pattern the same as or consistent with that shown in FIG. 1, FIG. 2, or FIG. 9A/B, reflective of the pore sizes comparable to or the same as those described in Table 1. In other embodiments, the crystalline RTH solid exhibits a single peak in the $^{27}$Al MAS spectrum, in some cases having a chemical shift 54 ppm downfield of a peak corresponding to aqueous $Al(NO_3)_3$ as shown in FIG. 6. In other embodiments, these microporous solids contain the doped metals or transition metals or oxides described herein. Additional characteristics of these materials may be found in the Examples.

Still further embodiments include those crystalline microporous solids having an HEU structure, absent the occluded linked pair of quaternary imidazolium cations or imidazolium cations (i.e., where these organic materials have been removed) comprising (a) silicon oxide and (b) aluminum oxide and optionally boron oxide, gallium oxide, hafnium oxide, iron oxide, tin oxide, titanium oxide, indium oxide, vanadium oxide, zirconium oxide, or combination thereof, wherein the molar ratio of (a) to (b) is in a range of from about 5 to about 7.3, from 7.3 to about 10, from about 10 to about 12.3, from about 12.3 to about 15, from about 15 to about 17.3, from about 17.3 to about 20, or a combination of two or more of these ranges. In certain of these embodiments, the frameworks of these crystalline aluminosilicate zeolites contain only alumina and silica. In certain embodiments, these crystalline microporous silicate or aluminosilicate solids having an HEU structure were prepared by either topotactic condensation from a layered precursor material, denoted CIT-8P, or by direct synthesis, as described herein.

Figure 27:
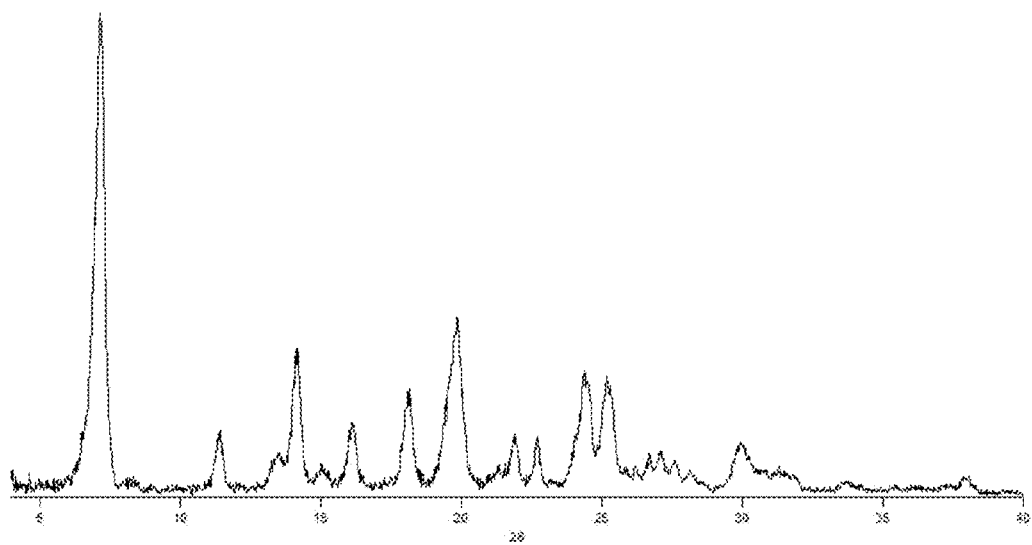
FIG. 27 shows a representative powder X-ray diffraction (XRD) pattern for as-made CIT-8P, as described in Example 9.1.
Figure 28:
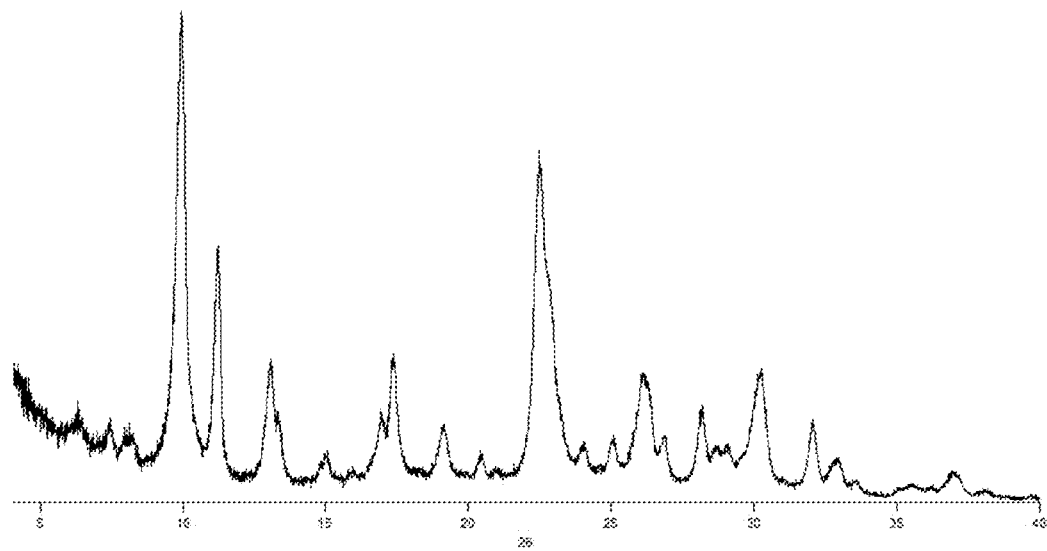
FIG. 28 shows a representative powder X-ray diffraction (XRD) pattern for calcined CIT-8, as described in Example 9.1.
Figure 29:
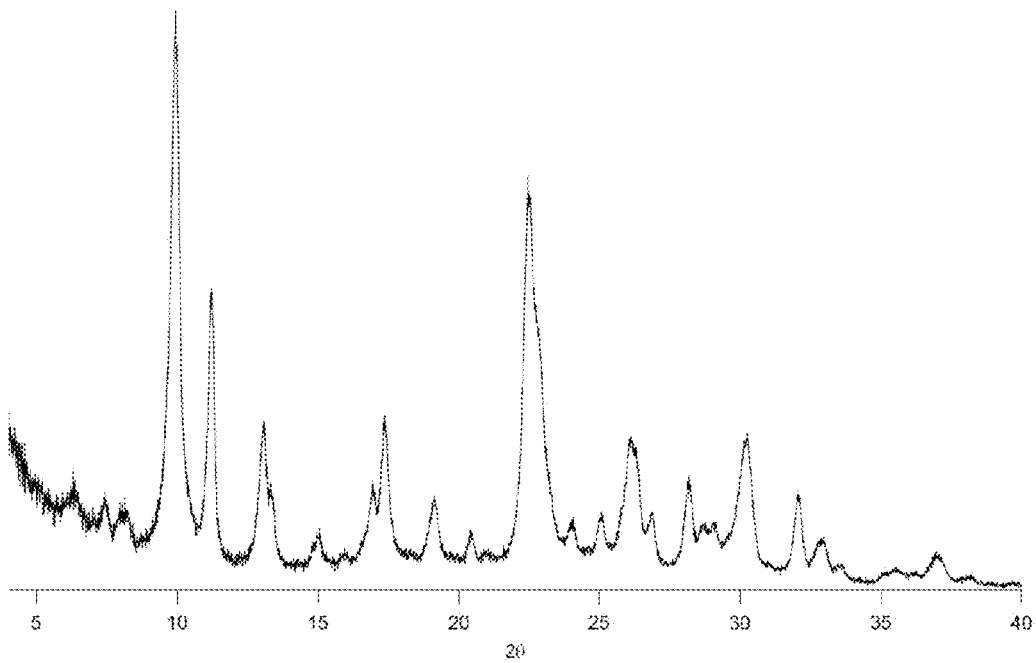
FIG. 29 shows representative powder X-ray diffraction (XRD) pattern for calcined HEU made in hydroxide media, as described in Example 9.1.
Figure 30A:
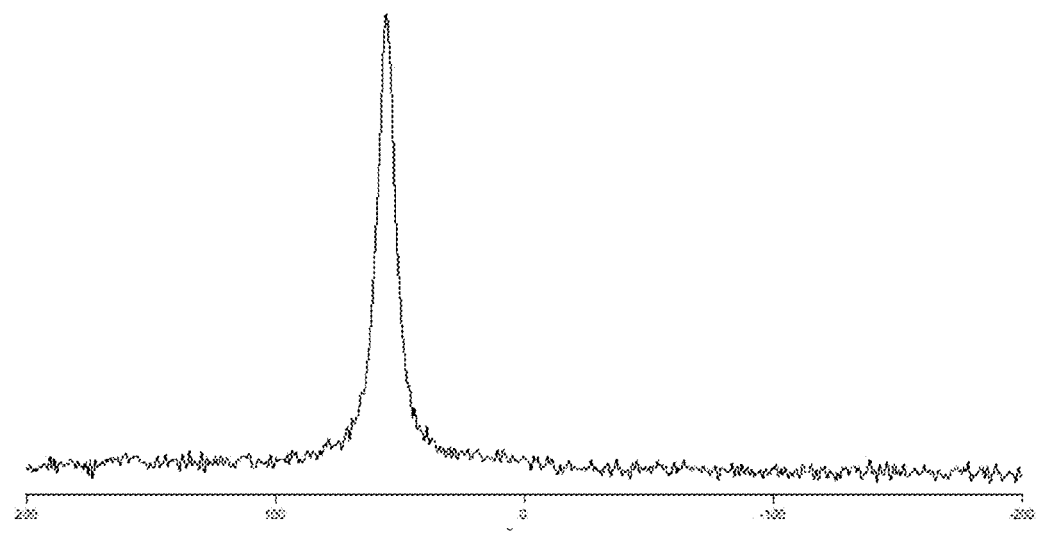
FIG. 30A show a $^{27}Al$ MAS NMR spectrum for calcined HEU produced in hydroxide media. The single resonance in this spectrum is consistent with tetrahedral aluminum, that is aluminum in the framework.
Figure 30B:
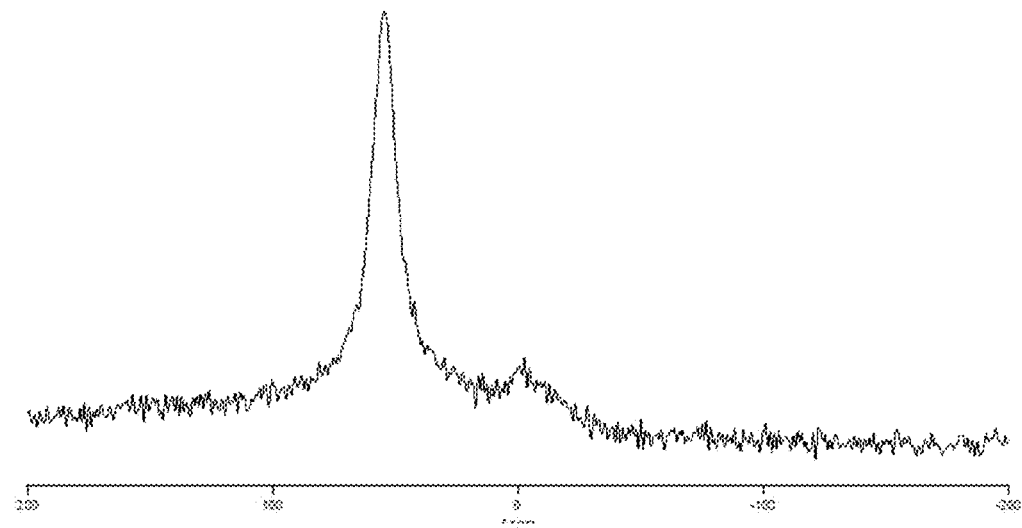
FIG. 30B show a $^{27}Al$ MAS NMR spectrum for calcined HEU produced in fluoride media. The majority of the aluminum in this sample is tetrahedral but there is a small amount of octahedral aluminum (0 ppm).
Figure 31:
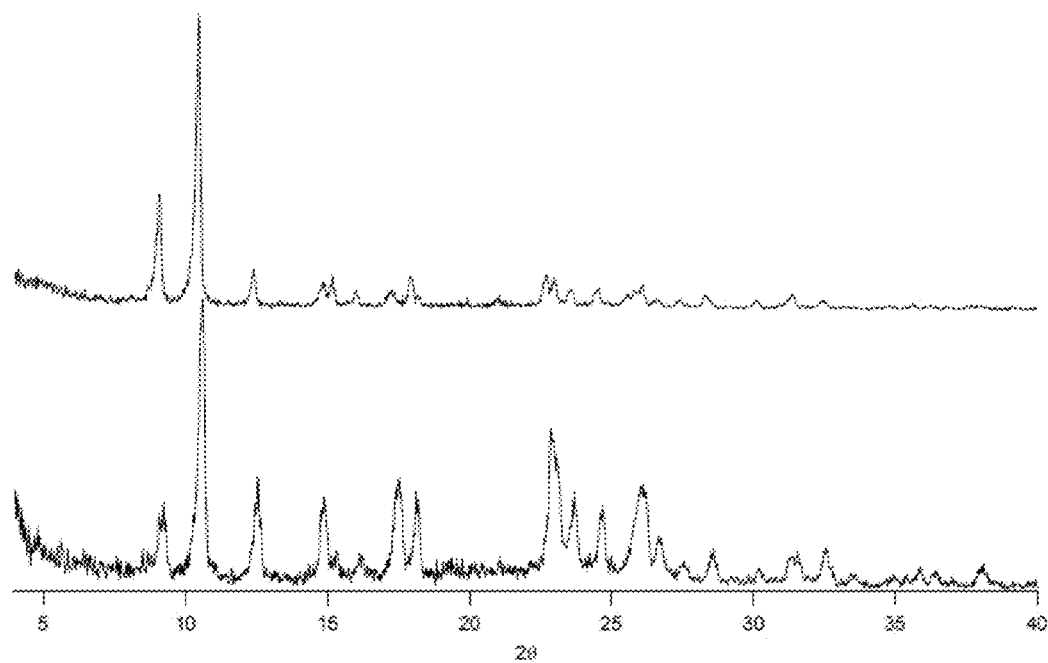
FIG. 31 shows representative powder X-ray diffraction (XRD) patterns for as-made pure-silica STW (lower) and calcined pure-silica STW (upper), as described in Example 9.1.
Figure 32:
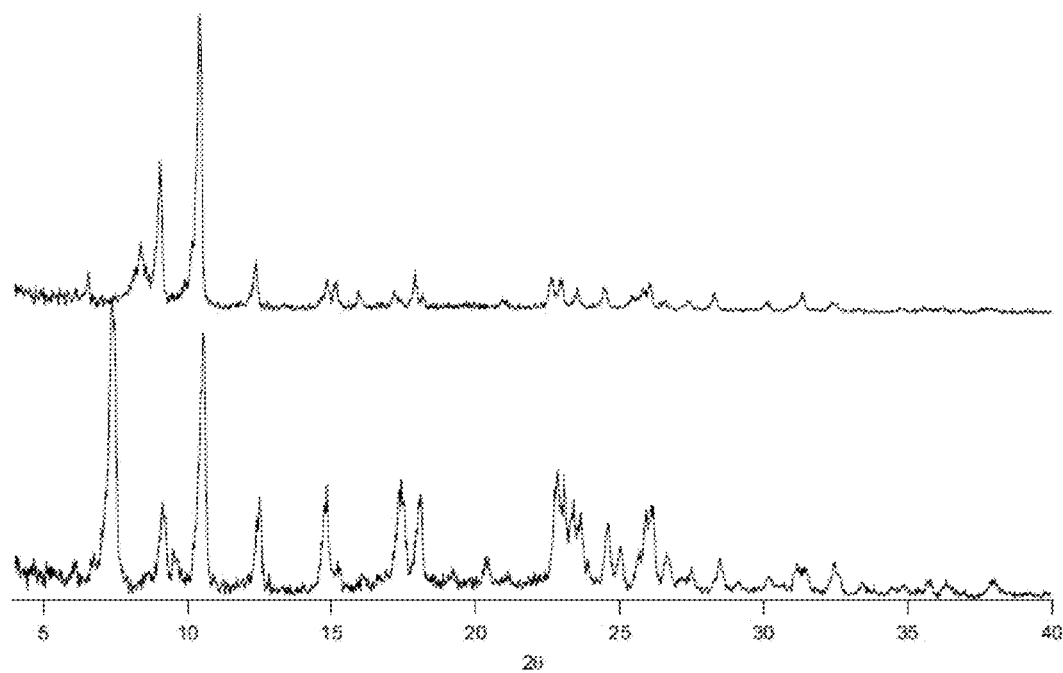
FIG. 32 shows representative powder X-ray diffraction (XRD) patterns for as-made STW+layered (lower) and calcined STW (upper), as described in Example 9.1

In certain other of these embodiments, the crystalline microporous solid having an HEU structure exhibit an XRD diffraction pattern the same as or consistent with that shown in FIG. 27, FIG. 28, or FIG. 29, reflective of the pore sizes comparable to or the same as those described in Table 1. In other embodiments, these crystalline microporous solids contain the doped metals or transition metals or oxides described herein. In some embodiments, the crystalline microporous solid having an HEU structure exhibits a $^{27}$Al MAS NMR spectrum that is the same as or consistent with the spectra of that shown in FIG. 30A or FIG. 30B. Additional characteristics of these materials may be found in the Examples.

Additional embodiments include those crystalline microporous solids having a topology as described as CIT-7, absent the occluded linked pair of quaternary imidazolium cations or imidazolium cations (i.e., where these organic materials have been removed) comprising either a pure silicate structure, or an structure comprising (a) silicon oxide and (b) aluminum oxide, boron oxide, gallium oxide, hafnium oxide, iron oxide, tin oxide, titanium oxide, indium oxide, vanadium oxide, zirconium oxide, or combination thereof, preferably aluminosilicates. The framework structure has been determined from a combination of rotation electron diffraction and synchrotron X-ray powder diffraction data, and may be defined in the following terms. The structure has 10 crystallographically unique tetrahedral atoms (T-atoms) in the unit cell, and can be described as an ordered arrangement of the $[4^25^46^2]$ mtw building unit and a previously unreported $[4^45^2]$ building unit. The framework contains a 2-dimensional pore system that is bounded by 10 T-atom rings (10-ring, 5.1 Å *6.2 Å opening) that are connected with oval 8-rings (2.9 Å*5.5 Å opening) through medium-sized cavities (7.9 Å) at the channel intersections.

Figure 23:
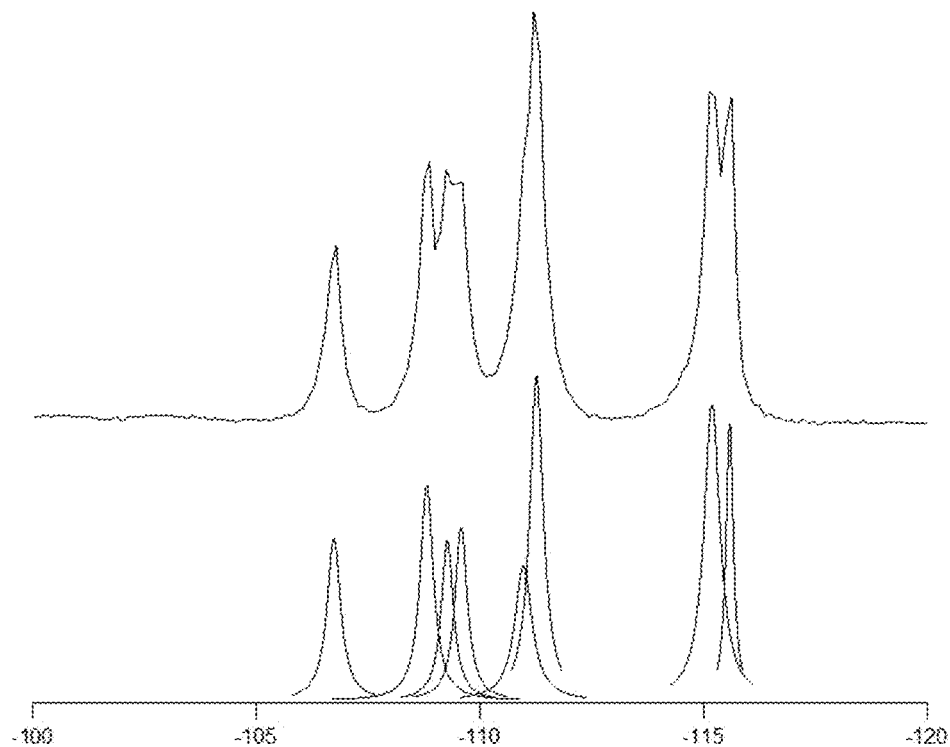
FIG. 23 shows an $^{29}Si$ MAS NMR spectrum of calcined pure silicate CIT-7 (upper) and the deconvolution of $^{29}Si$ MAS NMR spectrum of calcined pure silicate CIT-7 (lower).

In certain of these embodiments, the frameworks of these crystalline microporous CIT-7 solids contain oxides of silicon and at least aluminum. In other embodiments, these crystalline zeolites contain oxides of silicon and titanium. In certain of these embodiments, the solids exhibit an XRD diffraction pattern the same as or consistent with that shown in FIG. 11, FIG. 12, or FIG. 13A/B, reflective of the pore sizes comparable to or the same as those described in Table 1. In other embodiments, the crystalline silica CIT-7 solid exhibits a plurality of peak in the $^{29}$Si MAS spectrum, in some cases having chemical shifts of about 115.59, about 115.19, 111.2, 109.58, 109.27, 108.81, and about 106.735 ppm downfield of a peak corresponding to tetramethylsilane as shown in FIG. 23. Aluminosilicate versions of CIT-7 may exhibit $^{27}$Al MAS spectrum corresponding to FIG. 24. Other additional characteristics of these materials may be found in the Examples. In other embodiments, the crystalline silicate CIT-7 solid can be characterized by the crystallographic parameters substantially as described in Table 11. In still other embodiments, these crystalline microporous CIT-7 solids contain the doped metals or transition metals or oxides described herein.

Figure 26A:
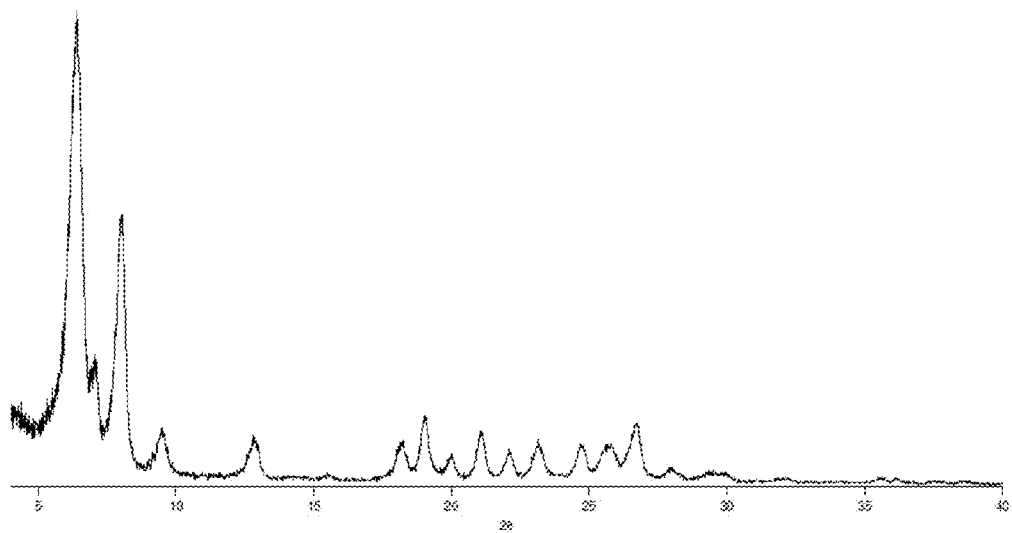
FIG. 26A and FIG. 26B show representative powder X-ray diffraction (XRD) patterns for calcined IWV, as described in Example 8.1.
Figure 26B:
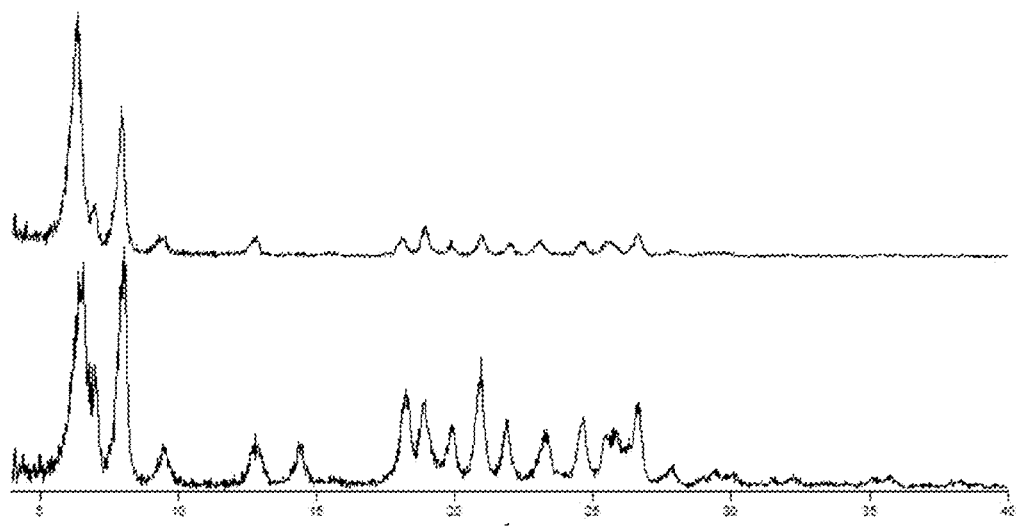

Additional embodiments include those crystalline microporous solids having an IWV topology, absent the occluded linked pair of quaternary imidazolium cations or imidazolium cation (i.e., where these organic materials have been removed) comprising either a pure silicate structure, or an structure comprising (a) silicon oxide and (b) aluminum oxide, boron oxide, gallium oxide, hafnium oxide, iron oxide, tin oxide, titanium oxide, indium oxide, vanadium oxide, zirconium oxide, or combination thereof, preferably aluminosilicates. Some embodiments provide that these structures exhibit a characteristic XRD diffraction pattern as shown in FIG. 26A or FIG. 26B. In some other embodiments, these IWV frameworks are pure silicates or aluminosilicates, having a Si:Al ratio of about 7.3:1, or in a range of from about 4:1 to about 5:1, from about 5:1 to about 10:1, from about 10:1 to about 15:1, from about 15:1 to about 20:1, from about 20:1 to about 25:1, from about 25:1 to about 30:1, from about 30:1 to about 50:1, from about 50:1 to about 100:1, from about 100:1 to about 250:1, from about 250:1 to infinity, or any combination of these ranges. Note that a Si:Al ratio of infinity (cc) corresponds to a silicate composition substantially free of Al.

The various crystalline structures described herein are conveniently described in terms of their characteristic XRD diffraction patterns. Certain embodiments include those structures exhibiting any one of the XRD patterns shown in any one of the Figures of this specification. Tables 2A and 2B provide tabulations of major peaks within each spectrum, and separate embodiments include those structures having at least the five major peaks of each spectrum, and optionally additional peaks, preferably in order of decreasing relative heights (intensities).

TABLE 2A

Representative XRD data for structures described in this specification

| Calcined pure silica RTH | | Calcined SiAl-RTH | | Calcined Si-CIT-7 | | Calcined topotactic HEU (CIT-8) | |
|---|---|---|---|---|---|---|---|
| 2-θ (deg) | Relative Height | 2-θ (deg) | Relative Height | 2-θ (deg) | Relative Height | 2-θ (deg) | Relative Height |
| 8.56 | 100.0 | 8.56 | 94.7 | 7.43 | 100.0 | 10.02 | 100 |
| 9.03 | 89.0 | 9.06 | 100.0 | 8.26 | 100.0 | 11.28 | 32.9 |
| 10.09 | 28.7 | 10.14 | 53.8 | 9.62 | 13.6 | 13.12 | 18.5 |
| 10.18 | 41.0 | 17.70 | 10.1 | 10.08 | 18.0 | 13.42 | 8.4 |
| 12.42 | 2.9 | 18.76 | 28.0 | 10.48 | 19.9 | 17.38 | 12.5 |
| 17.71 | 7.5 | 19.52 | 15.3 | 14.83 | 9.5 | 22.51 | 20.6 |
| 18.79 | 18.4 | 19.83 | 9.2 | 18.42 | 7.8 | 22.76 | 26.6 |
| 19.61 | 11.3 | 23.13 | 11.4 | 22.96 | 7.6 | 26.44 | 7.8 |
| 25.09 | 7.6 | 25.00 | 17.0 | 23.55 | 6.7 | 28.29 | 7.0 |
| 30.75 | 2.9 | 25.49 | 13.2 | 25.02 | 8.5 | 30.35 | 9.5 |

TABLE 2B

Representative XRD data for structures described in this specification

| As-made layered HEU (CIT-8P) | | Hydroxide HEU | | Calcined IWV (Si/Al = 15) | | Calcined STW | |
|---|---|---|---|---|---|---|---|
| 2-θ (deg) | Relative Height | 2-θ (deg) | Relative Height | 2-θ (deg) | Relative Height | 2-θ (deg) | Relative Height |
| 7.17 | 100.0 | 9.64 | 18.2 | 6.02 | 13.7 | 9.05 | 42.6 |
| 11.41 | 11.9 | 9.95 | 100.0 | 6.40 | 100.0 | 10.44 | 100.0 |
| 14.15 | 26.6 | 11.22 | 49.9 | 7.09 | 16.8 | 12.40 | 29.7 |
| 16.13 | 13.2 | 13.09 | 27.3 | 7.90 | 12.8 | 14.73 | 27.6 |
| 18.12 | 19.4 | 17.35 | 28.8 | 7.99 | 61.0 | 17.35 | 32.0 |
| 19.84 | 32.9 | 22.46 | 40.8 | 9.49 | 9.3 | 22.76 | 31.2 |
| 21.93 | 10.1 | 22.72 | 46.8 | 12.85 | 9.7 | 22.93 | 34.7 |
| 22.71 | 9.8 | 26.28 | 20.6 | 19.04 | 14.9 | 23.52 | 24.0 |
| 24.40 | 22.4 | 30.25 | 24.4 | 21.07 | 10.7 | 25.82 | 24.9 |
| 25.19 | 22.1 | 32.05 | 15.2 | 26.71 | 12.2 | 26.01 | 31.7 |

As described herein, the variation in the scattering angle (two theta) measurements, due to instrument error and to differences between individual samples, is estimated at ±0.15 degrees. The X-ray diffraction patterns shown in this application are considered representative of "as-synthesized" or "as-made" and calcined crystalline structures. Minor variations in the diffraction pattern can result from variations in the, e.g., silica-to-alumina mole ratio of the particular sample due to changes in lattice constants. In addition, sufficiently small crystals will affect the shape and intensity of peaks, leading to significant peak broadening. Calcination can also result in changes in the intensities of the peaks as compared to patterns of the "as-made" material, as well as minor shifts in the diffraction pattern. The crystalline solids produced by exchanging the metal or other cations present in the solids with various other cations ($NH_4^+$ and then calcining to produce $H^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments. Accordingly, the skilled artisan would expect that a description that structures having XRD patterns with peaks within such small variances shown in Tables 2A and 2B would still be considered within the scope of this invention.

The calcined crystalline microporous solids, calcined or doped or treated with the catalysts described herein may also be used as catalysts for a variety of chemical reactions, including hydrocracking hydrocarbons, dewaxing hydrocarbon feedstocks, isomerizing hydrocarbons including olefins, producing higher molecular weight hydrocarbons from lower molecular weight hydrocarbons, converting lower alcohols and other oxygenated hydrocarbons to produce liquid products including olefins, reducing the content of oxides of nitrogen contained in a gas stream in the presence of oxygen, and separating nitrogen from a nitrogen-containing gas mixture. In each case, the processes include contacting the respective feedstock with the catalyst under conditions sufficient to affect the transformation. Such transformations are known to those of ordinary skill in the art.

In various embodiments, the crystalline microporous solids mediate or catalyze an array of chemical transformation. As follows, each of the crystalline solid materials will have utility in at least each of the following applications, though it is believed that those having 8-MR structures (i.e., RTH, HEU, and CIT-7) will be especially useful in converting lower alcohols and other oxygenated hydrocarbons to produce liquid products including olefins, reducing the content of oxides of nitrogen contained in a gas stream in the presence of oxygen, and separating nitrogen from a nitrogen-containing gas mixture. Those compositions having 10-MR (i.e., HEU, CIT-7) or 12-MR (IWV) will be useful in hydrocarbon processing.

Some embodiments provide processes for converting hydrocarbons, each process comprising contacting a hydrocarbonaceous feed at hydrocarbon converting conditions with a catalyst comprising a crystalline microporous solid of this invention. The crystalline material may be predominantly in the hydrogen form, partially acidic or substantially free of acidity, depending on the process.

Other embodiments provide hydrocracking processes, each process comprising contacting a hydrocarbon feedstock under hydrocracking conditions with a catalyst comprising a crystalline microporous solid of this invention, preferably predominantly in the hydrogen form.

Still other embodiments provide processes for dewaxing hydrocarbon feedstocks, each process comprising contacting a hydrocarbon feedstock under dewaxing conditions with a catalyst comprising a crystalline microporous solid of this invention, preferably predominantly in the hydrogen form.

Yet other embodiments provide processes for improving the viscosity index of a dewaxed product of waxy hydrocarbon feeds, each process comprising contacting the waxy hydrocarbon feed under isomerization dewaxing conditions with a catalyst comprising a crystalline microporous solid of this invention, preferably predominantly in the hydrogen form.

Additional embodiments include those process for producing a C20+ lube oil from a C20+ olefin feed, each process comprising isomerizing said olefin feed under isomerization conditions over a catalyst comprising at least one transition metal catalyst and a crystalline microporous solid of this invention. The crystalline microporous solid may be predominantly in the hydrogen form.

Also included in the present invention are processes for isomerization dewaxing a raffinate, each process comprising contacting said raffinate in the presence of added hydrogen with a catalyst comprising at least one transition metal and a crystalline microporous solid of this invention. The raffinate may be bright stock, and the zeolite may be predominantly in the hydrogen form.

Also included in this invention is a process for increasing the octane of a hydrocarbon feedstock to produce a product having an increased aromatics content, each process comprising contacting a hydrocarbonaceous feedstock which comprises normal and slightly branched hydrocarbons having a boiling range above about 40° C. and less than about 200° C., under aromatic conversion conditions with a catalyst comprising a crystalline microporous solid of this invention made substantially free of acidity by neutralizing said zeolite with a basic metal. Also provided in this invention is such a process wherein the crystalline microporous solid contains a transition metal component.

Also provided by the present invention are catalytic cracking processes, each process comprising contacting a hydrocarbon feedstock in a reaction zone under catalytic cracking conditions in the absence of added hydrogen with a catalyst comprising a crystalline microporous solid of this invention, preferably predominantly in the hydrogen form. Also included in this invention is such a catalytic cracking process wherein the catalyst additionally comprises a large pore crystalline cracking component.

This invention further provides isomerization processes for isomerizing C4 to C7 hydrocarbons, each process comprising contacting a feed having normal and slightly branched C4 to C hydrocarbons under isomerizing conditions with a catalyst comprising a crystalline microporous solid of this invention, preferably predominantly in the hydrogen form. The crystalline microporous solid may be impregnated with at least one transition metal, preferably platinum. The catalyst may be calcined in a steam/air mixture at an elevated temperature after impregnation of the transition metal.

Also provided by the present invention are processes for alkylating an aromatic hydrocarbon, each process comprising contacting under alkylation conditions at least a molar excess of an aromatic hydrocarbon with a C2 to C20 olefin under at least partial liquid phase conditions and in the presence of a catalyst comprising a crystalline microporous solid of this invention, preferably predominantly in the hydrogen form. The olefin may be a C2 to C4 olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, or mixtures thereof.

Further provided in accordance with this invention are processes for transalkylating an aromatic hydrocarbon, each of which process comprises contacting under transalkylating conditions an aromatic hydrocarbon with a polyalkyl aromatic hydrocarbon under at least partial liquid phase conditions and in the presence of a catalyst comprising a crystalline microporous solid of this invention, preferably predominantly in the hydrogen form. The aromatic hydrocarbon and the polyalkyl aromatic hydrocarbon may be present in a molar ratio of from about 1:1 to about 25:1, respectively. The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention are processes to convert paraffins to aromatics, each of which process comprises contacting paraffins under conditions which cause paraffins to convert to aromatics with a catalyst comprising a crystalline microporous solid of this invention, said catalyst comprising gallium, zinc, or a compound of gallium or zinc.

In accordance with this invention there is also provided processes for isomerizing olefins, each process comprising contacting said olefin under conditions which cause isomerization of the olefin with a catalyst comprising a crystalline microporous solid of this invention.

Further provided in accordance with this invention are processes for isomerizing an isomerization feed, each process comprising an aromatic C8 stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the zeolite of this invention.

The present invention further provides processes for oligomerizing olefins, each process comprising contacting an olefin feed under oligomerization conditions with a catalyst comprising a crystalline microporous solid of this invention.

This invention also provides processes for converting lower alcohols and other oxygenated hydrocarbons, each process comprising contacting said lower alcohol (for example, methanol, ethanol, or propanol) or other oxygenated hydrocarbon with a catalyst comprising a crystalline microporous solid of this invention under conditions to produce liquid products. Compositions having the RTH topology are expected to be especially useful in this regard (see, e.g., Example 6).

Also provided by the present invention are processes for reducing oxides of nitrogen contained in a gas stream in the presence of oxygen wherein each process comprises contacting the gas stream with a crystalline microporous solid of this invention. The a crystalline microporous solid may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

Additional transformations considered within the scope of the present invention mediated by the crystalline materials of the present invention, but at least for those crystalline microporous solids of HEU, CIT-7, and IWV topologies, are those described in Table 13.

Specific conditions for each of these transformations are known to those of ordinary skill in the art. Exemplary conditions for such reactions/transformations may also be found in WO/1999/008961, which is incorporated by reference herein in its entirety for all purposes.

Depending upon the type of reaction which is catalyzed, the microporous solid may be predominantly in the hydrogen form, partially acidic or substantially free of acidity. As used herein, "predominantly in the hydrogen form" means that, after calcination, at least 80% of the cation sites are occupied by hydrogen ions and/or rare earth ions.

The following listing of embodiments is intended to complement, rather than displace or supersede, the previous descriptions.

Embodiment 1

A process comprising hydrothermally treating a composition comprising:
  (a) (i) at least one source of a silicon oxide, germanium oxide, or combination thereof; and optionally
    (ii) at least one source of aluminum oxide, boron oxide, gallium oxide, hafnium oxide, iron oxide, tin oxide, titanium oxide, indium oxide, vanadium oxide, zirconium oxide, or combination or mixture thereof; and
  (b) a linked pair of quaternary imidazolium cations of a structure:

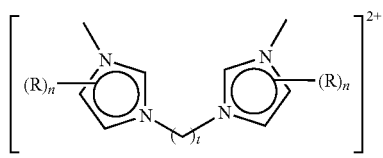

under conditions effective to crystallize a crystalline microporous solid;
  wherein t is 3, 4, 5, or 6, preferably 4 or 5; and
  R is independently methyl or ethyl, preferably methyl, and n is independently 1, 2, or 3; said linked pair of quaternary imidazolium cations having associated fluoride or hydroxide ions, preferably substantially free of other halide counterions, i.e., bromide, chloride, or iodide. Subsets of this embodiment include those where (a) comprises only at least one source of a silicon oxide, germanium oxide, or combination thereof, preferably only at least one source of a silicon oxide. Such methods are useful for producing crystalline silicate microporous solids having an RTH, HEU, CIT-7, or IWV topology. Additional subsets of this Embodiment include those where (a) comprises only at least one source of a silicon oxide and at least one source of aluminum oxide. Such methods are useful for producing at least crystalline aluminosilicate microporous solids having a CIT-7 or IWV topology.

Embodiment 2

The process of Embodiment 1, wherein the composition being hydrothermally treated comprises only (i) at least one source of silicon oxide or (ii) at least one form of silicon oxide and at least one source of aluminum oxide, for the preparation of crystalline microporous silicate and aluminosilicate solids, respectively.

Embodiment 3

The process of Embodiment 1 or 2, wherein the linked pair of quaternary imidazolium cations has a structure:

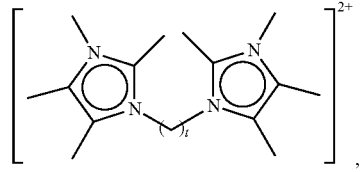

where t is 3, 4, or 5.

Embodiment 4

The process of any one of Embodiment 1 to 3, wherein the linked pair of quaternary imidazolium cations has a structure:

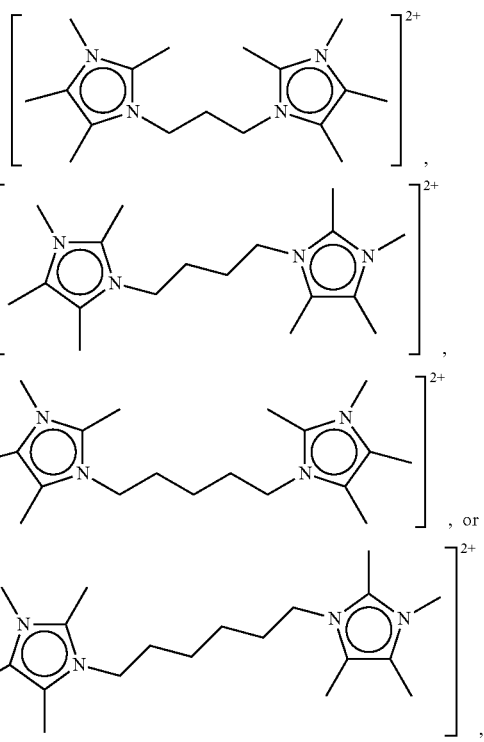

said linked pair of quaternary imidazolium cations, preferably having associated hydroxide ions.

Embodiment 5

A process comprising hydrothermally treating a composition comprising:
  (a) (i) at least one source of silicon oxide and optionally
    (ii) at least one source of aluminum oxide, boron oxide, gallium oxide, hafnium oxide, iron oxide, tin oxide, titanium oxide, indium oxide, vanadium oxide, zirconium oxide, or combination or mixture thereof;
  in the presence of an organic complex comprising
  (b) an imidazolium cation comprising methyl and ethyl groups and having a C/N+ ratio in a range of from about 6:1 to 10:1, preferably from 6:1, from 7:1, or from 8:1 to 9:1, more preferably 8:1, such that the imidazolium has, for example,
    (i) 3, 4, or 5 methyl groups or
    (ii) 2, 3, or 4 methyl groups and one ethyl group and
  (c) a hydroxide or fluoride anion, preferably substantially free of other halide counterions, i.e., bromide, chloride, or iodide;
  under conditions effective to crystallize a microporous solid. Processes for preparing silicates and aluminosilicates are considered within the scope of preferred embodiments. The crystalline microporous silicate or aluminosilicate solid may be one of an RTH, HEU, CIT-7 or IWV topology.

Embodiment 6

The process of Embodiment 5, comprising hydrothermally treating a composition comprising
- (a) (i) at least one source of a silicon oxide, germanium oxide, or combination thereof;
  - (ii) at least one source of aluminum oxide; and optionally
  - (iii) at least one source of boron oxide, gallium oxide, hafnium oxide, iron oxide, tin oxide, titanium oxide, indium oxide, vanadium oxide, zirconium oxide, or combination or mixture thereof; and
- (b) an imidazolium cation having (i) 3, 4, or 5 methyl groups or (ii) 2, 3, or 4 methyl groups and one ethyl group, and (iii) a hydroxide or fluoride anion, preferably substantially free of other halide counterions, i.e., bromide, chloride, or iodide;

under conditions effective to crystallize a microporous aluminosilicate solid. The crystalline microporous aluminosilicate solid may be one of an RTH, HEU, CIT-7, or IWV topology.

Embodiment 7

The process of Embodiment 5 or 6, wherein the imidazolium cation is described by a resonance form that is:

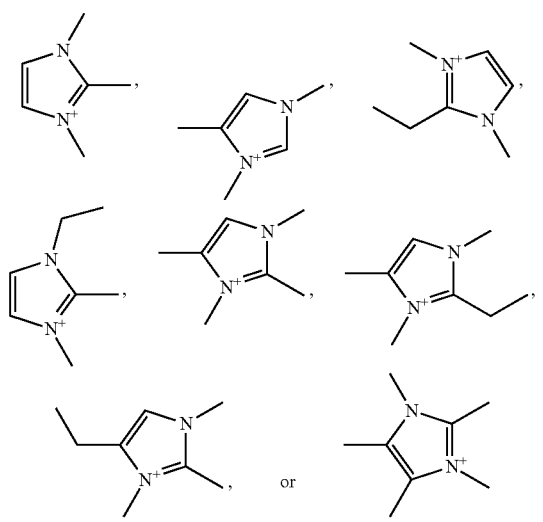

Embodiment 8

The process of any one of Embodiments 1 to 7, wherein the source of silicon oxide comprises an alkoxide, hydroxide, or oxide of silicon, or combination thereof. Exemplary compounds also include silicates, silica hydrogel, silicic acid, fumed silica, colloidal silica, tetra-alkyl orthosilicates, and silica hydroxides.

Embodiment 9

The process of any one of Embodiments 2 to 8, wherein the source of aluminum oxide comprises an alkoxide, hydroxide, or oxide of aluminum, or combination thereof. Additionally, the sources of alumina may also include other ligands as well, for example acetylacetonate, carboxylates, and oxalates; such compounds are well known as useful in hydrothermal or sol-gel syntheses.

Embodiment 10

The process of any one of Embodiments 2 to 9, wherein the source of boron oxide, gallium oxide, hafnium oxide, iron oxide, tin oxide, titanium oxide, indium oxide, vanadium oxide, zirconium oxide, or combination or mixture thereof comprises an alkoxide, hydroxide, oxide, or combination thereof of the corresponding metal.

Embodiment 11

The process of any one of claims 1 or 3 to 10, wherein the crystalline microporous solid independently exhibits an RTH, HEU, CIT-7, or IWV topology.

Embodiment 12

The process of any one of Embodiments 1 to 11, wherein the at least one source of silicon oxide comprise a silicon alkoxide, a silica, a sodium silicate, or a combination thereof.

Embodiment 13

The process of any one of Embodiments 2 to 12, wherein the at least one source of aluminum is an aluminum alkoxide, an aluminate (e.g., oxide, hydroxide, or mixed oxide/hydroxide), a sodium aluminate an aluminum siloxide, or a combination thereof.

Embodiment 14

The process of Embodiment 12, wherein the silicon alkoxide is of the formula $Si(OR)_4$, where R is an alkyl group of 1-6 carbon atoms.

Embodiment 15

The process of Embodiment 13, wherein the aluminum alkoxide is of the formula $Al(OR)_3$, where R is an alkyl group of 1-6 carbon atoms.

Embodiment 16

The process of any one of Embodiments 2 to 15, wherein the ratio of Si:Al in the composition is in a range of from about 5:1 to about 250:1. Subset Embodiments include those wherein the Si:Al ratios ranges from about 4:1 to about 5:1, from about 5:1 to about 10:1, from about 10:1 to about 15:1, from about 15:1 to about 20:1, from about 20:1 to about 25:1, from about 25:1 to about 30:1, from about 30:1 to about 50:1, from about 50:1 to about 100:1, from about 100:1 to about 250:1, from about 250:1 to infinity, or a combination of two or more of these ranges.

Embodiment 17

The process of any one of Embodiments 1 to 16, wherein the composition further comprises aqueous HF.

Embodiment 18

The process of any one of Embodiments 1 to 16, wherein the composition further comprises aqueous hydroxide, for example sodium hydroxide, potassium hydroxide, lithium hydroxide, cesium hydroxide, rubidium hydroxide, barium hydroxide, calcium hydroxide, or magnesium hydroxide.

Embodiment 19

The process of Embodiment 17, wherein the ratio of imidazolium cation:Si is in a range of from about 0.0.2:1 to about 1:1, preferably about 0.5:1.

Embodiment 20

The process of Embodiment 18, wherein the ratio of imidazolium cation:Si is in a range of from about 0.05 to about 1:1, preferably about 0.2:1.

Embodiment 21

The process of Embodiment 17 or 19, wherein the ratio of water:Si is in a range of from about 2:1 to about 20:1, preferably in a range of from about 4:1 to about 10:1.

Embodiment 22

The process of Embodiments 18 or 20, wherein the ratio of water:Si is in a range of from about 2:1 to about 40:1, preferably in a range of from about 15-20:1.

Embodiment 23

The process of any one of Embodiments 1 to 22, wherein the hydrothermally treating is done at a temperature in a range of from about 100° C. to about 200° C., preferably about 140° C. to about 180° or from about 160° C. to about 180° C., for a time effective for crystallizing the crystalline microporous solid.

Embodiment 24

The process of any one of Embodiments 1 to 23, further comprising isolating a crystalline microporous solid.

Embodiment 25

The process of Embodiment 24, wherein the crystalline microporous solid contains a portion of the imidazolium cation or linked pair of quaternary imidazolium cations used in its preparation.

Embodiment 26

The process of Embodiment 20 or 23, further comprising calcining the crystalline microporous solid at a temperature in a range of from about 25° C. to about 850° C. under oxidative (e.g., air, oxygen, or ozone) or inert atmosphere. When a strongly oxidizing atmosphere is uses (e.g., ozone), the temperature is generally in a range from about 25° C. to about 200° C. Otherwise, the calcining is done at at least one temperature in at least one temperature range of from about 350° C. to about 450° C., from about 450° C. to about 550° C., from about 550° C. to about 650° C., from about 650° C. to about 750° C., from about 750° C. to about 850° C.

Embodiment 27

The process of Embodiment 26, further comprising treating the calcined material with an aqueous ammonium salt.

Embodiment 28

The process of Embodiment 26, further comprising treating at least some pores of the microporous solid with at least one type of transition metal or transition metal oxide

Embodiment 29

A composition comprising:
(a) at least one source of a silicon oxide, germanium oxide, or combination thereof;
(b) a linked pair of quaternary imidazolium cations of a structure:

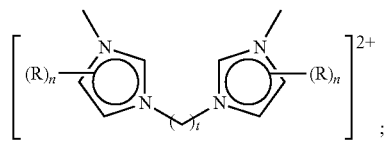

wherein t is 3, 4, 5, or 6; and
R is independently methyl or ethyl, and n is independently 1, 2, or 3;
said linked pair of quaternary imidazolium cations having associated fluoride or hydroxide ions; and
(c) optionally a compositionally consistent crystalline microporous silicate solid. In some of these embodiments, a portion of the linked pair of imidazolium cations is occluded in the pores of the crystals Preferably, the linked pair of quaternary imidazolium cations has a structure of:

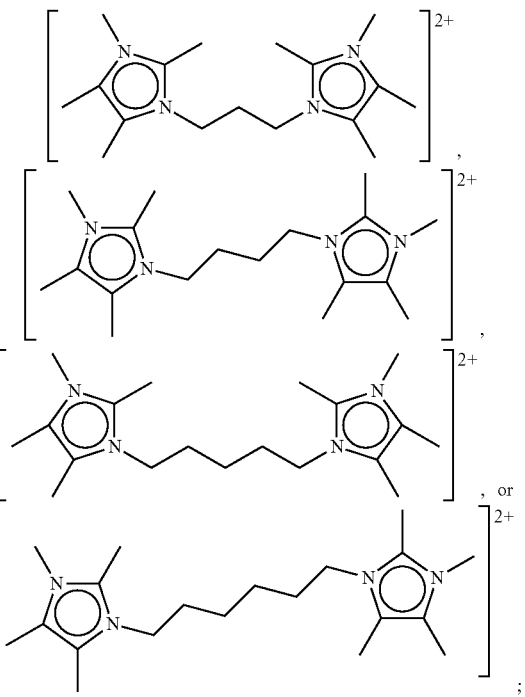

and said linked pair of quaternary imidazolium cations having associated hydroxide ions.

Embodiment 30

The composition of claim 29, further comprising at least one source of aluminum oxide, boron oxide, gallium oxide, hafnium oxide, iron oxide, tin oxide, titanium oxide, indium oxide, vanadium oxide, zirconium oxide, or combination or mixture thereof. A subset of this embodiment includes that where the at least one source of aluminum oxide is necessarily present.

Embodiment 31

A composition comprising:
(a) at least one source of a silicon oxide, germanium oxide, or combination thereof; and optionally
(b) a source of aluminum oxide; and
(c) an imidazolium cation comprising methyl and ethyl groups and having a C/N+ ratio in a range of from about 6:1 to 10:1, preferably from 6:1, from 7:1, or from 8:1 to 9:1, more preferably 8:1, such that the imidazolium cation has, for example,
  (i) 3, 4, or 5 methyl groups or
  (ii) 2, 3, or 4 methyl groups and one ethyl group and
(c) a hydroxide or fluoride anion, preferably substantially free of other halide counterions, i.e., bromide, chloride, or iodide; and
(d) optionally a compositionally consistent crystalline microporous aluminosilicate solid. This compositionally crystalline microporous aluminosilicate solid may independently have an RTH, HEU, or CIT-17 topology, the specific nature of which depends on the target crystalline microporous composition. In some of these embodiments, a portion of the imidazolium cation is occluded in the pores of the crystals. Additional subsets of this Embodiment include those where only at least one source of a silicon oxide is present and those where at least one source of silicon oxide and at least one source of aluminum oxide are present.

Embodiment 32

The composition of Embodiment 31, further comprising a source of boron oxide, gallium oxide, hafnium oxide, iron oxide, tin oxide, titanium oxide, indium oxide, vanadium oxide, zirconium oxide, or combination or mixture thereof.

Embodiment 33

The composition of Embodiment 31 or 32, wherein the imidazolium cation is described by a resonance form that is:

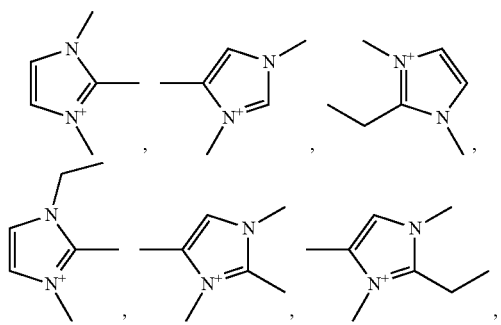

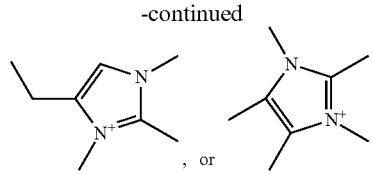

, or

Embodiment 34

The composition of any one of Embodiments 29 to 33, wherein the source of silicon oxide comprises an alkoxide, hydroxide, or oxide of silicon, or combination thereof.

Embodiment 35

The composition of any one of Embodiments 30 to 34 wherein the source of aluminum oxide comprises an alkoxide, hydroxide, or oxide of aluminum, an aluminum siloxide, or combination thereof.

Embodiment 36

The composition of any one of Embodiments 29 to 35, wherein the source of silicon comprise a silicon alkoxide having an empirical formula of $Si(OR)_4$, where R is an alkyl group of 1-6 carbon atoms.

Embodiment 37

The composition of any one of Embodiments 30 to 36, wherein the source of aluminum comprise an aluminum alkoxide having an empirical formula of $Al(OR)_3$, where R is an alkyl group of 1-6 carbon atoms.

Embodiment 38

The composition of any one of Embodiments 29 to 37, wherein the composition further comprises aqueous HF.

Embodiment 39

The composition of any one of Embodiments 29 to 37, wherein the composition further comprises aqueous hydroxide.

Embodiment 40

The composition of Embodiment 38, wherein the ratio of imidazolium cation:Si is in a range of from about 0.2:1 to about 1:1, preferably about 0.5:1.

Embodiment 41

The composition of Embodiment 39, wherein the ratio of imidazolium cation:Si is in a range of from about 0.05 to about 1:1, preferably about 0.2:1.

Embodiment 42

The composition of Embodiment 38 or 40, wherein the ratio of water:Si is in a range of from about 2:1 to about 20:1, preferably 4:1 to 10:1.

Embodiment 43

The process of Embodiments 39 or 41, wherein the ratio of water:Si is in a range of from about 2:1 to about 40:1, preferably in a range of from about 15:1 to 20:1

Embodiment 44

The composition of any one of Embodiments 30 to 43 wherein the ratio of Si:Al in the composition is in a range of from about 5:1 to about 250:1.

Embodiment 45

The composition of any one of Embodiments 29 to 44, which is a gel.

Embodiment 46

The composition of any one of Embodiments 29 to 45, further independently comprising a crystalline microporous solid having RTH, HEU, CIT-7 or IWV topology.

Embodiment 47

The composition Embodiment 46, wherein the microporous solid having RTH, HEU, CIT-7, or IWV topology has a Si:Al ratio in a range of at least 5. Note that an Si:Al ratio of infinity (∞) corresponds to a silicate composition substantially free of Al.

Embodiment 48

The composition of Embodiment 46 or 47, that is substantially free of other crystalline materials.

Embodiment 49

A crystalline microporous solid prepared by the process of any one of Embodiments 1 to 28. A subset of this Embodiment includes those calcined crystalline microporous solid, prepared by a process of any one of Embodiments 26 to 28. Another subset of this Embodiment includes those compositions, whether prepared by or independent of one of these processes, where the ratio of Si:Al is in a range of from about 4:1 to 5:1, from about 5:1 to about 7.3:1, from about 7.3:1 to about 10:1, from about 10:1 to about 12.3:1, from about 12.3:1 to about 15:1, from about 15:1 to about 17.3:1, from about 17.3:1 to about 20:1, from about 20:1 to about 25:1, from about 25:1 to about 50:1, from about 50:1 to about 75:1, from about 75:1 to about 100:1, from about 100:1 to about 250:1, from about 250:1 to ∞:1, or a combination of two or more of these ranges, whether as-synthesized, calcined, doped, or otherwise modified.

Embodiment 50

The crystalline solid of Embodiment 49, the crystalline microporous solid independently having an RTH, HEU, CIT-7 or IWV topology.

Embodiment 51

A crystalline microporous solid of claim 49 or 50 having pores at least some of which are occluded with a linked pair of quaternary imidazolium cations of a structure:

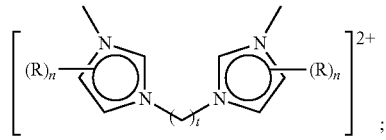

wherein t is 3, 4, 5, or 6, preferably 4 or 5;
R is independently methyl or ethyl, and n is independently 1, 2, or 3; or any of the more specific linked pair of quaternary imidazolium cations described herein. Depending on the specific conditions used to prepare the solid, the crystalline solid has an RTH, HEU, CIT-7, or IWV topology, as described herein.

Embodiment 52

A crystalline microporous solid of claim 49 or 50 having pores, at least some of which are occluded with an organic complex comprising (a) an imidazolium cation comprising methyl and ethyl groups and having a C/N+ ratio in a range of from about 6:1 to 10:1, preferably from 6:1, from 7:1, or from 8:1 to 9:1, more preferably 8:1, and where the crystalline microporous solid has an RTH, HEU, CIT-7, or IWV topology, depending on the specific conditions used to prepare the solid as described herein.

Embodiment 53

The crystalline microporous solid of Embodiment 51 or 52, wherein the occluded imidazolium cation or linked pair of quaternary imidazolium cations is described by a resonance form that is:

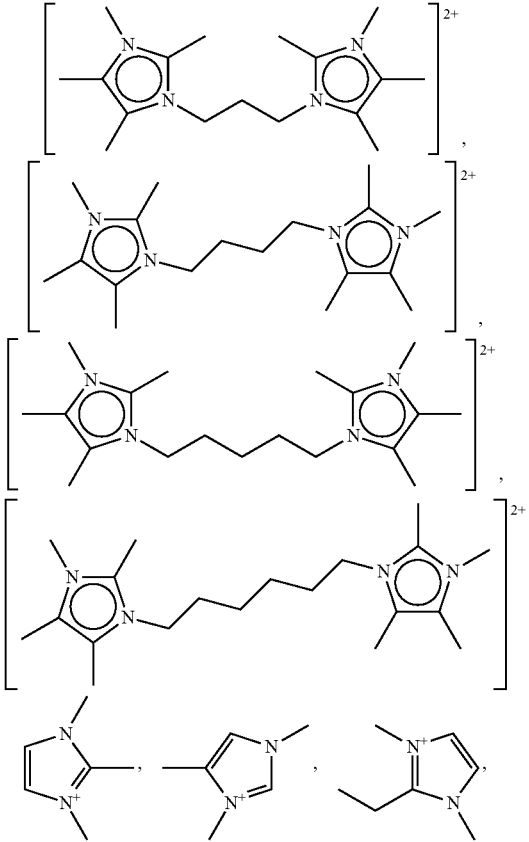

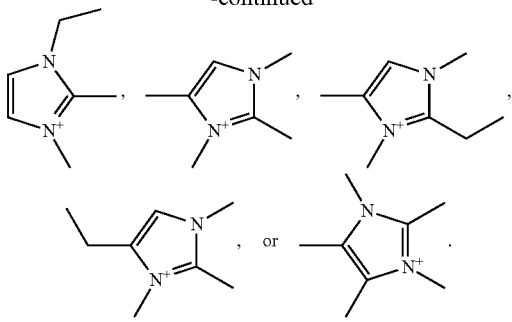

Embodiment 54

The crystalline microporous solid of any one of Embodiments 51 to 53, wherein the crystalline solid is a microporous silicate solid.

Embodiment 55

The crystalline microporous solid of any one of Embodiments 51 or 54, wherein the crystalline solid is a microporous aluminosilicate solid having a ratio of Si:Al in a range of from about 5:1 to about 250:1. Subsets of this Embodiments include those where the range is from about 4:1 to about 5:1, from about 5:1 to about 10:1, from about 10:1 to about 15:1, from about 15:1 to about 20:1, from about 20:1 to about 25:1, from about 25:1 to about 30:1, from about 30:1 to about 50:1, from about 50:1 to about 100:1, from about 100:1 to about 250:1, from about 250:1 to infinity, or a combination of two or more of these ranges.

Embodiment 56

A crystalline microporous solid having an RTH structure comprising (a) silicon oxide, germanium oxide, or combination thereof and (b) aluminum oxide, boron oxide, gallium oxide, hafnium oxide, iron oxide, tin oxide, titanium oxide, indium oxide, vanadium oxide, or zirconium oxide, wherein the molar ratio of (a) to (b) is less than 20, preferably in a range of from about 5 to about 10, from about 10 to about 15, from about 15 to less than 20, or a combination of two or more of these ranges, more preferably about 15. One subset of this embodiment is one where the crystalline microporous solid is an aluminosilicate, where the ratio of (a) to (b) refers to the ratio of Si to Al.

Embodiment 57

A calcined crystalline microporous solid having an RTH structure comprising (a) silicon oxide, germanium oxide, or combination thereof and (b) aluminum oxide, boron oxide, gallium oxide, hafnium oxide, iron oxide, tin oxide, titanium oxide, indium oxide, vanadium oxide, or zirconium oxide wherein the molar ratio of (a) to (b) is in a range of from about 5 to about 10, from about 10 to about 15, from about 15 to less than 20, or a combination of two or more of these ranges, more preferably about 15. One subset of this embodiment is one where the crystalline microporous solid is an aluminosilicate.

Embodiment 58

An as-synthesized or calcined crystalline microporous solid having an HEU framework topology comprising (a) silicon oxide, germanium oxide, or combination thereof and (b) aluminum oxide, boron oxide, gallium oxide, hafnium oxide, iron oxide, tin oxide, titanium oxide, indium oxide, vanadium oxide, zirconium oxide, or combination thereof, wherein the molar ratio of (a) to (b) is in a range of from about 4 to about 5, from about 5 to about 7.3, from about 7.3 to about 10, from about 10 to about 12.3, from about 12.3 to about 15, from about 15 to about 17.3, from about 17.3 to about 20, or a combination of two or more of these ranges. One subset of this embodiment is one where the crystalline microporous solid is an aluminosilicate, where the ratio of (a) to (b) refers to the ratio of Si to Al.

Embodiment 59

Figure 11:
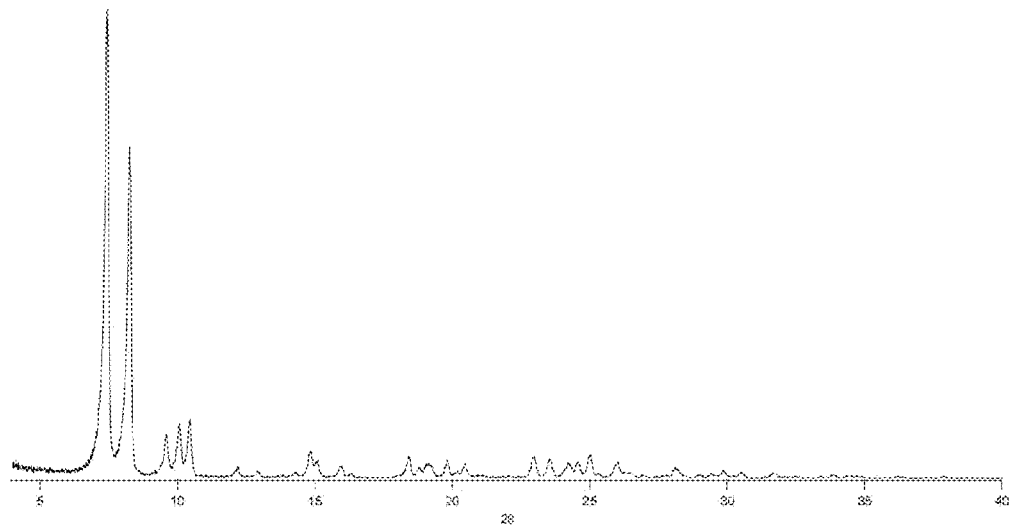
FIG. 11 shows representative powder X-ray diffraction (XRD) pattern for calcined pure-silica CIT-7 produced in fluoride media using 3,3'-(butane-1,4-diyl)bis(1,2,4,5-tetramethyl-1H-imidazol-3-ium) cation. See Example 8.1.
Figure 12:
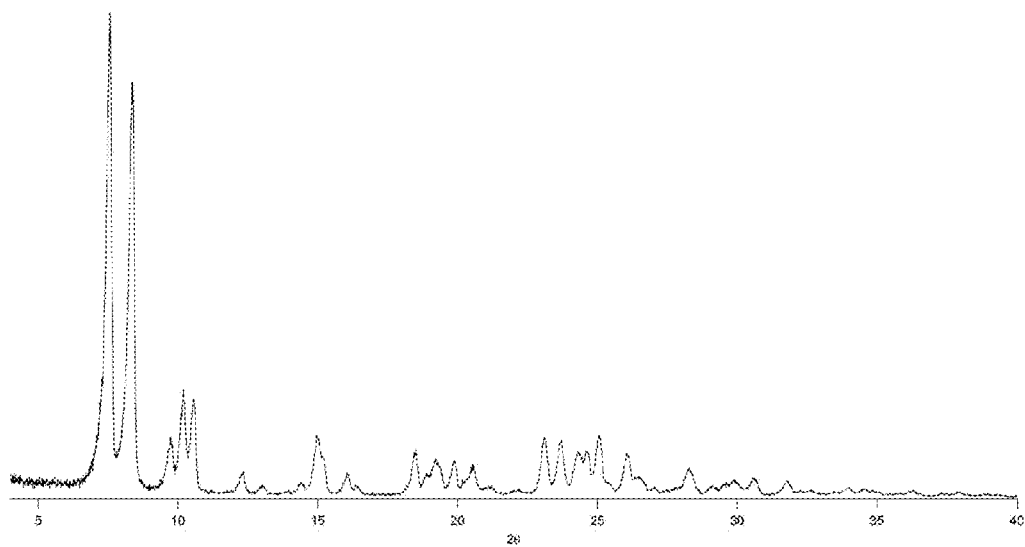
FIG. 12 shows representative powder X-ray diffraction (XRD) pattern for calcined aluminosilicate CIT-7 produced in fluoride media with the 3,3'-(butane-1,4-diyl)bis(1,2,4,5-tetramethyl-1H-imidazol-3-ium) cation and gel Si/Al=50, as described in Example 8.
Figure 13A:
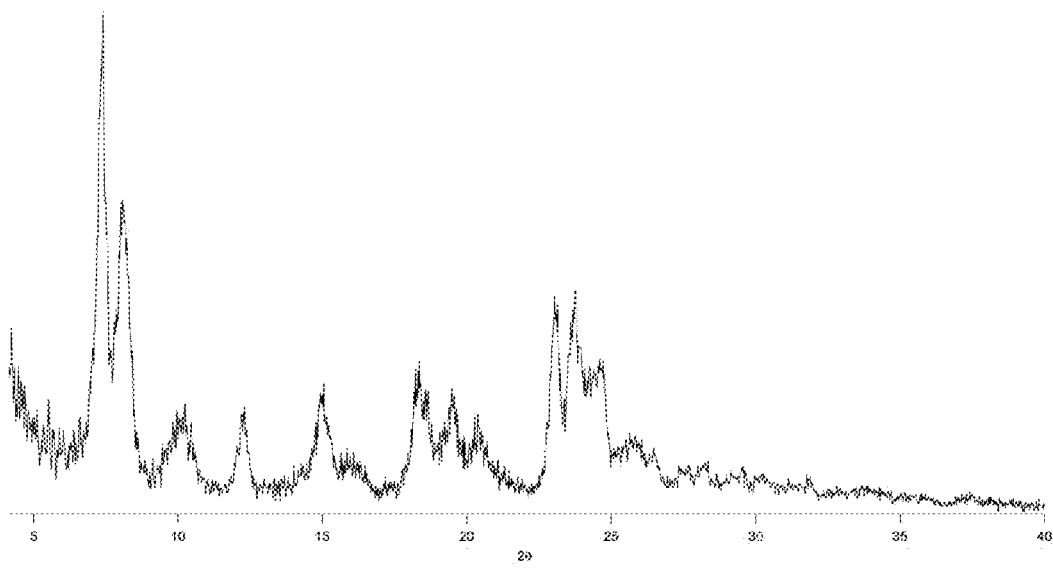
FIGS. 13A and 13B show representative powder X-ray diffraction (XRD) patterns for as-made CIT-7 (FIG. 13A) and calcined CIT-7 (FIG. 13B) produced in hydroxide media with the 3,3'-(butane-1,4-diyl)bis(1,2,4,5-tetramethyl-1H-imidazol-3-ium) cation and gel Si/Al=15, as described in Example 8.1.

A calcined crystalline microporous solid comprising (a) silicon oxide, germanium oxide, or combination thereof and optionally (b) aluminum oxide, boron oxide, gallium oxide, hafnium oxide, iron oxide, tin oxide, titanium oxide, indium oxide, vanadium oxide, zirconium oxide, or combination thereof, having 8-MR and 10-MR pore structures and at least one of the following characteristics:

(a) the solid exhibits an $^{29}$Si MAS spectrum having a plurality of chemical shifts of about 115.59, about 115.19, 111.2, 109.58, 109.27, 108.81, and about 106.735 ppm downfield of a peak corresponding to and external standard of tetramethylsilane; or (c) the solid exhibits an XRD diffraction pattern the same as or consistent with those shown in FIG. 11, FIG. 12, or FIG. 13A/B. Subsets of this embodiment include those where the crystalline microporous solid is a silicate, aluminosilicate, or a titanosilicate.

Embodiment 60

Figure 18:
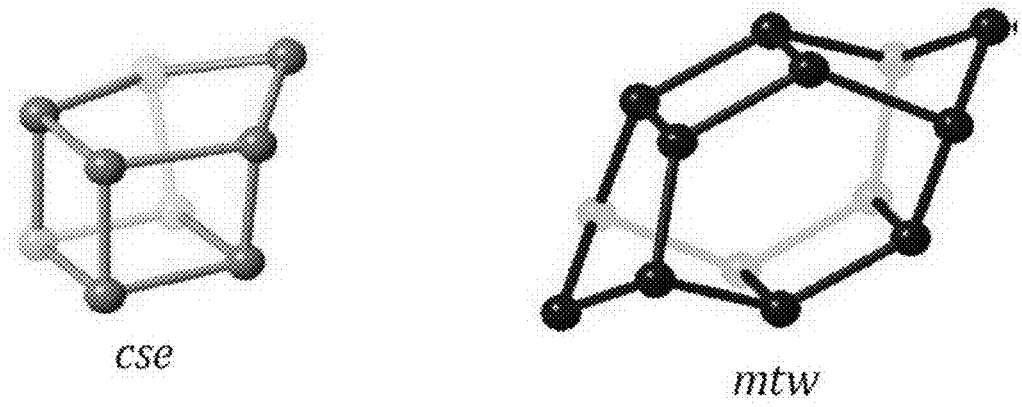
FIG. 18 shows the secondary building units found in CIT-7.
Figure 19:
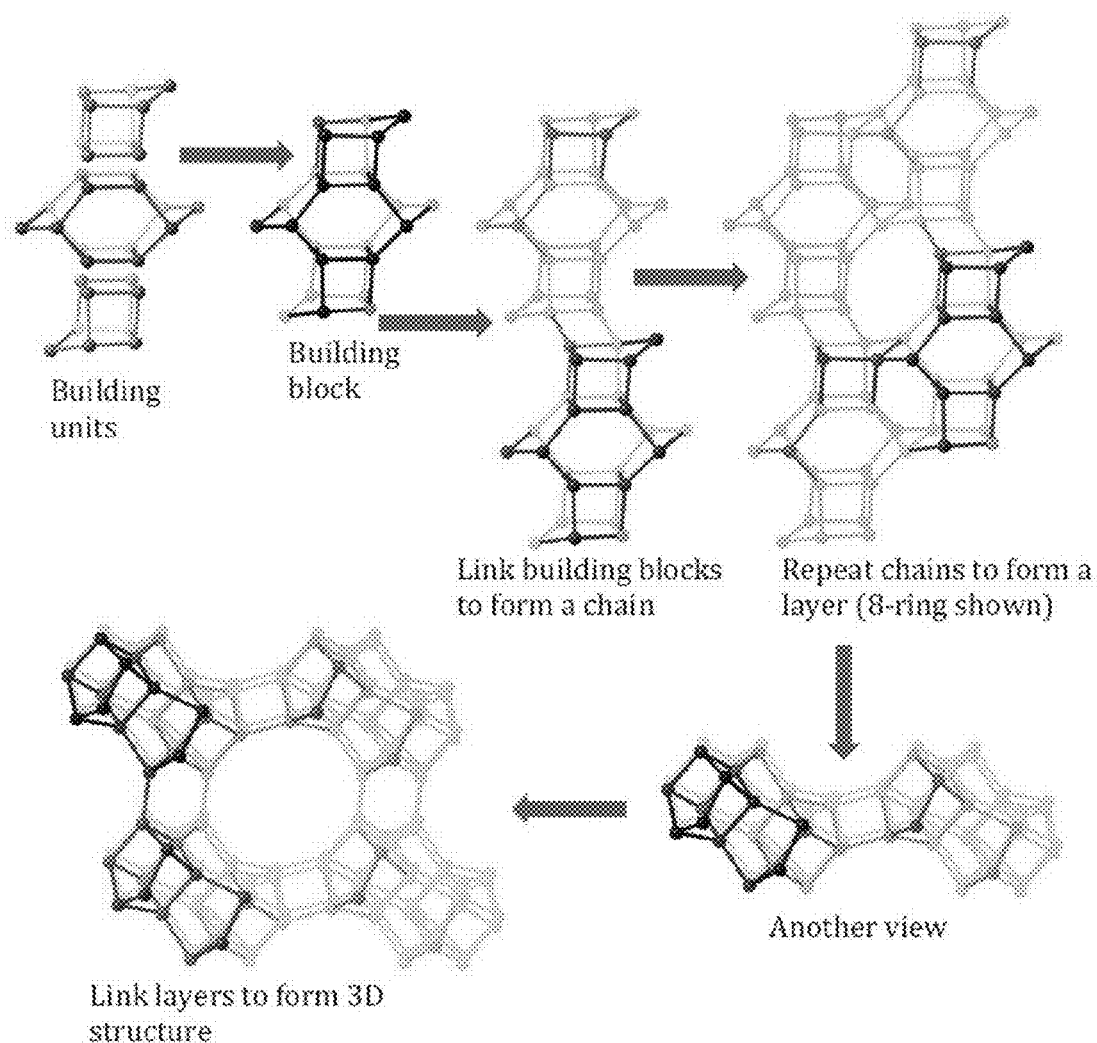
FIG. 19 shows an assembly of the CIT-7 framework from secondary building units. The mtw and the new [$4^45^2$] (cse) composite building units assembled to form a repeating building unit. The connection of the building units forms a chain. The arrangement of the chain forms a layer with distorted 8-rings. Connection of the layers forms 10-ring channels that are intersected with the 8-ring channels.

A calcined crystalline microporous solid comprising (a) silicon oxide, germanium oxide, or combination thereof and optionally (b) aluminum oxide, boron oxide, gallium oxide, hafnium oxide, iron oxide, tin oxide, titanium oxide, indium oxide, vanadium oxide, zirconium oxide, or combination thereof, having cse and mtw building blocks (as shown in FIG. 18 or FIG. 19). Subsets of this embodiment include those where the crystalline microporous solid is a silicate, aluminosilicate, or a titanosilicate.

Embodiment 61

A calcined microporous solid having a framework substantially as described in Table 11, or an aluminosilicate or titanosilicate version thereof.

Embodiment 62

A calcined microporous solid having an IWV framework and exhibiting an XRD diffraction pattern the same as or consistent with those shown in FIG. 26A or FIG. 26B.

Embodiment 63

The calcined microporous solid of Embodiment 62, having an Si:Al ratio in a range of from about 4:1 to about 5:1, from about 5:1 to about 10:1, from about 10:1 to about 15:1, from about 15:1 to about 20:1, from about 20:1 to about 25:1, from about 25:1 to about 30:1, from about 30:1 to about 50:1, from about 50:1 to about 100:1, from about 100:1 to about 250:1, from about 250:1 to infinity, or a combination of two or more of these ranges. Note that an Si:Al ratio of infinity (∞) corresponds to a silicate composition substantially free of Al.

Embodiment 64

The calcined compositions of any one of Embodiments 56 to 61, wherein the calcined composition is predominantly in the hydrogen form.

Embodiment 65

Figure 2:
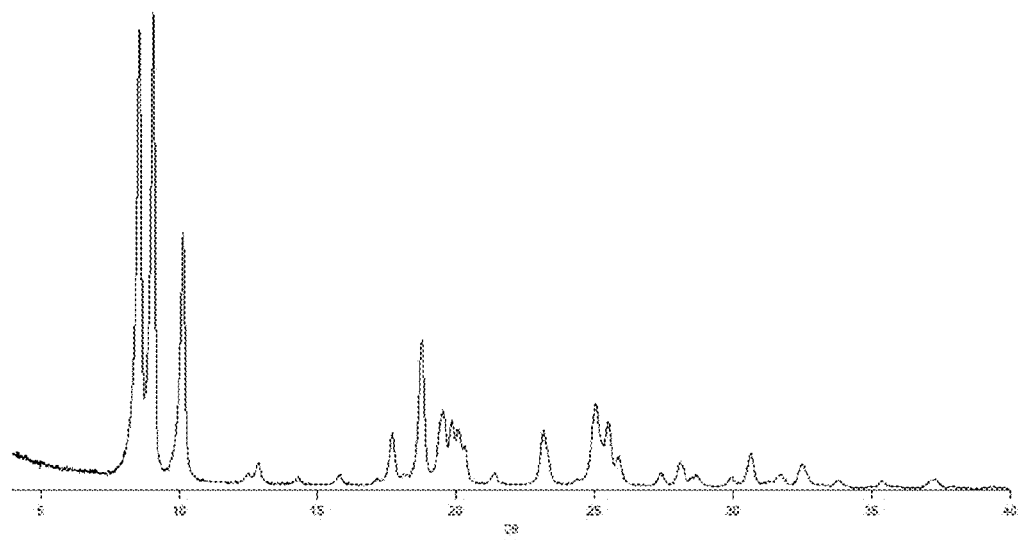
FIG. 2 shows representative powder X-ray diffraction (XRD) patterns for calcined aluminosilicate RTH prepared in hydroxide media (sample H4), as described in Example 4.
Figure 3:
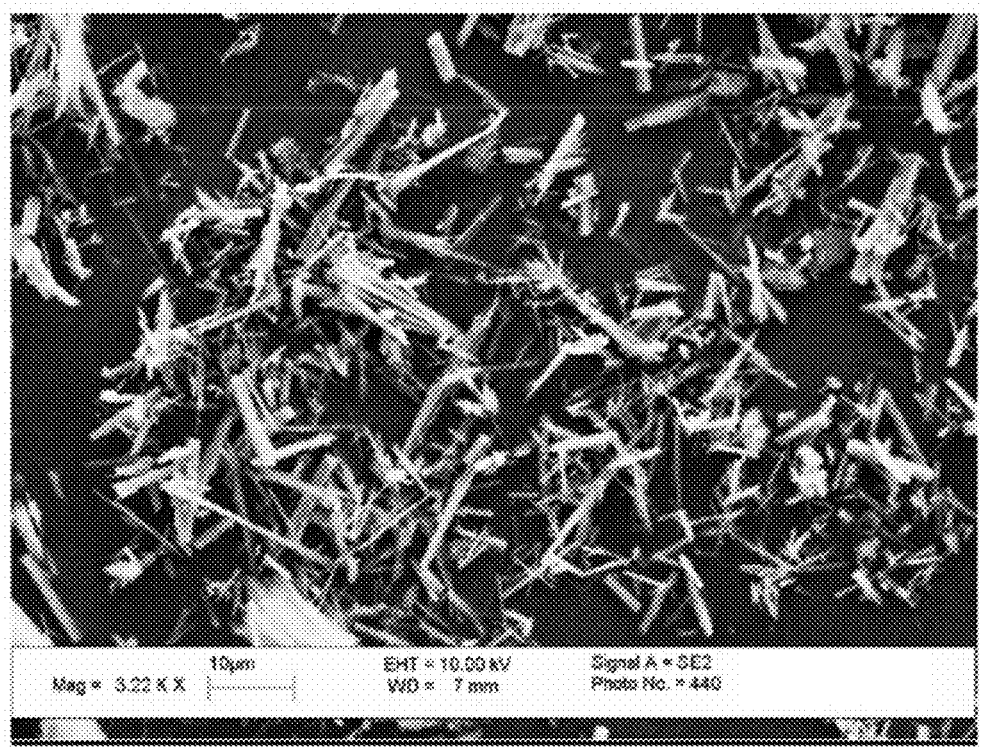
Figure 9A:
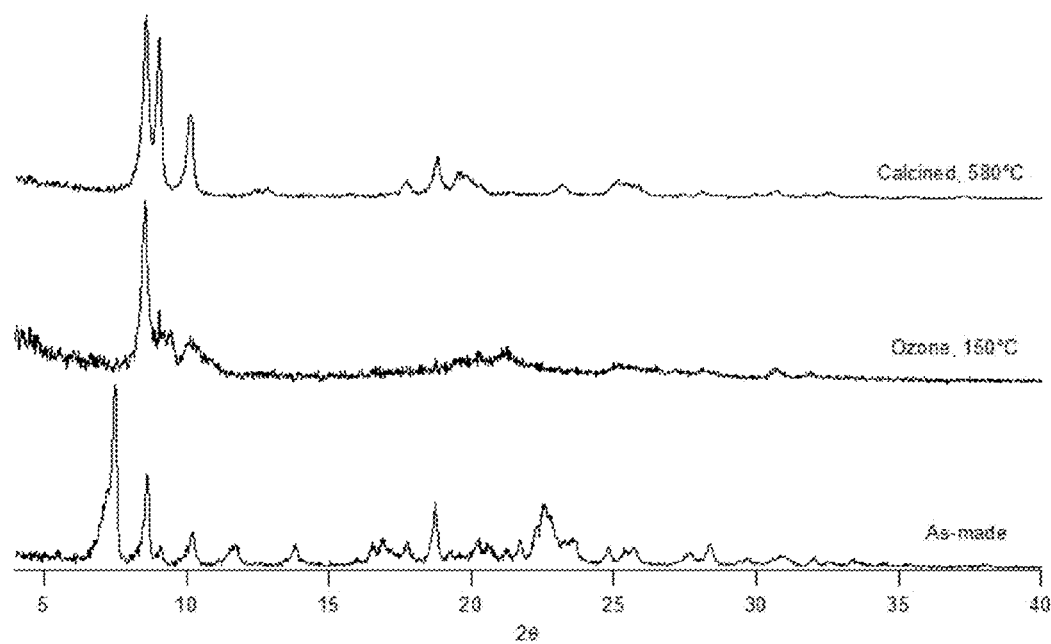
FIGS. 9A and 9B shows representative powder X-ray diffraction (XRD) patterns for calcined pure silicate RTH prepared in fluoride. The patterns are for the as-made material (FIG. 9A, lower), material treated with ozone at 150° C. to remove the organic (FIG. 9A, middle) and calcined material (FIG. 9A, upper and FIG. 9B).

A crystalline microporous composition comprising (a) silicon oxide, germanium oxide, or combination thereof and (b) aluminum oxide, boron oxide, gallium oxide, hathium oxide, iron oxide, tin oxide, titanium oxide, indium oxide, vanadium oxide, zirconium oxide, or combination thereof, and exhibiting a powder X-ray diffraction pattern of any one of FIG. 2, FIG. 9A or B, FIG. 10, FIG. 11, FIG. 12, FIG. 13A/B, FIG. 26A or B, FIG. 27, FIG. 28, FIG. 29, FIG. 31, or FIG. 32.

Embodiment 66

A crystalline microporous composition comprising (a) silicon oxide, germanium oxide, or combination thereof and (b) aluminum oxide, boron oxide, gallium oxide, hathium oxide, iron oxide, tin oxide, titanium oxide, indium oxide, vanadium oxide, zirconium oxide, or combination thereof, and having at least the five major peaks, and optionally additional peaks, preferably in order of decreasing relative intensities, in the powder X-ray diffraction pattern, substantially as provided in Tables 2A or 2B.

Embodiment 67

A process comprising carbonylating DME with CO at low temperatures, reducing NOx with methane, cracking, dehydrogenating, converting paraffins to aromatics, MTO, isomerizing xylenes, disproportionating toluene, alkylating aromatic hydrocarbons, oligomerizing alkenes, aminating lower alcohols (including methanol), separating and sorbing lower alkanes (e.g., C3-C6 alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream in the presence of oxygen, or separating nitrogen from a nitrogen-containing gas mixture by contacting the respective feedstock with the crystalline microporous solid of any one of Embodiments 49 or 56 to 65 under conditions sufficient to affect the named transformation.

Embodiment 68

A method comprising contacting methanol with a composition of any one of claims Embodiments 49 or 56 to 65 under conditions sufficient to convert the methanol to at least one type of olefin.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric.

Example 1

Materials and Methods

Unless otherwise noted all reagents were purchased from Sigma-Aldrich and were used as received. Hydroxide ion exchanges were performed using Supelco Dowex Monosphere 550A UPW hydroxide exchange resin with an exchange capacity of 1.1 meq/mL. Titrations were performed using a Mettler-Toledo DL22 autotitrator using 0.01 M HCl as the titrant. All liquid NMR spectra were recorded with a 400 MHz Varian Spectrometer.

The $^{13}C$ CP-MAS NMR spectra were recorded using a Bruker Avance 200 MHz spectrometer with a 7 mm rotor at a spinning rate of 4 kHz and were conducted in a 4.7 T magnetic field, corresponding to Larmor frequencies of 200 MHz and 50.29 MHz for $^1H$ and $^{13}C$ respectively. The $^{13}C$ spectra are referenced to adamantane as a secondary external standard relative to tetramethylsilane. $^{29}Si$ and $^{19}F$ NMR were performed using a Bruker DSX-500 spectrometer (11.7 T) and a Bruker 4 mm MAS probe. The spectral frequencies were 500.2 MHz, 99.4 MHz, and 470.7 MHz for $^1H$, $^{29}Si$, and $^{19}F$ nuclei, respectively, and spectra were referenced to external standards as follows: tetramethylsilane (TMS) for $^1H$ and $^{29}Si$, and $CFCl_3$ for $^{19}F$. The $^{27}Al$ MAS NMR were recorded using a Bruker AM 300 MHz spectrometer with a 4 mm rotor at a spinning rate of 8 kHz, and were conducted in a 7.0 T magnetic field corresponding to a Larmor frequency of 78.172 MHz. The $^{27}Al$ spectra are referenced to 1.1 M $Al(NO_3)_3$ as an external standard.

Thermogravimetric analysis measurements were performed with a Netzsch STA 449C Jupiter. Samples were heated in air to 900° C. at a rate of 1° C./min. All Argon adsorption isotherms were performed at 87.45 K using a Quantachrome Autosorb iQ and were conducted using a quasi-equilibrium, volumetric technique. All powder X-ray diffraction (PXRD) characterization was conducted on a Rigaku MiniFlex II with Cu $K_\alpha$ radiation. Scanning electron micrograph (SEM) images were acquired on a ZEISS 1550 VP FESEM, equipped with in-lens SE. EDS spectra were acquired with an Oxford X-Max SDD X-ray Energy Dispersive Spectrometer system.

Diffuse reflectance UV-visible (DRUV) spectra (for CIT-7) were recorded using a Cary 3G spectrophotometer equipped with a diffuse reflectance cell; zeolite samples were calcined prior to data collection. Three-dimensional electron diffraction data were collected on 2 crystals of CIT-7 using the rotation electron diffraction (RED) technique of Zhang (D. Zhang, P. Oleynikov, S. Hovmöller and X. Zou, Z. Kristallogr., 2010, 225, 94-102) and Wan (W. Wan, J. Sun, J. Su, S. Hovmöller and X. Zou, J. Appl. Cryst., 2013, 46, 1863-1873). The RED software was installed on a JEOL 2010 microscope operating at 200 kV, and data were collected over a tilt range of ±55° with a tilt step of 0.50° for the first set and 0.35° for the second set, the exposure time is 3 seconds per tilt step.

Example 2

Synthesis of Imidazolium Cations

Example 2.1

Pentamethylimidazolium hydroxide was synthesized as shown in in the following Scheme.

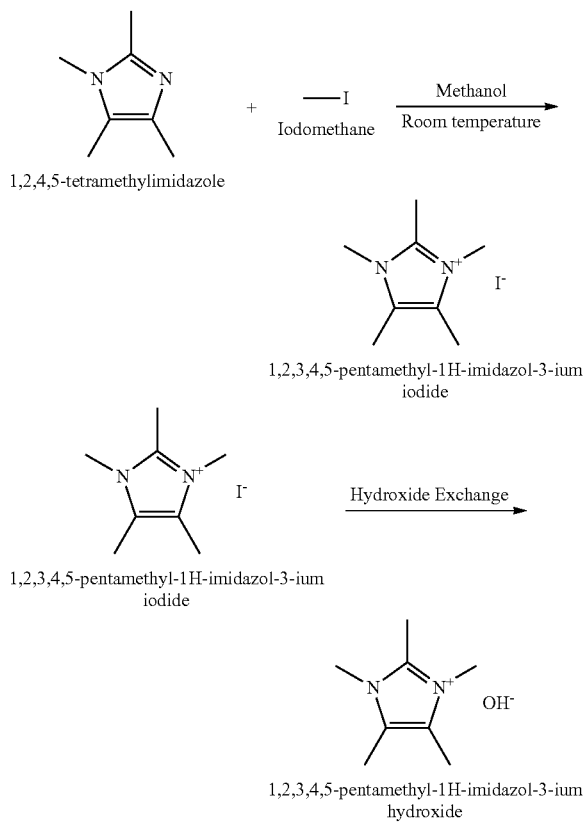

Pentamethylimidazolium was synthesized by dissolving 1,2,4,5-tetramethylimidazole (TCI Chemicals) in methanol and then cooling in a dry ice bath. A three-fold molar excess of iodomethane (Aldrich) was then slowly added (Caution: Highly exothermic reaction!) and the mixture was then slowly warmed to room temperature and stirred for one day. The solvent and excess iodomethane were then removed using rotary evaporation (Caution: Highly toxic vapors present, use appropriate precautions) and the product was recrystallized from acetone and washed with ether. The structure was verified using $^1$H and $^{13}$C NMR ($D_2O$, methanol added as internal standard) and the product was converted from the iodide to the hydroxide form using hydroxide exchange resin in water and the product was titrated using a Mettler-Toledo DL22 autotitrator using 0.01 M HCl as the titrant. $^1$H-NMR (500 MHz, $D_2O$): δ 3.60 (s, 6H), 2.54 (s, 3H), 2.20 (s, 6H). $^{13}$C-NMR (125 MHz, D2O): δ 7.99, 9.76, 31.58, 125.42, 142.21.

Example 2.2

Syntheses of Other Organic Structure Directing Agents (OSDAs)

Reaction Type 1:
The parent imidazole was dissolved in methanol and then cooled in a dry ice/acetone bath. Then a three-fold molar excess of methyl iodide was slowly added. (Caution: These reactions can be highly exothermic, use appropriate precautions.) The mixture was then allowed to slowly warm to room temperature and finally refluxed overnight. After cooling the solvent and excess methyl iodide were removed using rotary evaporation (Caution: Highly toxic vapors present, use appropriate precautions), and the product was recrystallized from acetone and washed with ether.

Reaction Type 2:
The parent imidazole was dissolved in chloroform and then a two-fold molar excess of potassium carbonate was added. The mixture was cooled in a dry ice/acetone bath and then a four-fold molar excess of methyl iodide was slowly added. (Caution: These reactions can be highly exothermic, use appropriate precautions.) The mixture was then allowed to slowly warm to room temperature and finally refluxed overnight. After cooling to room temperature the potassium carbonate was filtered off and the solids were rinsed with extra chloroform to recover all the product. Then the solvent and excess methyl iodide were removed using rotary evaporation (Caution: Highly toxic vapors present, use appropriate precautions), and the product was recrystallized from acetone and washed with ether.

In both types of reactions the structure was verified using $^{13}$C NMR in $D_2O$ with methanol added as an internal standard. The products were then converted from iodide to hydroxide form using hydroxide exchange resin (Dowex Marathon A, hydroxide form) in water, and the product was titrated using a Mettler-Toledo DL22 autotitrator using 0.01 M HCl as the titrant.

TABLE 3

Syntheses and Characterizations of Imidazolium Structure Directing Agents

| Organic | Parent Imidazole | Supplier | Reaction Type | $^{13}$C NMR δ (ppm) |
|---|---|---|---|---|
| 1 | N-methylimidazole | Aldrich | 1 | 36.32, 123.76, 136.86 |
| 2 | 1,2-Dimethylimidazole | Aldrich | 1 | 8.52, 34.48, 121.64, 144.63 |
| 3 | 4-methylimidazole | Aldrich | 2 | 8.52, 33.37, 35.87, 120.37, 132.33, 135.86 |
| 4 | 2-ethylimidazole | Aldrich | 2 | 9.92, 16.59, 34.71, 122.07, 148.16 |
| 5 | 2,4-dimethylimidazole | Synquest | 2 | 8.62, 9.38, 31.46, 34.36, 118.64, 130.14, 143.89 |
| 6 | 2-ethyl-4-methylimidazole | Aldrich | 2 | 8.80, 10.17, 16.93, 31.52, 34.36, 118.83, 120.23, 130.23, 147.32 |

TABLE 3-continued

Syntheses and Characterizations of Imidazolium Structure Directing Agents

| Organic | Parent Imidazole | Supplier | Reaction Type | $^{13}$C NMR δ (ppm) |
|---|---|---|---|---|
| 7 | 2-isopropylimidazole | TCI | 2 | 17.55, 24.79, 35.68, 122.65, 149.69 |
| 8 | 1,2,4,5-tetramethylimidazole | TCI | 1 | 7.99, 9.76, 31.58, 125.42, 142.21 |

The linked quaternary imidazolium cation OSDAs used in this work were synthesized by reacting 200 mmol of 1,2,4,5-tetramethylimidazole (TCI Chemicals) with 100 mmol of either 1,5-dibromopentane, 1,4-dibromobutane, or 1,3-dibromopropane (all from Aldrich) at reflux in methanol overnight. The solvent was then removed using rotary evaporation and the product washed with ether. The products were verified using $^{13}$C NMR in $D_2O$ with methanol added as an internal standard. $^{13}$C-NMR (125 MHz, $D_2O$), pentane linked pentamethyl imidazolium cations: δ 7.76, 7.82, 9.61, 22.82, 28.58, 31.42, 44.72, 124.84, 126.03, 141.95. $^{13}$C-NMR (125 MHz, $D_2O$), butane linked pentamethyl imidazolium cations: δ 7.56, 9.35, 25.88, 30.17, 21.21, 44.14, 124.60, 126.00, 141.89. HRMS-FAB (m/z): [M+H] calculated for $C_{18}H_{31}N_4$, 303.25. found, 303.26. The products were ion exchanged and titrated as described above.

Example 3.1

General Methods for Preparation of Crystalline Microporous Silicate or Aluminosilicate Solids Using Imidazolium Cations The following general synthesis procedures were used in the preparation of the microporous materials can be found below. In all situations where a rotating oven was used the samples were spun at 63 rpm. All powder x-ray diffraction characterization was conducted on a Rigaku MiniFlex II with Cu Kα radiation.

Example 3.2

Fluoride Mediated Reactions

A general procedure for a fluoride mediated synthesis was as follows. Tetraethylorthosilicate (TEOS) and aluminum isopropoxide (if necessary) were added to the OSDA in its hydroxide form in a Teflon Parr reactor liner. The container was closed and stirred for at least 12 hours to allow for complete hydrolysis. The lid was then removed and the alcohol and appropriate amount of water were allowed to evaporate under a stream of air. The composition was monitored gravimetrically. Additional water was added as necessary, and then aqueous HF (Aldrich) was added and the mixture was stirred by hand until a homogenous gel was obtained. (Caution: Use appropriate personal protective equipment, ventilation and other safety measures when working with HF.) In some cases, the final molar ratios of the gel were:

(1-x) $SiO_2$:x Al:0.5 ROH:0.5HF:y $H_2O$.

In those experiments involving pure silica gels or gels evaluating OSDAs other than pentamethyl imidazolium hydroxide in RTH syntheses, the final gel molar ratios were:
1 $SiO_2$:0.5 ROH:0.5 HF:x $H_2O$, x=4, 7
0.95 $SiO_2$:0.05 Al:0.5 ROH:0.5 HF:4 $H_2O$ In other cases where the final compositions were Si/Al=15 (i.e., in forming the CIT-7 compositions), the final molar ratios were:
1 $SiO_2$:0.0333 Al:0.08 $Na_2O$:0.16 ROH:30 $H_2O$ The parameters x and y were varied depending on the synthesis and the desired composition. For low water syntheses, a final evaporation step was used after the addition of HF to reach the desired water ratio. The Teflon-lined Parr reactor was sealed and placed in a rotating oven at 160° C. or 175° C. Aliquots of the material were taken periodically by first quenching the reactor in water and then removing enough material for powder X-ray diffraction (PXRD).

Example 3.3

Hydroxide Mediated Reactions

For the hydroxide syntheses, several variations on gel Si/Al as well as the sources of silica and alumina were used. Specific synthesis preparations are below. For all hydroxide reactions, seeds were added after 1 day at reaction temperature, once a decrease in pH was observed. Normally seeds were added as a homogeneous aliquot of the contents of a previous, completed reaction (less than 0.3 mL) as these were found to be more active than seeds that had been washed. The use of seeds was found to speed the formation of RTH and to help avoid the formation of dense phases, but this influence was not extensively investigated. Aliquots were taken periodically, and crystallization was monitored by both PXRD and pH, as an increase in pH was generally observed when the product crystallized. After the product crystallized, the material was washed with DI water and then collected via centrifugation. This process was repeated at least three times, and a final wash was performed using acetone. The product was dried at 100° C. in air.

Example 3.4

Sodium Aluminate (or Reheiss F-2000) and Ludox AS-40 (or Cabosil)

The OSDA in its hydroxide form, sodium hydroxide (if necessary), any necessary water and sodium aluminate (Pfaltz & Bauer) were combined in a Teflon Parr reactor liner and stirred until the sodium aluminate completely dissolved. Ludox AS-40 (Aldrich) was then added and stirred until a homogenous gel was obtained. In sodium-free syntheses, Reheiss F-2000 (55 wt % $Al_2O_3$) was used as the source of aluminum instead of sodium aluminate, and Cabosil M-5 was used instead of Ludox AS-40. The gel pH was measured, and then the Teflon-lined Parr reactor was placed in a rotating oven at 160° C.

Example 3.5

Si/Al=15 ($NH_4$—Y and Sodium Silicate

Following the method of Wagner et al., J. Am. Chem. Soc. 2000, 122, 263, 2 mmol of the OSDA in its hydroxide form was mixed with 0.20 g of 1 M NaOH, and water was added to give a total mass of 6 g. Then 2.5 grams of sodium silicate (PQ Corporation, 28.6 wt % $SiO_2$ and 8.9 wt % $Na_2O$) was added to the mixture and finally 0.25 g of $NH_4$—Y (Zeolyst CBV 500, Si/Al=2.55) was added. The solution was heated at 140° C. in a rotating oven.

Example 3.6

Si/Al=15 (CBV 720)

3 mmol of the OSDA in its hydroxide form was mixed with 1 g of 1 M NaOH and water was added to bring the total mass to 7 g. Then 1 g of CBV 720 (Zeolyst, Si/Al=15) was added. The solution was heated at 175° C. in a rotating oven.

Example 3.7

Si/Al=30 (CBV 760)

3 mmol of the OSDA in its hydroxide form was mixed with 1 g of 1 M NaOH and water was added to bring the total mass to 7 g. Then 1 g of CBV 760 (Zeolyst. Si/Al=30) was added. The solution was heated at 175° C. in a rotating oven.

Example 3.8

SSZ-13 Synthesis

SSZ-13 was synthesized using a standard method of Robson, H. *Verified synthesis of zeolitic materials;* 2001. In a typical preparation, 3.33 g of 1 M NaOH was mixed with 2.81 g of N,N,N-trimethyl-1-adamantammonium hydroxide (Sachem, 1.18 mmol OH/g) and 6.62 g of water. Then 0.077 g of Reheiss F-2000 (55 wt % $Al_2O_3$) was added and stirred until the solution cleared. Finally, 1.00 g of Cabosil M-5 was added and stirred until a homogeneous solution was obtained. The solution was heated at 160° C. in a rotating oven for approximately 6 days.

Example 3.9

SAPO-34 Synthesis

SAPO-34 was prepared from the following gel composition: $0.5(TEA)_2O:1.5Pr_2NH:0.6SiO_2:1Al_2O_3:1P_2O_5:70H_2O$. In a typical preparation, 11.5 g of 85 wt % phosphoric acid were dissolved in 4.35 g of water and stirred for 5 minutes. Then 6.875 g of Catapal B alumina were added to 20 g of water and stirred for 10 minutes. The mixtures were then slowly combined and stirred for 1 hour at room temperature. Next 4.48 g of Ludox HS-40 was added and stirred by hand until a homogenous gel was obtained. Then 20.8 g of 35 wt % TEAOH and 7.61 g of dipropylamine were added and the gel was homogenized by manual stirring. Then the gel was stirred at room temperature for 2 hours. Finally, the gel was added to a Teflon-lined Parr reactor and heated at 200° C. without stirring for 24 hours.

Example 3.10

Si/Al=50 (Ludox AS-40 and Sodium Aluminate)

4 mmol of the OSDA in its hydroxide form was mixed with 1.56 g of 1 M NaOH and the total mass was brought to 9.66 g with the addition of water. Then 0.038 g of sodium aluminate (Pfaltz & Bauer) was added and stirred until dissolved. Finally 3 g of Ludox AS-40 was added and stirred until a homogeneous gel was obtained. Seeds were added and then the gel was heated at 160° C. in a rotating oven.

Example 3.11

Tosoh 390HUA reaction: Following the method of Zones et al., *Chem. Mater.*, 26 (2014) 3909-3913, 3 mmol of the OSDA in its hydroxide form and 0.75 g of 1 M KOH were added to a Teflon Parr Reactor. Then 0.92 g of Tosoh 390HUA was added (highly dealuminated FAU with Si/Al~250) and the mixture was stirred until homogeneous. The gel was heated at 175° C. in a rotating oven.

Example 3.12

Calcination

All products were calcined in breathing grade air. The material was heated to 150° C. at 1° C./min under flowing air, held for three hours, then heated to 580° C. at 1° C./min and held for 6-12 hours under flowing air to assure complete combustion of the organic.

Example 4

Reaction Testing of RTH Materials

Prior to reaction testing, all materials were calcined as described above. After calcination they were exchanged to ammonium form using 1 M $NH_4NO_3$ (100 mL of solution per gram of catalyst) at 95° C. with stirring for three hours, this was done a total of three times per sample. After ammonium exchange the materials were washed with water and dried and then calcined. The calcined materials were then pelletized, crushed, and sieved. Particles between 0.6 mm and 0.18 mm were supported between glass wool beds in an Autoclave Engineers BTRS, Jr. SS-316 tubular, continuous flow reactor.

All catalysts were dried at 150° C. in situ in a 30 $cm^3$/min flow of 5% Ar/95% He for 4 h prior to the reaction. The reactions were conducted at 400° C. in a 10% methanol/inert flow. Methanol was introduced via a liquid syringe pump at 5.4 µL/min, into a gas stream of the inert blend at 30 $cm^3$/min. The reactant flow had a weight hourly space velocity of 1.3 $h^{-1}$. In a typical run, 200 mg of dry catalyst was loaded. Effluent gases were evaluated using an on-stream GC/MS (Agilent GC 6890/MSD5793N) with a Plot-Q capillary column installed. Conversions and selectivities were computed on a carbon mole basis. Catalyst regeneration between reaction tests was done in-situ by exposing the catalyst to breathing grade air at reaction temperature, ramping to 580° C. at 1° C./min, holding at 580° C. for 6 hours, and then cooling to reaction temperature.

Example 5

Results

In pure silicate systems, as well as germanosilicate systems, the mono-imidazolium cations directed the formation of STW. However, when aluminum was introduced into the system the product was aluminosilicate RTH. In the initial series of experiments, the reaction conditions were those shown in Table 4. A representative powder X-ray diffraction pattern of one of the materials obtained is shown in FIG. 1. All peaks matched those reported for the spectrum for RTH.

TABLE 4

RTH Synthesis Conditions. Experimental Series #1

| Si | Al | R+ | F− | H$_2$O | Temp, ° C. | Time, days | Results | Comments |
|---|---|---|---|---|---|---|---|---|
| 1 | 0.02 | 0.5 | 0.5 | 14 | 160 | 12 | RTH | |
| 1 | 0.05 | 0.5 | 0.5 | 14 | 160 | 12 | RTH | |
| 1 | 0.05 | 0.5 | 0.5 | 4 | 160 | 10 | RTH | |
| 1 | 0.05 | 0.5 | 0.5 | 4 | 160 | 10 | RTH | |
| 1 | 0.05 | 0.5 | 0.5 | 7 | 160 | 4 | RTH + STW | STW seeds added |

Figure 5:
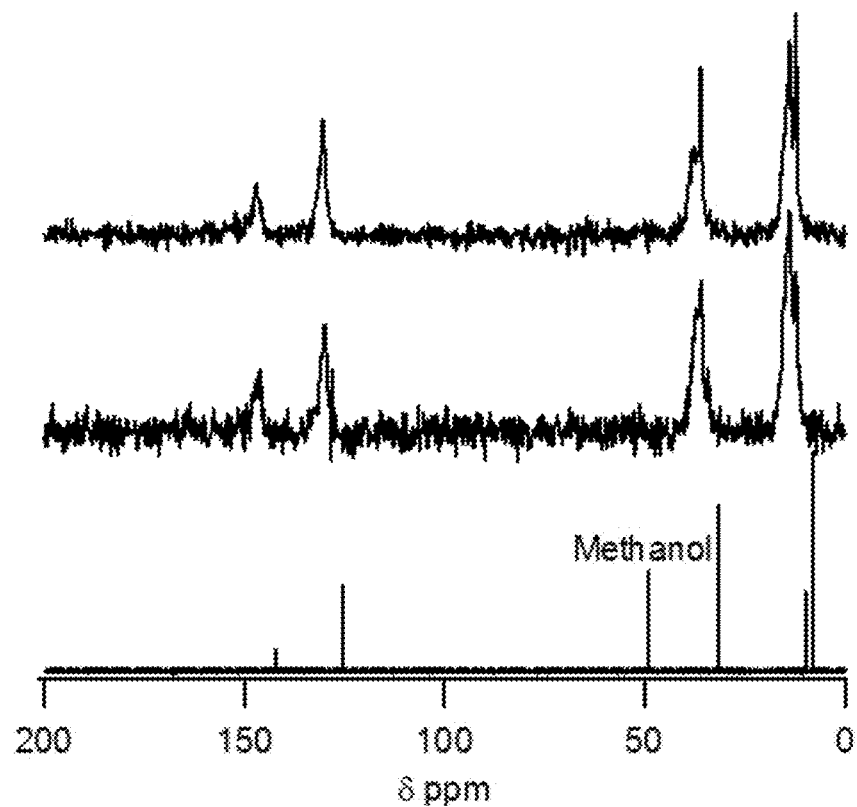
FIG. 5 shows a $^{13}C$ NMR spectra of pentamethylimidazolium in $D_2O$ with methanol standard (lower), $^{13}C$ CP-MAS NMR of as-made RTH prepared in hydroxide media (middle, sample H4) and $^{13}C$ CP-MAS NMR of as-made RTH prepared in fluoride media (upper, sample F4).

Molar ratios of materials based on Si = 1
R+ refers to pentamethylimidazolium cation Subsequent experiments were directed to expanding the range of compositions (Table 5). In these experiments, it was shown that the fluoride method was able to produce RTH across a wide range of compositions, but at the highest Si/Al ratios tested, STW appeared as a competitive phase (sample F9). The crystal sizes and morphologies were consistent with pure-silicate RTH produced in fluoride media, and the large crystal size was what is generally observed for low-water, fluoride-mediated syntheses. Comparison of $^{13}$C CP-MAS NMR spectra of the as-synthesized RTH zeolite with a solution spectrum of the pentamethylimidazolium ion in D$_2$O showed that it was this cation, and not a decomposition product, that led to the formation of aluminosilicate RTH. See FIG. 5. In order to determine the coordination of the aluminum in the material, $^{27}$Al MAS NMR was performed on the calcined sample containing the highest amount of aluminum (sample F2), and the spectrum is shown in FIG. 6. The single resonance in this sample at 54 ppm is consistent with tetrahedrally coordinated aluminum, and there is no evidence of octahedrally coordinated aluminum, normally found around 0 ppm.

TABLE 5

RTH Synthesis in Fluoride Media. Experimental Series #2

| Gel Si/Al | Product Si/Al* | Gel H$_2$O/SiO$_2$ | Time, days | Sample |
|---|---|---|---|---|
| 5 | — | 7 | No product | F1 |
| 10 | 7 | 7 | 29 | F2 |
| 15 | 10 | 14 | 46 | F3 |
| 20 | 16 | 14 | 22 | F4 |
| 20 | 18 | 4 | 10 | F5 |
| 33 | 22 | 14 | 20 | F6 |
| 40 | 26 | 14 | 17 | F7 |
| 50 | 27 | 14 | 20 | F8 |
| 150 | STW impurity | 7 | 7 | F9 |

*Reported Si/Al ratio is of calcined materials

Figure 4A:
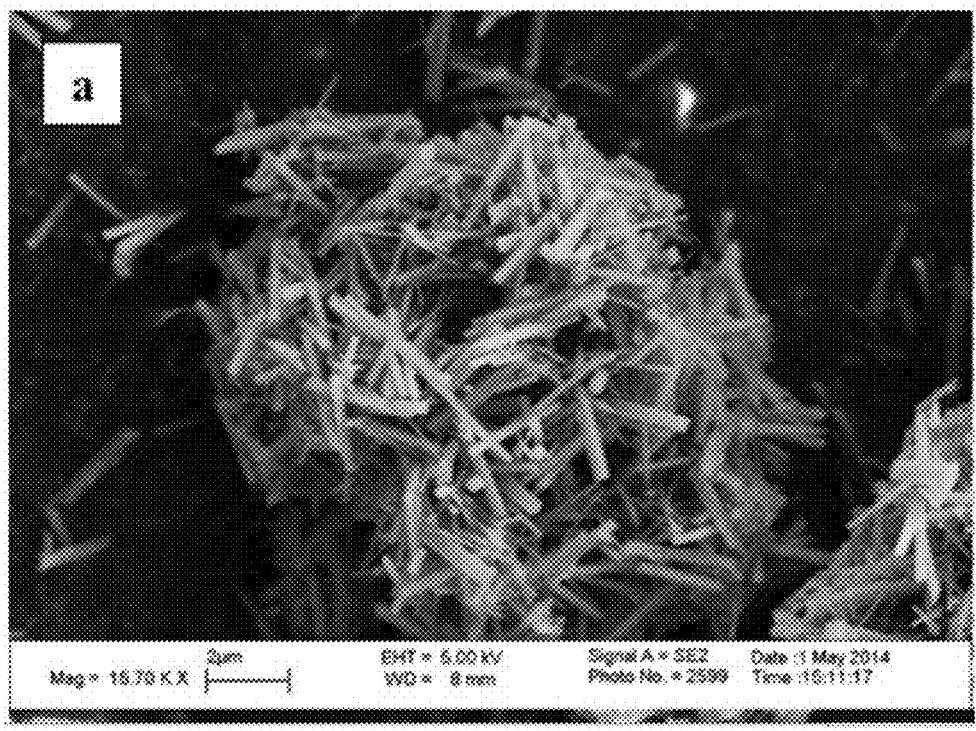
Figure 7:
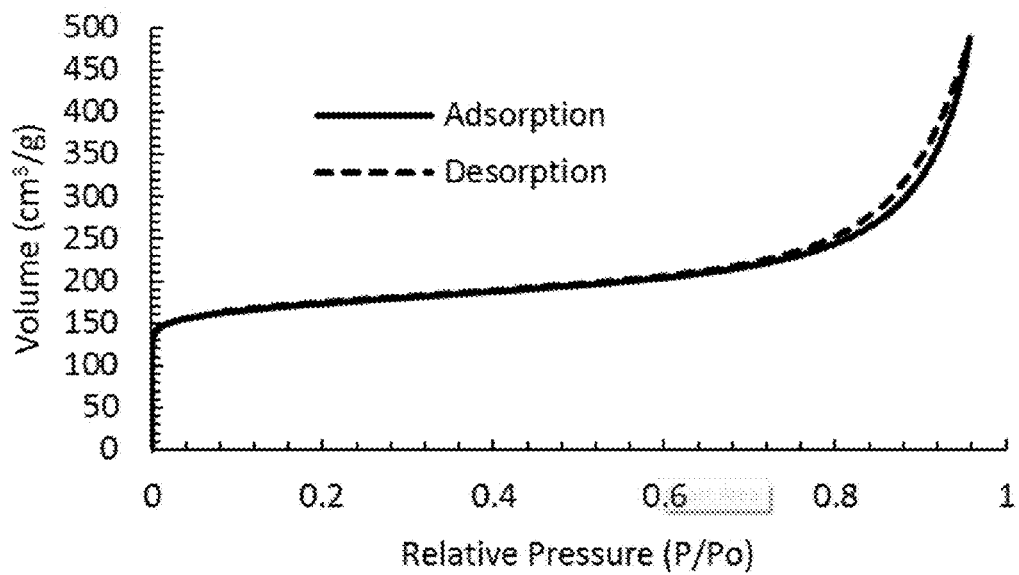
FIG. 7 show an argon isotherm for aluminosilicate RTH prepared in hydroxide media with product Si/Al=14 (sample H4).

The success of using pentamethylimidazolium in fluoride-mediated reactions to produce aluminosilicate RTH led to work in hydroxide-mediated reactions as well, with seeds of RTH added to promote its formation. The results of the syntheses are shown in Table 6. In general, these syntheses were found to be sensitive to reaction time and temperature, and required careful monitoring to avoid the formation of dense phases. Seeds of RTH were added to all reactions to promote the formation of RTH, but the exact influence of the seeds was not extensively investigated. A representative PXRD of the calcined material produced in hydroxide media is shown in FIG. 2. The crystal sizes of the products were generally much smaller in hydroxide syntheses than in the fluoride syntheses, as is shown in FIG. 4A-C. The smaller crystal sizes observed under these conditions are consistent with what is generally reported in hydroxide syntheses. It is interesting to note that the aggregation appeared to be different in reactions where no sodium was present compared to those with sodium present (FIG. 4A-C). $^{13}$C CP-MAS NMR showed that pentamethylimidazolium was also occluded intact in the material prepared in hydroxide media (FIG. 4A-C). $^{27}$Al MAS NMR was used to characterize the sample containing the largest amount of aluminum (sample H1), as was done in the fluoride-mediated case, and is shown in FIG. 6. There is a single resonance at 54 ppm corresponding to tetrahedrally coordinated aluminum and no evidence of any significant amount of octahedral aluminum. An argon adsorption isotherm for sample H4 is shown in FIG. 7, and the micropore volume was calculated to be 0.16 cm$^3$/g (t-plot method). The EDS analyses of the materials synthesized in hydroxide media are given in Table 6, and the results show that RTH can be crystallized across a wide range of compositions from Si/Al of 6 to 59 in the calcined product (a large expansion over previously reported results). Of significant interest are the low-silica syntheses (the lowest product found was Si/Al=6, sample H1), much lower than any other reported compositions.

TABLE 6

RTH Synthesis in Hydroxide Media. Experimental Series #3

| Gel Si/Al | Product Si/Al[a] | Gel Na/Si | Gel ROH/Si | Gel H$_2$O/Si | Time, days | Sample |
|---|---|---|---|---|---|---|
| 5[b] | 6 | 0.16 | 0.16 | 30 | 10 | H1 |
| 10[b] | 9 | 0.16 | 0.16 | 30 | 10 | H2 |
| 15[c] | 9 | | | | 9 | H3 |
| 15[b] | 14 | 0.16 | 0.16 | 30 | 10 | H4 |
| 15[d] | 15 | | 0.32 | 30 | 15 | H5 |
| 15[e] | 17 | | | | 10 | H6 |
| 20[b] | 20 | 0.16 | 0.16 | 30 | 12 | H7 |
| 30[f] | 29 | | | | 13 | H8 |
| 50[b] | 45 | 0.10 | 0.20 | 30 | 9 | H9 |
| 75[b] | 59 | 0.10 | 0.20 | 30 | 9 | H10 |

[a]Reported Si/Al ratio is of calcined material;
[b]Made with Ludox AS-40 and sodium aluminate;
[c]Made with NH$_4$—Y and sodium silicate;
[d]Made using Cabosil M-5 and Reheiss RE-2000;
[e]Made using CBV 720 as only source of Si and Al;
[f]Made using CBV 760 as only source of Si and Al.

Example 6

Reaction Testing

The catalytic activity of RTH for the MTO reaction was evaluated using three different samples of RTH prepared in hydroxide media at different Si/Al ratios, and the results were compared to samples of SSZ-13 and SAPO-34. The samples of RTH tested were prepared using the CBV 720, CBV 760 and the sodium aluminate and Ludox synthesis routes, with product Si/Al values of 17, 29 and 59, respectively (samples H6, H8, H10). The sample of SSZ-13 had a product Si/Al of 19. The MTO reaction data for the SSZ-13 and SAPO-34 are given in FIG. 8A and FIG. 8B, for the RTH materials is given in FIG. 8C-G.

Figure 8A:
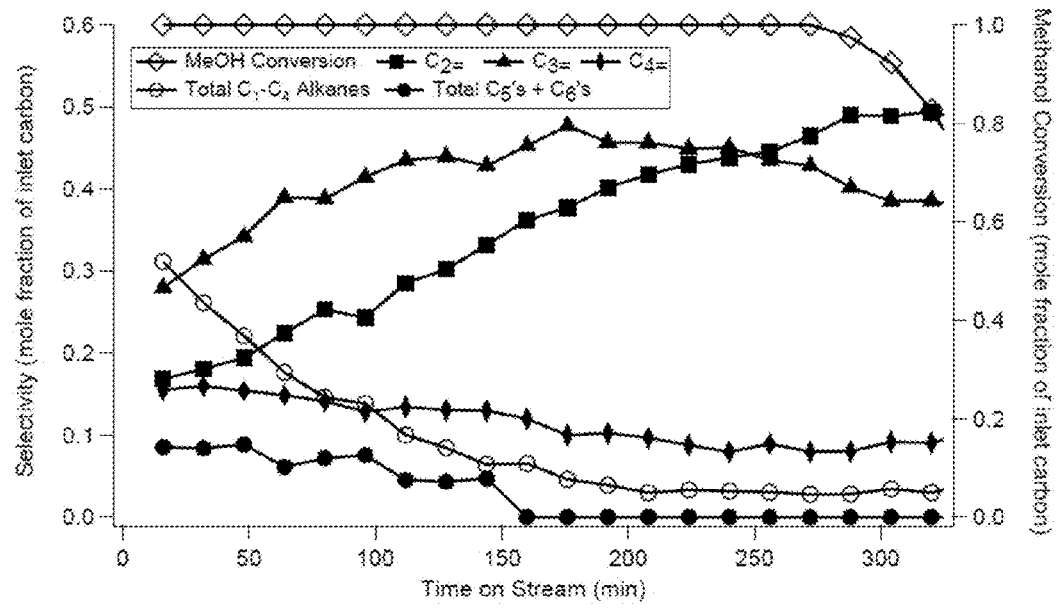
FIG. 8A-G shows MTO reactivity data for various compositions described herein.
Figure 8B:
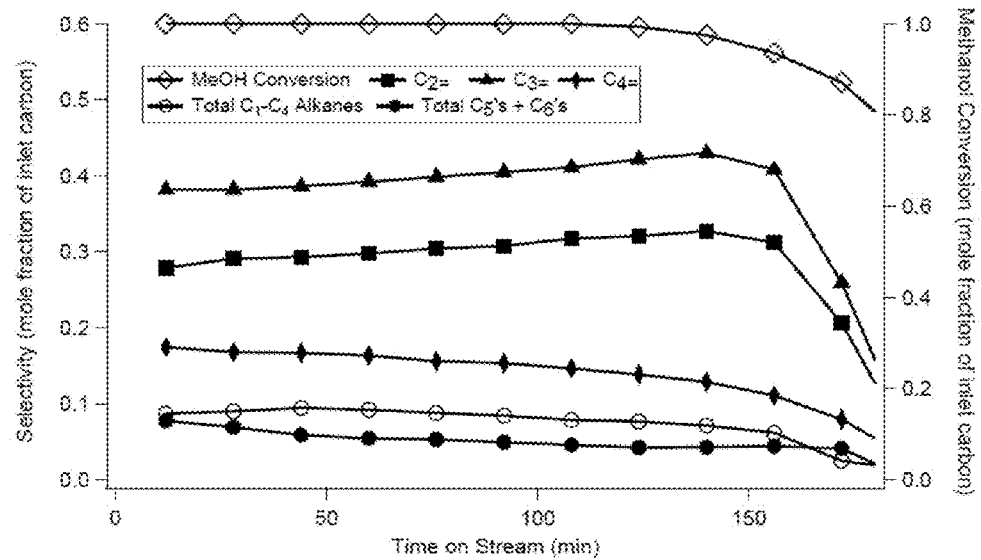
Figure 8C:
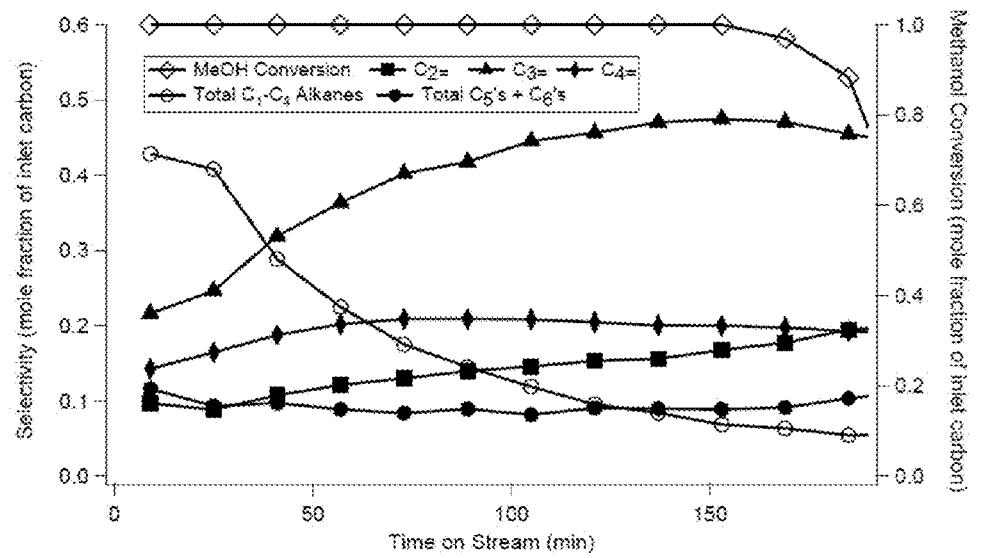
Figure 8D:
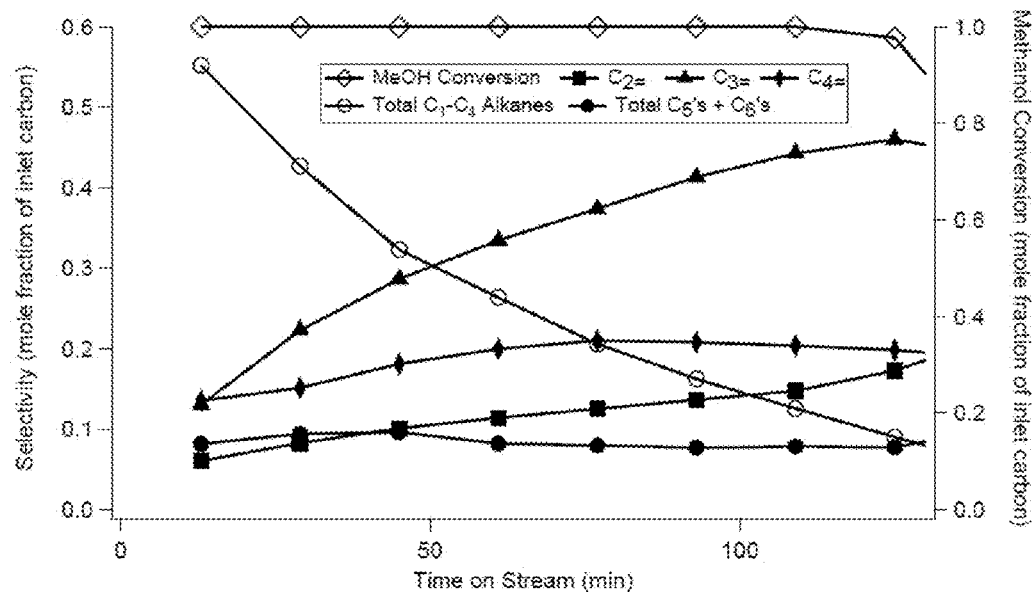
Figure 8E:
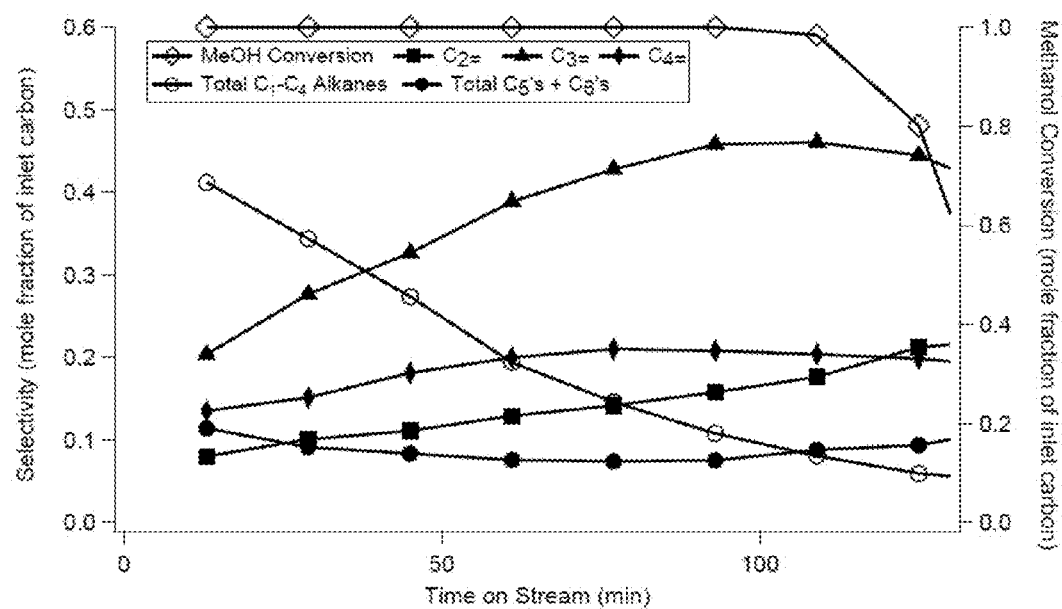
Figure 8F:
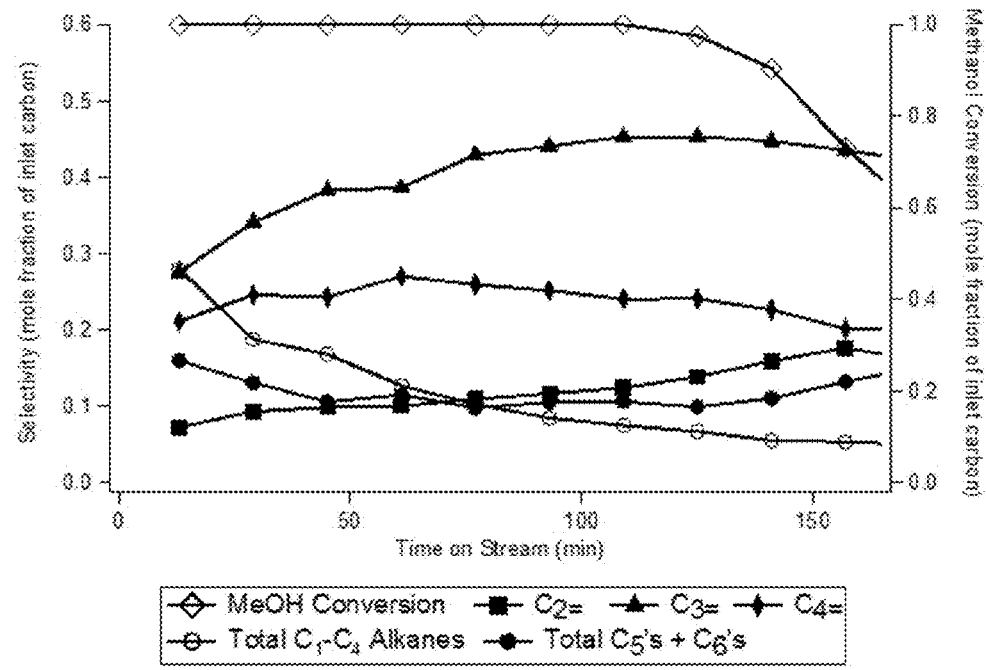
Figure 8G:
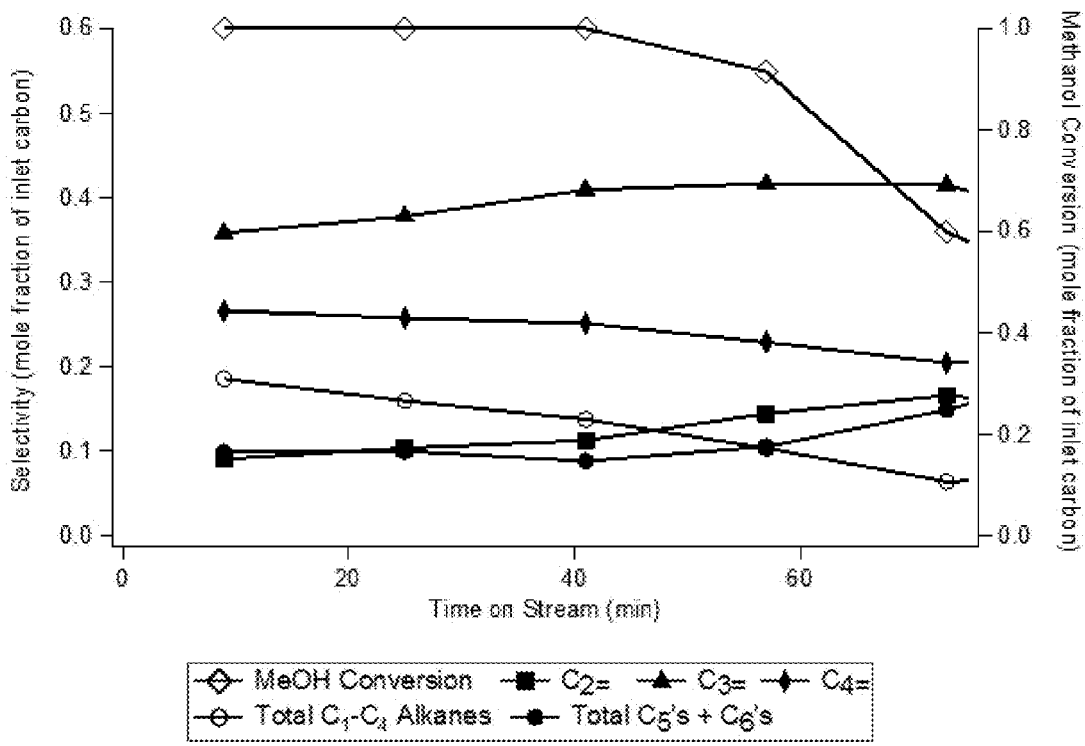

The propylene to ethylene ratio was much higher for RTH than SSZ-13 or SAPO-34. In sample H6 with Si/Al=17, the maximum propylene to ethylene selectivity ratio observed was 3.6 at 96 minutes on stream. For sample H8 with Si/Al=29, the maximum propylene to ethylene selectivity ratio observed was 3.9 at 96 minutes on stream. For sample H10 with Si/Al=59, the maximum propylene to ethylene selectivity ratio observed was 3.6 between 25 and 41 minutes on stream. These selectivity ratios are much higher than those observed with SSZ-13 or SAPO-34, where the maximum propylene to ethylene ratios are 1.7 at 96 minutes on stream and 1.3 across several time points, respectively (FIGS. 8A and 8B). This result shows that RTH would be a superior catalyst in applications where a higher propylene to ethylene ratio is desired.

The selectivity towards butene was also higher for RTH than for SSZ-13 or SAPO-34. The maximum selectivities to butene for the RTH samples were 0.22, 0.27 and 0.25 for the samples with Si/Al=17, 29 and 59, respectively (H6, H8, H10). The highest selectivity observed for SSZ-13 was 0.15 and for SAPO-34 was 0.17 (FIGS. 8A and 8B).

With the RTH samples, one of the main differences between the samples was the selectivity to $C_1$-$C_4$ saturates (mainly propane). The maximum selectivity for each sample occurred at the first time point, and the values were 0.39, 0.28 and 0.19 for the samples with Si/Al=17, 29 and 59, respectively (samples H6, H8, H10). It was also observed that time on stream with complete methanol conversion decreased with increasing Si/Al ratios.

When comparing RTH to SSZ-13 or SAPO-34, one of the main differences observed was the time on stream until the catalyst deactivated. In all the RTH samples, this was significantly less than it was for either SSZ-13 or SAPO-34. However, an industrial scale MTO reaction will likely be run in a fluidized-bed reactor, which allows continuous regeneration of the catalyst. This will allow a system to be operated at any time point along a fixed bed reactor profile, assuming the catalyst can be regenerated. To this end, the ability of RTH to be regenerated was tested by running the Si/Al=17 material (sample H6) for three consecutive MTO reaction runs with regeneration between each run, and the results are given in FIGS. 8C-D. There are some small differences between the fresh catalyst (FIG. 8C) and first regeneration of the catalyst (FIG. 8D), but the MTO reaction behavior is similar between the first regeneration (FIG. 8D) and second regeneration (FIG. 8E) of the material. The regeneration experiment demonstrates that RTH would be suitable for use in fluidized bed systems as it can maintain its activity across multiple regeneration cycles.

Example 7

Testing Additional Imidazolium Cations

Example 7.1

Syntheses of Aluminosilicate RTH

Results of the imidazolium screening reactions are given in Table 7. It was found that nearly all of the imidazolium screened in this study led to the formation of RTH. The simplest imidazolium OSDA, 1, did not produce RTH and was found to decompose under many of the conditions tested in this study. It was found to produce materials in fluoride mediated reactions, consistent with those previously reported, so the instability is property of the organic. Additionally, OSDA 7 was also unstable under many of the conditions tested in these screening reactions, and was not found to lead to RTH under any conditions tested.

All of the other OSDAs tested were able to produce aluminosilicate RTH under a majority of the inorganic conditions tested. The formation of aluminosilicate RTH using pentamethylimidazolium was first observed in fluoride-mediated aluminosilicate conditions, and OSDAs 2-6, 8 were all able to produce RTH under this condition, without the use of seeds. Under more conventional, hydroxide-mediated conditions, they were also observed to form RTH across a wide compositional range. In some cases, such as with OSDAs 2-4 the use of seeds was found to be necessary to cause the formation of RTH. This suggests that these organics were less directing to RTH, but are still able to form the material when nucleation is induced through seeding. The OSDAs found to be the most strongly directing to RTH were 2, 5 and 8.

Example 7.2

Pure-Silica RTH

Figure 9B:
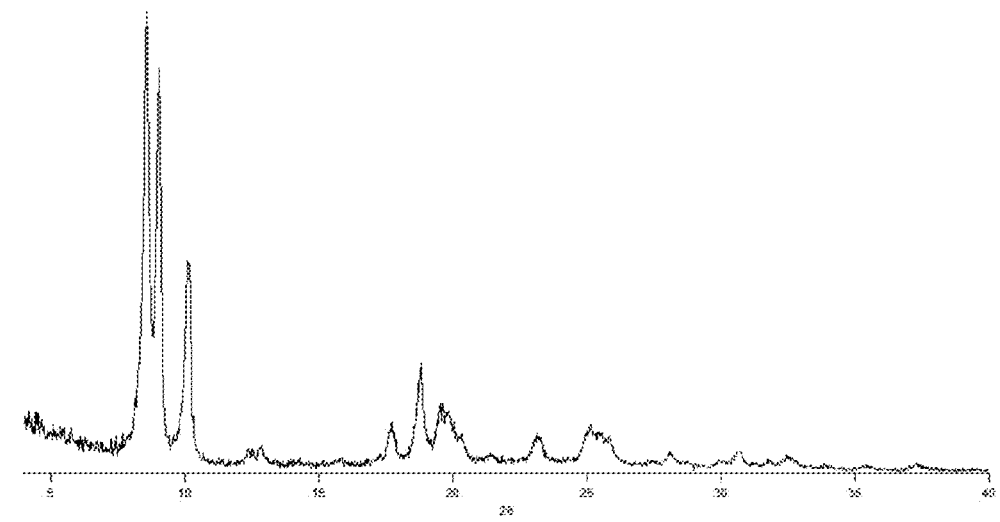

None of the mono-quat imidazolium examined in this study was able to produce pure-silica RTH. The only previously reported method to make this material uses a difficult to produce OSDA (see Background, above). Recent investigations by the present inventors have examined linked pairs of quaternary imidazolium cations ("diquats") produced using tetramethylimidazole. The diquat with a 5-carbon linker in low-water, fluoride-mediated reactions was found to produce pure-silica RTH at $H_2O/Si_2O=4$, in competition with BEA, STW and CIT-7. From the as-made material. FIG. 9, lower trace) it was not obvious that the material produced is RTH, this was only apparent upon calcination. Initially, it was thought that the RTH was formed through topotactic condensation. This was tested by treating the material in ozone at 150° C., below the temperature at which topotactic condensation is reported to occur, which is above 500° C. Under these conditions the formation of RTH was also apparent, and the similarity of the as-made and calcined PXRD samples suggests that it is likely that the PXRD of the as-made material was due to the organic phase. This is only the second report of pure silica RTH and in this method the organic is accessible in only a single step.

TABLE 7

Results of various microporous materials syntheses.

| Organic | Number | Pure Si fluoride $H_2O/$ $SiO2 = 4$, 175° C. | Pure Si fluoride $H_2O/$ $SiO2 = 7$, 175°C. | Si/Al = 20 fluoride | Si/Al = 15 Seeds | Si/Al = 15 no seeds | CBV720, 160° C., seeds | CBV720, 160° C., no seeds | CBV720, 175° C., seeds | CBV760, 175° C., no seeds | Si/Al = 50 seeds | Tosoh 390, 175° C., no seeds |
|---|---|---|---|---|---|---|---|---|---|---|---|---|
| 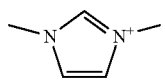 | 1 | TON | TON | FER | OD | | OD | OD | TON | TON | | ZSM-48 + D |

TABLE 7-continued

Results of various microporous materials syntheses.

| Organic | Number | Pure Si fluoride H₂O/ SiO2 = 4, 175° C. | Pure Si fluoride H₂O/ SiO2 = 7, 175°C. | Si/Al = 20 fluoride | Si/Al = 15 Seeds | Si/Al = 15 no seeds | CBV720, 160° C., seeds | CBV720, 160° C., no seeds | CBV720, 175° C., seeds | CBV760, 175° C., no seeds | Si/Al = 50 seeds | Tosoh 390, 175° C., no seeds |
|---|---|---|---|---|---|---|---|---|---|---|---|---|
| 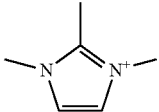 | 2 | ITW | ITW | RTH | RTH | RTH |  | RTH | RTH | OD | RTH | D |
| 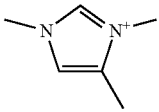 | 3 | ITW | ITW | RTH | RTH | MOR | OD | OD | TON | OD | TON | ZSM-48 |
| 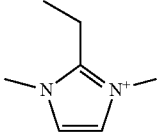 | 4 | CIT-7, ITW, STW, STF, MTW | ITW | RTH | RTH | RTH | RTH | OD | OD | OD | MTW | D |
| 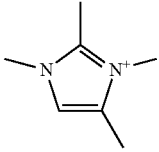 | 5 | STW | STW | RTH | RTH | RTH + MOR | RTH | RTH | RTH | RTH |  | D |
| 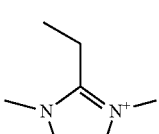 | 6 | STW | HPM-2 | RTH | RTH | MOR + RTH | OD | OD | OD | OD | MTW | D |
| 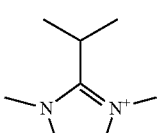 | 7 | STF | ?? | ?? | MOR | MOR | OD | OD | OD |  |  |  |
| 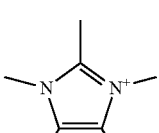 | 8 | STW | STW | RTH | RTH | RTH | RTH | RTH | RTH | RTH | RTH | D |

OD = Organic Decomposed
A = Material was still amorphous after 30 days but it was not apparent that the organic had degraded.
D = Dense Phase
?? Product could not be identified

Example 8.1

Investigations into the Preparation of CIT-7

The OSDAs used to produce CIT-7 were 2-ethyl-1,3-dimethylimidazolium (1) and 3,3'-(butane-1,4-diyl)bis(1,2,4,5-tetramethyl-1H-imidazol-3-ium) (2) and are shown as:

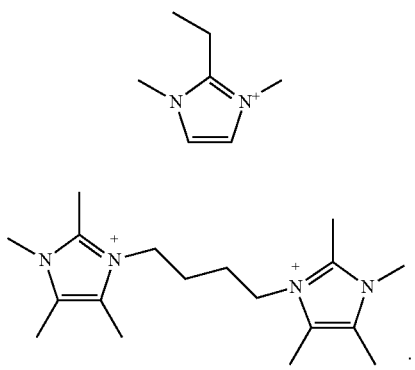

The synthesis and characterization details for these OSDAs can be found in Example 1.

A wide range of products could be produced with the 2-ethyl-1,3-dimethylimidazolium cation in fluoride-mediate, pure-silica reactions depending on the specific inorganic conditions used such as $H_2O/SiO_2$ ratio and temperature. Results of syntheses over a wide range of conditions are given in Table 8.

TABLE 8

Pure-silica fluoride-mediated syntheses using 2-ethyl-1,3-dimethylimidazolium cation

| $H_2O/SiO_2$ | Temperature (° C.) | Result |
|---|---|---|
| 2 | 140 | Unknown |
| 4 | 140 | STF |
| 7 | 140 | Amph |
| 14 | 140 | Amph |
| 2 | 160 | ITW |
| 4 | 160 | STW + ITW |
| 7 | 160 | ITW + MTW |
| 14 | 160 | ITW |
| 2 | 175 | STW |
| 4 | 175 | Unknown |
| 7 | 175 | ITW |
| 14 | 175 | MTW |
| 2 | 175 | STE + CIT-7 + ITW |
| 2.5 | 175 | CIT-7 |
| 3 | 175 | CIT-7 |
| 3.5 | 175 | ITW + CIT-7 |
| 4 (13 separate trials)[a] | 175 | CIT-7 + ITW |
| 4.5 | 175 | CIT-7 + STW |
| 5 | 175 | ITW + Unknown |
| 6 | 175 | Pending |

Figure 10:
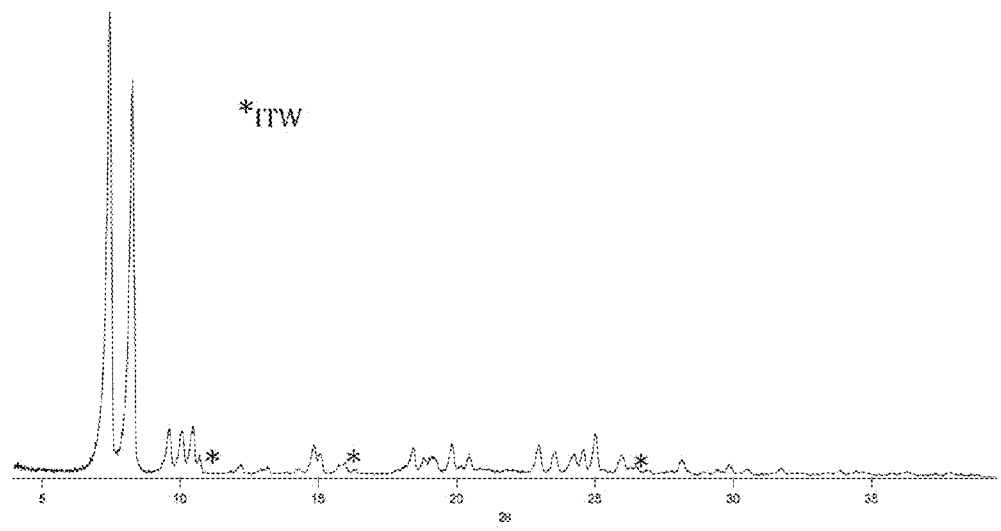
FIG. 10 shows representative powder X-ray diffraction (XRD) pattern for calcined pure silica CIT-7 material (made with 2-ethyl-1,3-dimethylimidazolium cation) containing an ITW impurity, marked with *. See Example 8.1.

Unknown means products could not be identified.
In reactions with multiple products phase mixtures were found but relative amounts were not quantified
[a] Seeds of CIT-7 were added Many known products emerged in these syntheses such as ITW, MTW, STF and STW as well as a few products that could not be characterized. In particular at low $H_2O/SiO_2$ ratios at 175° C. a phase was identified using powder x-ray diffraction (XRD) that was not a known microporous material phase. However, this phase was typically found as a phase mixture with either ITW or STW. A representative XRD of a calcined, pure-silica material made with 2-ethyl-1,3-dimethylimidazolium cation containing both CIT-7 as well as an ITW impurity is shown in FIG. 10. It was found that the use of seeds of CIT-7 helped to avoid the formation of ITW or STW, but it was found to be difficult to avoid the formation of any competing phases. At $H_2O/SiO_2$=2.5 and 3 it was not possible to detect any impurity phases using XRD, but in general it was difficult to synthesize a sample of pure CIT-7 using 2-ethyl-1,3-dimethylimidazolium cation as it is able to form many competing phases.

In addition to these imidazolium based OSDAs, additional studies into the use of linked pairs of quaternary imidazolium cations, having differing carbon chain lengths between the imidazolium moieties, such as shown here:

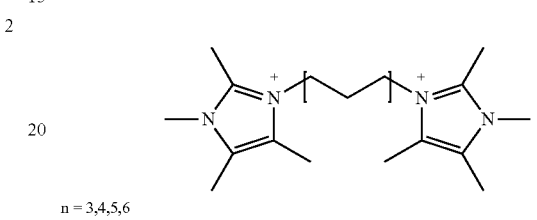

n = 3,4,5,6 have been used in pure-silica, fluoride-mediated syntheses at 175° C. and aluminosilicate, hydroxide-mediated syntheses with Si/Al=15 at 160° C. Representative results for various carbon linker chain lengths are given in Table 9.

TABLE 9

Synthesis results using tetramethylimidazolium diquats of varying carbon linker length

| Organic | $H_2O/SiO_2$ = 4, 175° C. | $H_2O/SiO_2$ = 7, 175° C. | Si/Al = 10, hydroxide | Si/Al = 15, hydroxide | Si/Al = 30, hydroxide |
|---|---|---|---|---|---|
| 3 carbon linker | STW | Amorphous | | Amorphous | |
| 4 carbon linker | CIT-7, STW | STW + Layered | | IWV | |
| 5 carbon linker | RTH | BEA | IWV | IWV | IWV |
| 6 carbon linker | BEA | BEA | | IWV | IWV |

For the 4, 5 and 6 carbon linkers in the aluminosilicate hydroxide reactions the IWV framework was found as the product. This framework has been previously reported using dimethyldiphenylphosphonium in fluoride-mediated, low-water aluminosilicate reactions but takes a long time to form (49 days) and is known as ITQ-27. See, e.g., U.S. Pat. No. 7,527,782. It contains a 2-dimensional channel system of 12-membered rings that also contains 14-membered rings that are only accessible through 14-membered rings. The present method is simpler, and provides for a wider range of high Si:Al compositions.

In the pure-silica, fluoride-mediated reactions at 175° C. a wide variety of products have been observed depending on chain-length and water content (Table 9). Finding BEA as a product in these situations is not surprising as it has been found to form with similar diquats. See, e.g., A. Jackowski, et al., J. Am. Chem. Soc. 131 (2009) 1092-100. Of the other products found in these reactions, STW and RTH have been found to form with pentamethylimidazolium, the similar nature of these diquats to pentamethylimidazolium makes these expected results. Using the diquat with a 4 carbon chain linker (the 3,3'-(butane-1,4-diyl)bis(1,2,4,5-tetramethyl-1H-imidazol-3-ium) dication) led to the formation of CIT-7 in the pure silica syntheses with $H_2O/SiO_2$=4. In some instances STW was found as a competing phase, but it was simple to direct the formation to pure CIT-7 by adding seeds of CIT-7. A representative XRD of calcined, pure-silica CIT-7 produced in fluoride media using the 3,3'-(butane-1,4-diyl)bis(1,2,4,5-tetramethyl-1H-imidazol-3-ium) dication is shown in FIG. 11.

The results of more expanded studies using 3,3'-(butane-1,4-diyl)bis(1,2,4,5-tetramethyl-1H-imidazol-3-ium) dication are shown in Table 9A and Table 9B. In fluoride mediated reactions CIT-7 was produced with gel compositions of Si/Al=25, 50, 100, 250 and in hydroxide mediated reactions CIT-7 was produced with a gel composition of Si/Al=15. With $H_2O/SiO_2$=7, in fluoride mediated reactions, the product was pure-silica STW (Table 9A). This phase has already been reported using several different imidazolium based OSDAs. When the water contents of the reactions were decreased to $H_2O/SiO_2$=4, the OSDA led to the formation of a previously unknown phase. The XPD of the calcined material is shown in FIG. 11. Under these synthesis conditions, CIT-7 was found to crystallize along with STW as a competing phase, so care had to be taken to avoid the formation of STW. Once a pure-phase CIT-7 was obtained, seeds of CIT-7 were used in subsequent reactions to favor its formation over that of STW. In hydroxide mediated reactions, at Si/Al=15 (Table 9B), without the addition of seeds, IWV was found as the product. See FIG. 26A/B. IWV is a 2-dimensional, 12-membered ring material that contains 14-membered rings that are only accessible through 12-membered rings. The aluminosilicate was first reported as ITQ-27, and was made using diphenyldimethylphosphonium as the OSDA. The synthesis is only reported at a difficult to achieve composition of: $1SiO_2:0.014Al_2O_3:0.50Me_2Ph_2POH:0.50HF:4.2H_2O$, and takes 59 days to form, the addition of seeds only shortens this by one week.

Figure 24:
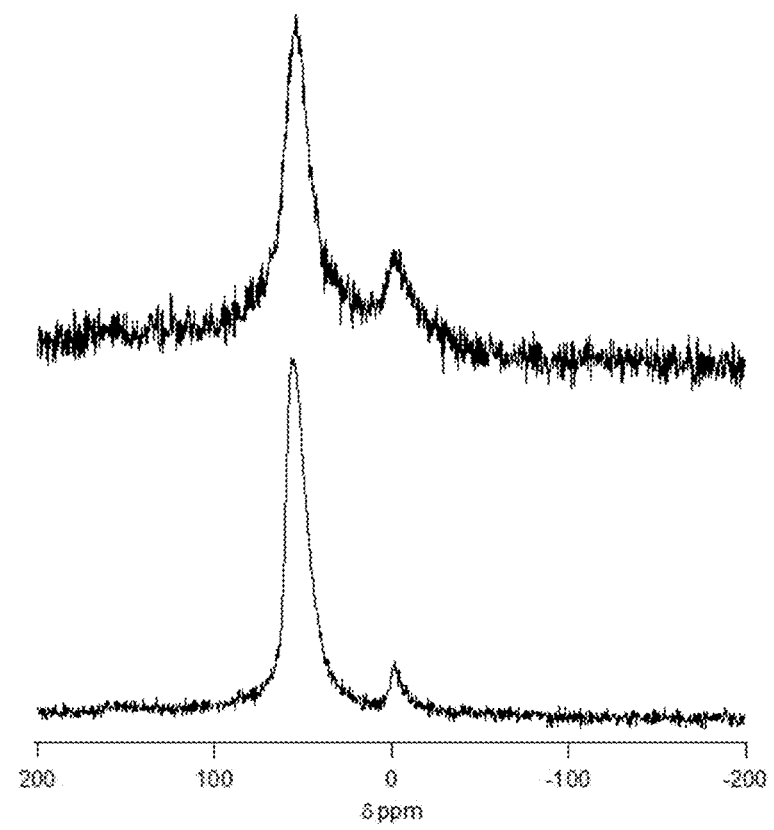
FIG. 24 shows an $^{27}Al$ MAS NMR spectrum of aluminosilicate CIT-7. Upper is fluoride mediated synthesis with gel Si/Al=15 and lower is hydroxide mediated synthesis with gel Si/Al=5. The sample made in hydroxide media is 95% tetrahedral aluminum and the sample made in fluoride media is 88% tetrahedral aluminum.

With the addition of pure-silica CIT-7 seeds to the aluminosilicate syntheses in hydroxide media, CIT-7 was produced instead of IWV. Aluminosilicate CIT-7 could be easily obtained in hydroxide media at gel compositions of Si/Al=5-15. Higher silica compositions led to products containing CIT-7 along with dense phases or ITQ-27. It is likely that optimizing these synthesis conditions will lead to higher silica products using a hydroxide mediated synthesis, however, these compositions are already accessible using the fluoride method. To demonstrate that the aluminum was in the framework, the calcined samples with the highest aluminum contents in both fluoride and hydroxide media were investigated by using $^{27}Al$ NMR (FIG. 24). In the sample prepared in hydroxide media, 95% of the aluminum was tetrahedral, and in the sample synthesized in fluoride media 88% was in tetrahedral coordination. In both of these samples, the majority of the aluminum was in tetrahedral coordination, demonstrating incorporation in the framework. The Si/Al range over which CIT-7 can be produced will allow for a wide variety of catalytic testing to be performed.

Figure 13B:
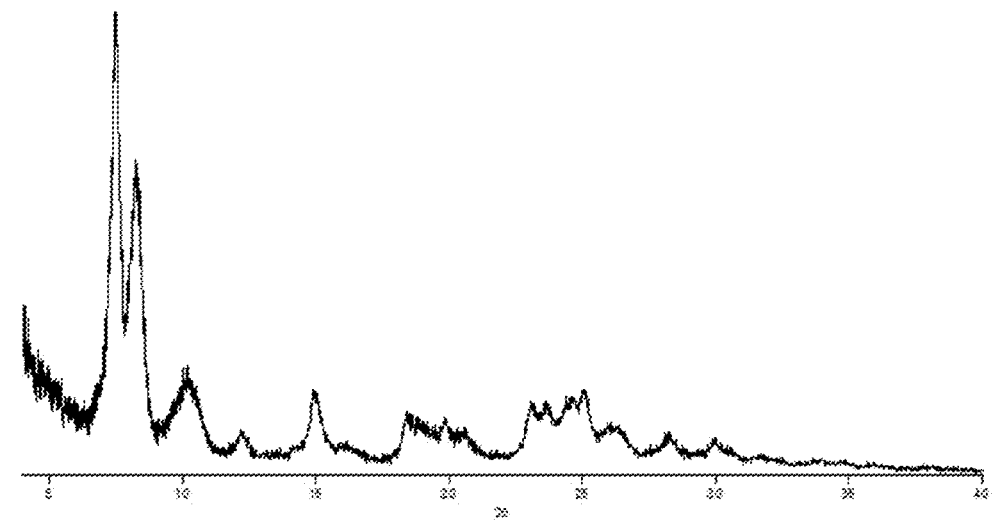

An XRD of calcined aluminosilicate CIT-7 made with gel Si/Al=50 in fluoride media is shown in FIG. 12 and an XRD of the as-made material produced in hydroxide media with gel Si/Al=15 is shown in FIG. 13.

TABLE 9A

Fluoride mediated synthesis results using 4 carbon chain linked diquat

| Gel Ratios | | | | | | | Product Ratios[b] | |
|---|---|---|---|---|---|---|---|---|
| Si/Al | Si/Ti | $H_2O/SiO_2$ | Seeds | Temp (° C.) | Time (days) | Result | Si/Al | Si/Ti |
| ∞ | — | 4 | None | 175 | 8 | STW[a] | — | — |
| ∞ | — | 4 | None | 175 | 6 | STW + CIT-7[3] | — | — |
| ∞ | — | 4 | None | 175 | 6 | CIT-7[a] | — | — |
| ∞ | — | 4 | Silica CIT-7 | 175 | 6 | CIT-7 | — | — |
| ∞ | — | 7 | None | 175 | 6 | STW | — | — |
| 15 | — | 4 | Silica CIT-7 | 175 | 5 | CIT-7 | 10 | — |
| 15 | — | 4 | Silica CIT-7 | 175 | 5 | CIT-8P | — | — |
| 20 | — | 4 | None | 175 | 20 | CIT-7 | 14 | — |
| 20 | — | 4 | None | 175 | 12 | CIT-7 | 13 | — |
| 25 | — | 4 | Silica CIT-7 | 175 | 5 | CIT-7 | 15 | — |
| 25 | — | 4 | Silica CIT-7 | 175 | 5 | CIT-7 | 17 | — |
| 25 | — | 4 | Silica CIT-7 | 175 | 6 | CIT-7 | 14 | — |
| 50 | — | 4 | None | 175 | 18 | CIT-7 | 27 | — |
| 50 | — | 4 | Silica CIT-7 | 175 | 4 | CIT-7 | 28 | — |
| 100 | — | 4 | Silica CIT-7 | 175 | 4 | CIT-7 | 36 | — |
| 250 | — | 4 | Silica CIT-7 | 175 | 4 | CIT-7 | 225 | — |
| — | 50 | 4 | Silica CIT-7 | 175 | 7 | CIT-7 | — | 63 |
| — | 100 | 4 | Silica CIT-7 | 175 | 7 | CIT-7 | — | 88 |

[a]Since STW and CIT-7 were competing products some syntheses produced pure phase versions (per XPD) of those molecular sieves
[b]Determined using EDS of calcined material

TABLE 9B

Hydroxide mediated synthesis results using 4 carbon chain linked diquat.

| Gel Si/Al | Gel Na/Si | Gel ROH/Si | Gel $H_2O$/Si | Temp (° C.) | Seeds | Time (days) | Product | Product Si/Al |
|---|---|---|---|---|---|---|---|---|
| 5[a] | 0.25 | 0.16 | 30 | 160 | Silica CIT-7 | 35 | CIT-7 | 9 |
| 10[a] | 0.25 | 0.16 | 30 | 160 | None | 20 | CIT-7 | 12 |
| 15[a] | 0.16 | 0.16 | 30 | 160 | None | 35 | IWV | |
| 15[a] | 0.16 | 0.16 | 30 | 160 | Silica CIT-7 | 10 | CIT-7 | 18.4 H+ form |
| 15[a] | 0.16 | 0.16 | 30 | 160 | Silica CIT-7 | 10 | CIT-7 | 9 |
| 30[b] | | | | 175 | None | 18 | IWV | 29 |
| 30[b] | | | | 175 | Silica CIT-7 | 23 | IWV + CIT-7 | |

[a]Made using Ludox AS-40 and sodium aluminate
[b]Made from CBV760

Example 8.2

Structure of CIT-7

Figure 14:
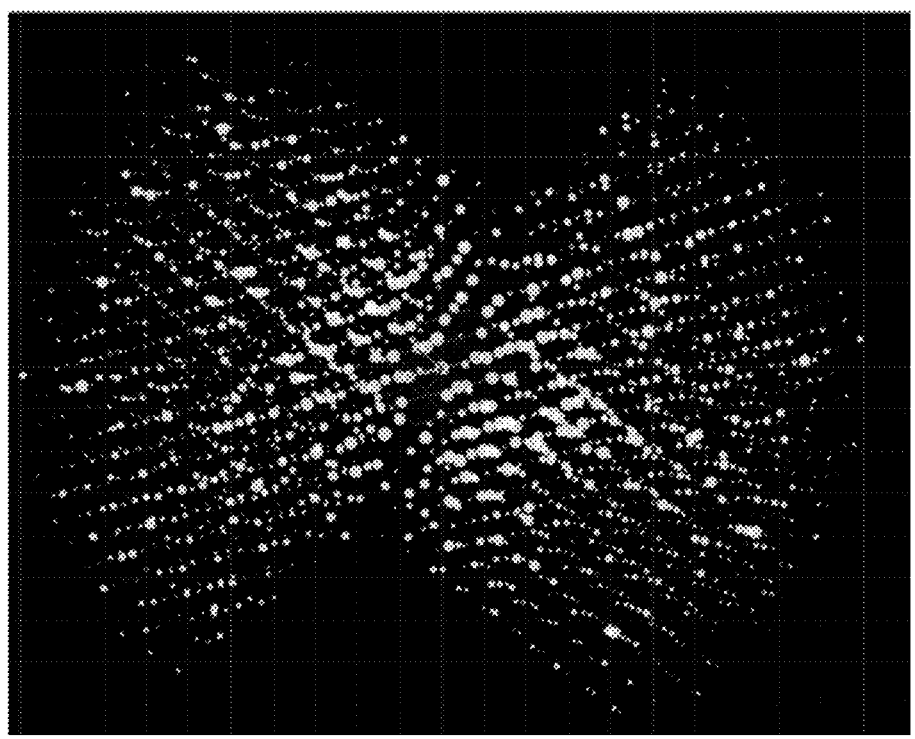
FIG. 14 shows the 3-dimensional ED tomography data used to solve the structure of CIT-7.
Figure 15:
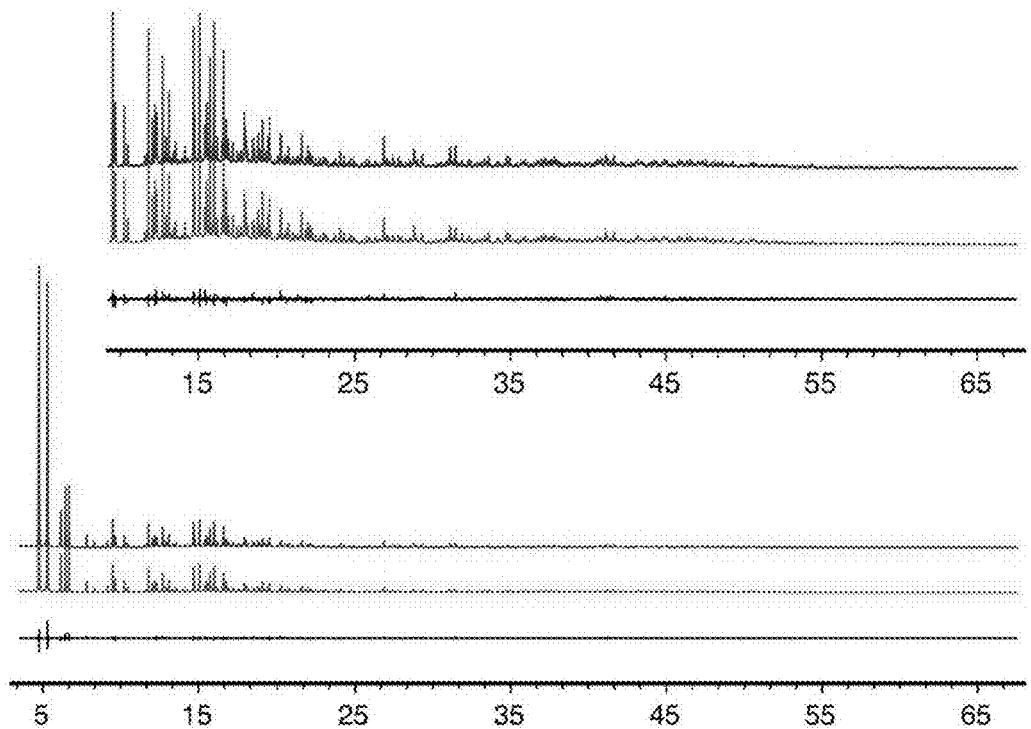
FIG. 15 shows the Rietveld refinement fit (Rwp=0.077; Rexp=0.068; RF=0.055). Upper traces: synchrotron data; Middle traces: calculated data; Lower traces: difference. Upper inset is magnified 6 times.
Figure 16:
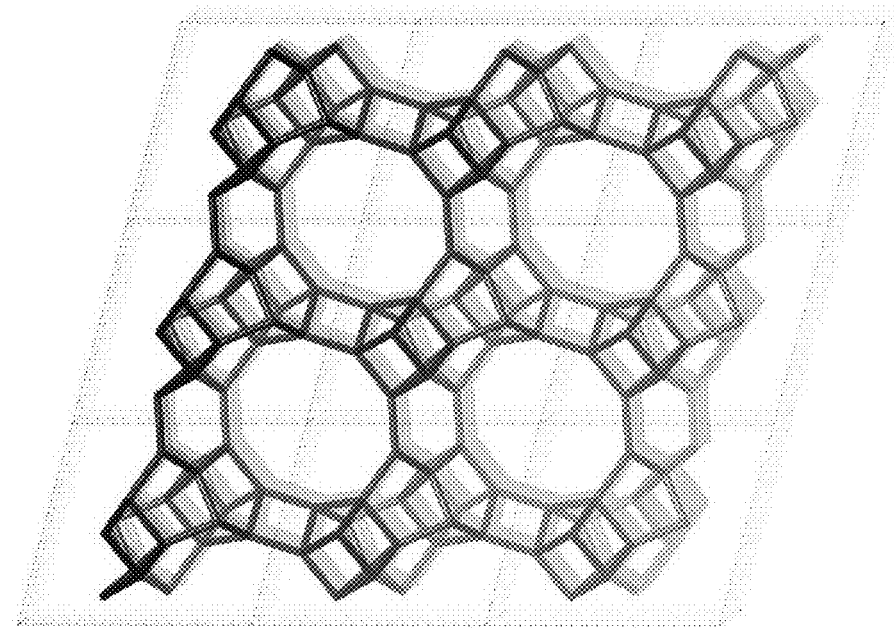
FIG. 16 shows a view along the 10-membered ring channel system of CIT-7.
Figure 17:
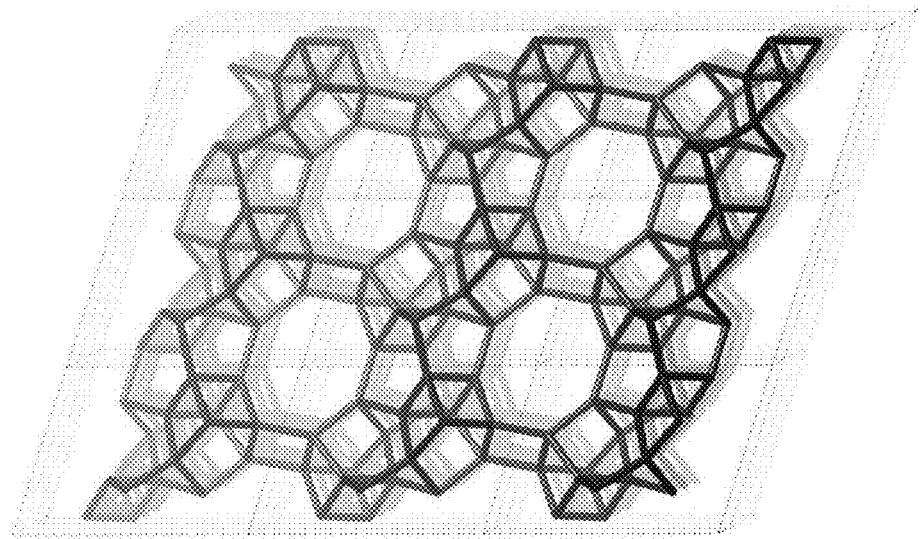
FIG. 17 shows a view along the 8-membered ring channel system of CIT-7.

The structure of pure silica CIT-7 was solved by 3-dimensional electron diffraction tomography data (FIG. 14), refined by synchrotron X-ray powder diffraction data (FIG. 15). There are 10 unique/independent T atoms in the unit cell and the material has P-1 symmetry. The new microporous material structure has a 2-dimensional 10-/8-ring channel system, with distorted 8-ring channels. The channel dimensions of the material are 6.2 Å*5.1 Å and 5.5 Å*2.9 Å for the 10-membered rings and 8-membered rings, respectively, and views of the channel systems are shown in FIG. 16 and FIG. 17.

Figure 20:
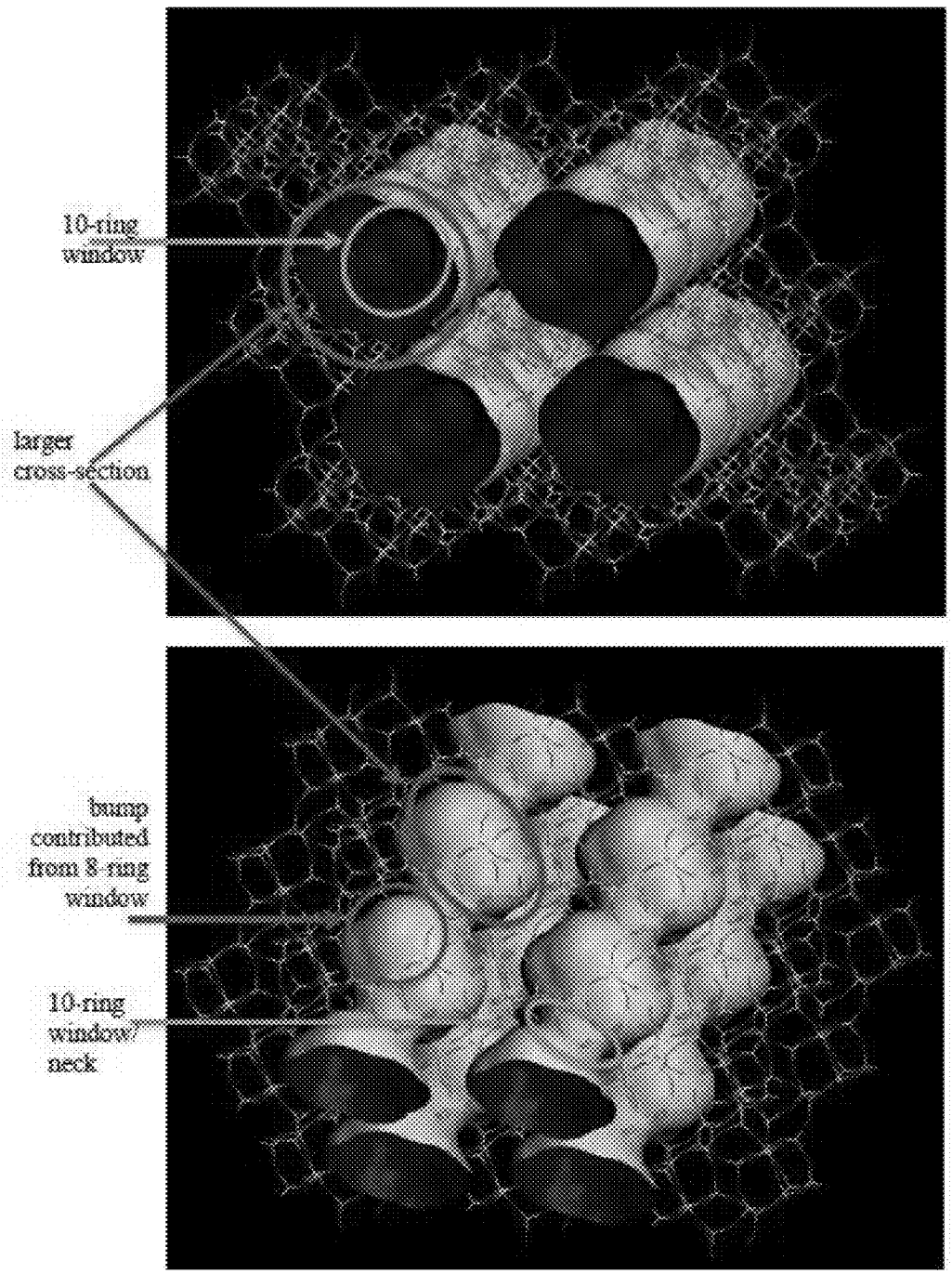
FIG. 20 show the isosurface contours of CIT-7

The structure of CIT-7 is comprised of two different secondary building units. The first is the previously observed $[4^25^46^2]$ mtw unit. The second building unit is a new $[4^45^2]$ building unit comprised of four 4-rings and two 5-rings and are denoted here cse. This cse building unit has not been previously reported. Both building units are shown in FIG. 18. The two building units then assemble to form the 3-dimensional structure of CIT-7, shown in FIG. 19. Oval 8-rings are created (2.9 Å×5.5 Å opening, with the oxygen diameter of 2.70 Å subtracted). The layer that has 8-rings, could again link to itself and form 10-ring channels (5.1 Å×6.2 Å opening, with the oxygen diameter of 2.70 Å subtracted) that are running perpendicular to the layer and intersected by 8-ring channels. At each intersection, a [$4^8 5^4 6^8 8^2 10^2$] cavity is created (FIG. 19). Isosurface contours of the final material are shown in FIG. 20. One of the interesting features of the framework, highlighted in FIG. 20, are the bumps inside the 10-ring system that come from the 8-rings.

It should be noted that the structure of CIT-7 is not predicted in any hypothetical zeolite framework databases as these databases only contain structures having less than 10 unique T atoms per unit cell. The optimized framework energy of pure-silica CIT-7 relative to α-quartz, i.e., 16.63 kJ/mol per Si atom, clearly demonstrates that this structure is energetically favorable.

Example 8.3

Pure Silicate CIT-7 Characterization

Figure 21:
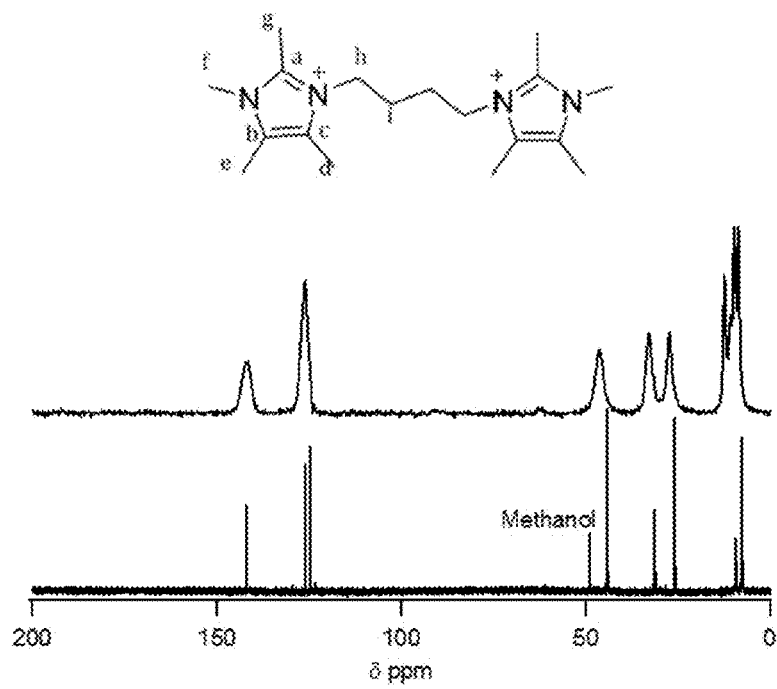
FIG. 21 shows the $^{13}C$ CP-MAS NMR spectrum of as-made CIT-7 (upper) showing the occluded 3,3'-(butane-1,4-diyl)bis(1,2,4,5-tetramethyl-1H-imidazol-3-ium) cation along with peak assignments and comparison to the liquid $^{13}C$ NMR spectrum (lower).
Figure 22:
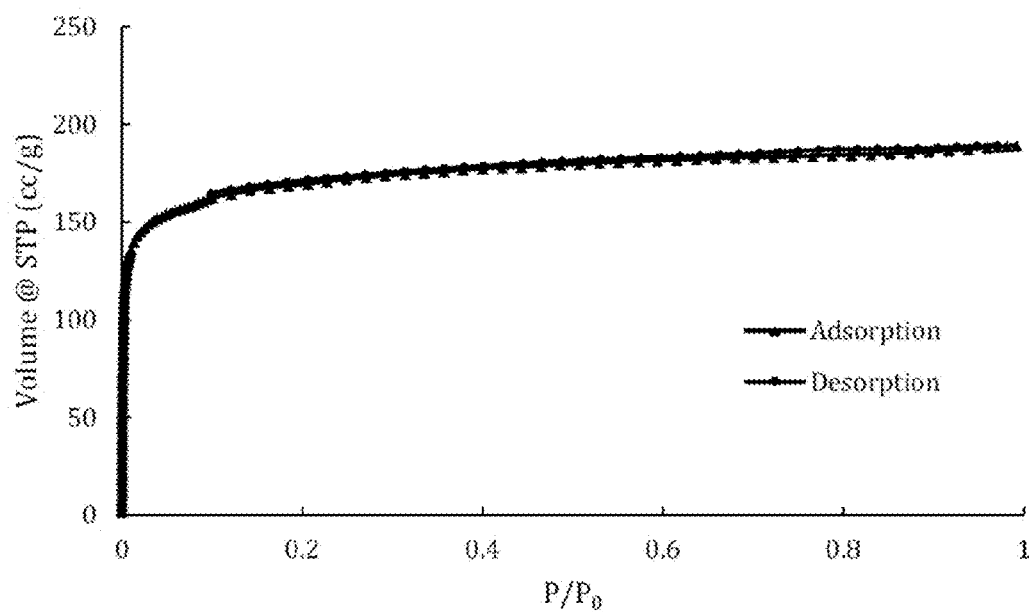
FIG. 22 shows an Argon isotherm of CIT-7, micropore volume determined to be 0.19 cm$^3$/g (t-plot method).

The pure silica CIT-7 produced with the 3,3'-(butane-1,4-diyl)bis(1,2,4,5-tetramethyl-1H-imidazol-3-ium) dication has been characterized using $^{13}$C CP-MAS NMR, $^{29}$Si MAS NMR and Argon adsorption. The $^{13}$C CP-MAS NMR of the as-made material (FIG. 21) showed that the 3,3'-(butane-1,4-diyl)bis(1,2,4,5-tetramethyl-1H-imidazol-3-ium) dication was occluded intact in the framework, demonstrating that it was not a decomposition product that formed the CIT-7. The thermogravimetric analysis showed a weight loss of 22.5 wt %, which corresponds to 1 molecule of OSDA and 2 fluoride anions per unit cell. The Argon isotherm of the calcined material (FIG. 22) gave a micropore volume of 0.19 cm$^3$/g, which is consistent with the structure solution. An $^{19}$F NMR spectrum of the as-made material revealed resonances at −45 ppm and −128 ppm. The resonance at −128 ppm can be assigned to a small amount of SiF$_6$ in the sample, and the resonance at −45 ppm is consistent with fluoride being occluded in a pure-silica material. The $^{29}$Si NMR spectrum of the calcined material is shown in FIG. 23. The spectrum was deconvoluted using Lorentzian lineshapes and the peak fit is shown in FIG. 24 along with the extracted parameters in Table 10.

Example 8.5

X-Ray Analysis of CIT-7

The structure of the calcined, pure-silica material was determined using a combination of synchrotron XPD and RED data. The calcined, pure-silica CIT-7 powder sample was packed into a 0.5 mm glass capillary and sealed. High-resolution XPD data were then collected on the 2-1 Powder Diffraction beamline at the Stanford Synchrotron Radiation Lightsource (SSRL).

The XPD pattern could be indexed with a triclinic unit cell (a=13.020 Å, b=11.205 Å, c=9.375 Å, α=92.8°, β=107.2°, γ=103.3°), using the program TREOR (as described in P. E. Werner, et al., *J. Appl. Cryst.*, 1985, 18, 367-370) implemented in the software CMPR (as described in B. H. Toby, *J. Appl. Cryst.*, 2005, 38, 1040-1041). No indexing solutions on higher symmetry crystal systems could be found. Individual reflection intensities were extracted from the powder pattern to a minimum d-spacing of 0.90 Å (ca. 67.5° 2θ) using the program EXTRACT (described in Baerlocher, C. EXTRACT. A Fortran program for the extraction of integrated intensities from a powder pattern; Institut für Kristallographie, ETH Zürich, Switzerland, 1990) in the XRS-82 suite of programs (see Baerlocher, C.; Hepp, A. *XRS*-82. *X-ray Rietveld Syst.* Inst. für Krist. ETH Zürich, Switzerland, 1982). Structure solution using these data was then attempted using both the zeolite-specific structure-solution program Focus (R. W. Grosse-Kunstleve, et al., *J. Appl. Crystallogr.*, 1997, 30, 985-995), and the powder charge-flipping algorithm (C. Baerlocher, et al., *Z. Kristallogr.*, 2007, 222, 47-53) in the program Superflip (L. Palatinus and G. Chapuis, *J. Appl. Cryst.*, 2007, 40, 786-790.). Unfortunately, neither approach yielded a reasonable structural model.

Therefore, the RED technique was applied to the CIT-7 sample to obtain 3-dimensional single-crystal data. Two independent RED data sets were collected on two tiny crystallites, both could be indexed on triclinic unit cells that are similar to the one found for the XPD pattern. Reflection intensities (ca. 1.0 Å resolution) were then extracted for each data set using the RED software, and were further analyzed by the program Triple (*Triple* http//www.calidris-em.com/triple.php. Accessed Dec. 8, 2014). Although both datasets gave data completeness of only ca. 55%, one did provide better quality over the other, i.e., the agreement factor of the reflection intensities for Friedel pairs is 11.7% versus 22.1%. Therefore, a structure solution attempt using the better RED dataset for Focus structure solution (assuming the centrosymmetric space group P-1) was performed. Many framework topologies were proposed by Focus, but none were chemically reasonable. Luckily, the two available RED

TABLE 10

Deconvolution parameters determined from $^{29}$Si MAS NMR Spectrum of calcined pure silica CIT-7 along with the normalized peak areas and assigned T sites

| Location | Normalized Area | Assigned T site | Average Si—O—Si Angle$^a$ |
| --- | --- | --- | --- |
| −115.6 | 0.92 | Si10 | 152.2 |
| −115.2 | 2.14 | Si3 + Si8 | 151.7, 151.6 |
| −111.3 | 1.97 | Si1 + Si5 | 149.4, 149.1 |
| −111.0 | 1.06 | Si6 | 148.3 |
| −109.6 | 0.97 | Si9 | 147.2 |
| −109.3 | 0.88 | Si4 | 147.2 |
| −108.8 | 1.28 | Si7 | 146.8 |
| −106.7 | 1.00 | Si2 | 145.6 | datasets covered different areas of reciprocal space, and therefore by merging them, the data completeness could be improved to 86%. With the merged dataset included in the Focus runs, the structure solution became surprisingly straightforward. A model with 10 unique framework T-atoms, clearly showing a 2-dimensional channel system of intersecting 10- and 8-rings, was revealed. Indeed, this was the only solution proposed by the structure solution program.

The geometry of the CIT-7 framework structure model from the Focus run was optimized using the program DLS-76 (Baerlocher, C.; Hepp, A.; Meier, W. M. DLS-76; Inst. für Krist. ETH Switzerland, 1976), and then served as a starting point for Rietveld refinement, using the synchrotron XPD data. Geometric restraints were applied on the bond distances and bond angles of the framework atoms, and their positions refined. These restraints were imposed throughout the refinement, but their relative weighting with respect to the XPD data was reduced as the refinement progressed. The structural model finally converged with $R_F$=0.055 and $R_{wp}$=0.077 ($R_{exp}$=0.068). All atoms were refined isotropically using scattering factors for neutral atoms. The displacement parameters for similar atoms were constrained to be equal to keep the number of parameters to a minimum. Details of the refinement and selected bond distances and angles are given in Table 11. The fit of the profile calculated from the final model to the experimental data is shown in FIG. 15.

TABLE 11

Crystallographic data for pure-silica CIT-7.

| Chemical composition | [$Si_{20}O_{40}$] |
|---|---|
| Unit cell | |
| a (Å) | 13.0187(1) |
| B (Å) | 11.2063(1) |
| c (Å) | 9.3758(1) |
| α (°) | 92.8224(6) |
| β (°) | 107.2048(5) |
| γ (°) | 103.2565(5) |
| Space group | P-1 |
| Number of observations | 8001 |
| Number of contributing reflections | 3703 |
| Number of geometric restraints | 120 |
| Number of structural parameters | 98 |
| Number of profile parameters | 12 |
| $R_F$ | 0.041 |
| $R_{wp}$ | 0.077 |
| $R_{exp}$ | 0.068 |
| Selected bond distances (Å) and angles (°) | |
| Si—O (Å)   min: 1.59 | max: 1.62   avg: 1.61 |
| O—Si—O (°)  min: 106.4 | max: 112.2  avg: 109.5 |
| Si—O—Si (°) min: 142.1 | max: 157.3  avg: 148.9 |

Example 8.4

Titanosilicate CIT-7

Figure 25:
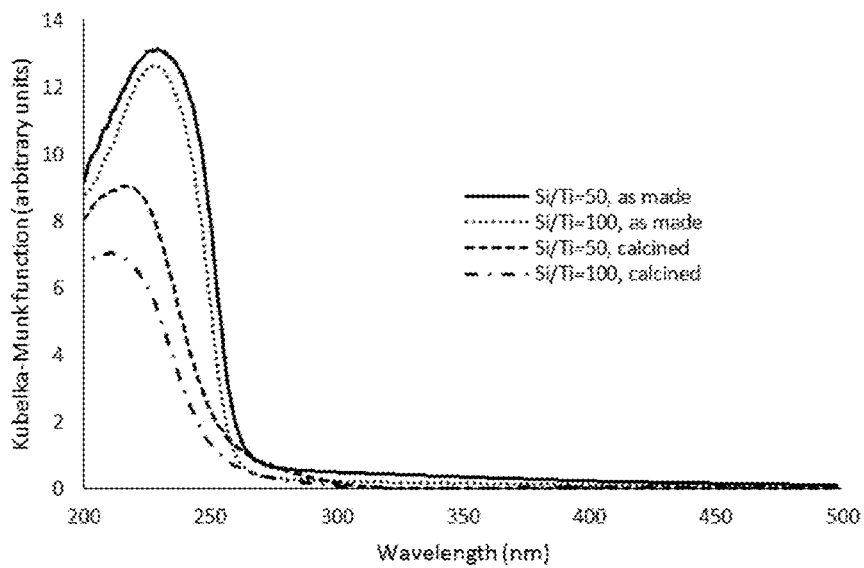
FIG. 25 shows a UV-VIS spectrum of titanosilicate CIT-7.

The ability of the CIT-7 framework to incorporate heteroatoms besides aluminum was tested by adding titanium to fluoride syntheses. In the titanosilicate material, both Si/Ti=50 and 100 were synthesized. DRUV of the as-made and calcined titanosilicate materials was used to show that the titanium was present in tetrahedral coordination (FIG. 25), indicating framework incorporation.

Example 8.5

Comparison with Other Structures

The structure solution of CIT-7 shows that it is a unique framework comprised of a 2-dimensional system of 10- and 8-membered rings, where the 8-membered rings are elliptical and the 10-membered rings contain "bumps" in them caused by the 8-membered rings. Due to this unique pore system it is expected that this material will exhibit unique properties.

Four other zeolite frameworks, i.e., FER (e.g., NU-23, ZSM-35), MFS (e.g., ZSM-57), RRO (e.g., RUB-41) and STI (e.g., TNU-10, SSZ-75), have a 2-dimensional 10-/8-ring channel systems. CIT-7 distinguishes itself from these known materials by some unique structural features. CIT-7 is the only system that has a large cavity in the intersection region. The maximum included sphere diameter for the idealized CIT-7 framework (i.e., the one after distance-angle least-square refinement) is calculated to be 7.91 Å, significantly larger than those for the other four idealized frameworks (Table 12). Also, it should also be noted that CIT-7 can be made across a very wide Si/Al ratio (9-∞) as well as a titanium (and we suspect other heteroatoms) containing material. This compositional flexibility, when combined with the medium-/small-pore channels and intersecting cavities, could be of interest in a broad spectrum of applications.

TABLE 12

Comparison of the channel and pore characteristics for the five 2-D 10-/8-ring zeolites. For the 4 known zeolite frameworks, the channel characteristics are taken from the literature, and the pore characteristics are taken from the Database of Zeolite Structures. The channel characteristics for CIT-7 are calculated using the program "Sphere Viewer". All data are in Å.

| Framework | $D_M$ | $D_a$ | $D_b$ | $D_c$ | Material | 10-MR opening | 8-MR opening |
|---|---|---|---|---|---|---|---|
| Idealized CIT-7 | 7.91 | 1.87 | 2.92 | 4.67 | CIT-7 | 5.1 × 6.2 | 2.9 × 5.5 |
| MFS | 6.71 | 5.31 | 3.14 | 1.51 | ZSM-57 | 5.1 × 5.4 | 3.3 × 4.8 |
| FER | 6.25 | 1.50 | 3.34 | 4.63 | Ferrierite | 4.2 × 5.4 | 3.5 × 4.8 |
| STI | 6.23 | 4.88 | 2.90 | 1.79 | SSZ-75 | 4.7 × 5.0 | 2.7 × 5.6 |
| RRO | 4.40 | 4.03 | 1.48 | 3.07 | RUB-41 | 4.0 × 6.5 | 2.7 × 5.0 |

Note:
$D_M$ means the maximum included sphere diameters, $D_a$, $D_b$ and $D_c$ are the maximum free sphere diameters that can diffuse along a-, b- and c-axis, respectively.

Example 8.6

Proposed Uses of Crystalline Solids Containing 8-/10-MRs

Several systems comprising 2-dimensional systems of 10- and 8-membered rings have been proposed for various applications such as carbonylation, NOx reduction, dewaxing, cracking, isomerization, reforming, methanol to olefins reaction, oligmerization, amination of alcohols, hydroconversion and gas separations and detailed applications and references for several of the frameworks are given in Table 13. CIT-7 is expected to be useful in each of these applications, and the use of this material in these applications is considered within the scope of the present invention. That is, various embodiments of the present invention include those where the named reaction is mediated by CIT-7; i.e., individual embodiments provide for effecting the named reaction by contacting an appropriate feedstock with the CIT-7-type material, under conditions known to be effective for the transformation.

TABLE 13

Expected uses of microporous material frameworks with 2-dimensional 10-/8-membered ring systems

| Framework | Use | As Described in: |
|---|---|---|
| FER (NU-23, ZSM-35) | Low temperature carbonylation of DME with CO | Y. Román-Leshkov, et al., *J. Phys. Chem. C.* 115 (2011) 1096-1102. |
| | NOx reduction with methane | Y. Li, et al., *Appl. Catal. B Environ.* 3 (1993) L1-L11. |
| | Dewaxing, cracking, isomerization and reforming | U.S. Pat. No. 4,925,548. (1990) |
| | Polymerization, aromatization, cracking, hydrocracking, converting light aliphatics to aromatics | U.S. Pat. No. 4,016,245. (1977) |
| MFS (ZSM-57) | Cracking, dehydrogenating, converting paraffins to aromatics, MTO, isomerizing xylenes, disproportionating toluene, alkylating aromatic hydrocarbons, upgrading hydrocarbons | U.S. Pat. No. 4,873,067. (1989) |
| | 1-Butene Skeletal Isomerization and n-Octane Cracking | S. Lee, et al., *J. Catal.* 196 (2000) 158-166 |
| | Alkene oligomerization | J.A. Martens, et al., *Angew. Chemie.* 39 (2000) 4376-4379 |
| RRO (RUB-41) | Synthesis of methylamines by the amination of methanol | B. Tijsebaert, et al., *J. Catal.* 278 (2011) 246-252 and B. Yilmaz, et al., *Chem. Commun.* (Camb). 47 (2011) 1812-4. |
| | Separation and sorption of C3-C6 alkanes | Y.X. Wang, et al., *Chem. Mater.* 17 (2005) 43-49 |
| | Decane hydroconversion | B. Yilmaz, et al., Chem. Commun (Camb). 47 (2011) 1812-4. |
| STI (TNU-10, SSZ-75) | Skeletal isomerization of 1-butene to isobutene and the selective reduction of NO with methane | S.B. Hong, et al., *J. Am. Chem. Soc.* 126 (2004) 5817-26. |
| | Gas separations, converting oxygenates (e.g. methanol) to olefins, making small amines, NOx reduction, cold start hydrocarbon trap | U.S. Pat. No. 7,713,512. (2010) |

Example 9.1

Synthesis of High Silica Zeolites with the HEU Topology: Introduction

New methods have been discovered to produce zeolites with the HEU framework topology with higher than previously reported silica to alumina ratios. This material, denoted herein as CIT-8, can be prepared by both direct synthesis in hydroxide media or as a topotactic condensation product, where the layered precursor is made in fluoride media and denoted CIT-8P. These materials are stable to calcination and subsequent ion exchange (if applicable) and have micropore volume accessible to nitrogen.

Zeolites with the HEU framework topology exist as both natural minerals as well as synthetic analogs. The heulandite framework consists of a two dimensional channel system. In the [001] directing there are 10-membered rings (MRs) as well as 8-MRs. Additionally, there is another set of 8-MRs along with [100] direction (See Table 1).

Methods to prepare high silica heulandite, denoted CIT-8, are reported herein. In one method, CIT-8 is prepared via topotactic condensation of a layered aluminosilicate material containing an organic structure directing agent. This layered material is denoted CIT-8P. CIT-8 can also be prepared by direct synthesis in hydroxide media using an organic structure directing agent (OSDA)

Example 9.2

Synthesis of High Silica Zeolites with the HEU and IWV Topologies: Results

The diquat used to prepare solids having HEU topology, 3,3'-(butane-1,4-diyl)bis(1,2,4,5-tetramethyl-1H-imidazol-3-ium), is also described above in the context of CIT-7.

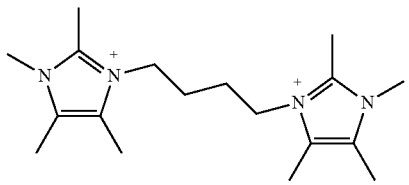

However, it was found that a certain set of conditions led to the formation of a new, layered material, denoted CIT-8P. A representative powder x-ray diffraction pattern (PXRD) of this material is shown in FIG. 27. This material was produced in low-water, fluoride-mediated aluminosilicate reactions. The general composition of these reactions was 1 $SiO_2$:x Al:0.5 ROH:0.5 HF:4$H_2O$ and x was varied to give a range of Si/Al ratios. With Si/Al=15 and 20, pure phase CIT-8P was obtained. However, at Si/Al=30, 50 and 100 the product was a mixture of CIT-8P and CIT-7. When CIT-8P was calcined a new phase was found, a representative XRD pattern is shown in FIG. 28. This material was identified as having the HEU framework topology. The material with Si/Al=20 in the gel was found to have a product Si/Al=11.5 and the nitrogen adsorption isotherm gave a micropore volume of 0.096 cc/g (t-plot method).

In changing the OSDA by changing the length of the linker between the imidazolium groups it was found that diquats of other linker lengths could also form CIT-8P and CIT-8. Results of the various synthesis conditions with the diquats are shown in Table 14.

PREFER, which has been previously synthesized (Schreyeck, L, et al., *Microporous Mater.* 1996, 6, 259).

The four carbon diquat also led to a wide variety of products. This diquat was shown to make CIT-7 in Example 8. In addition to CIT-7, this diquat also led to CIT-8P. Another product with this diquat is denoted "Layered+ STW." This material is likely pure silica STW plus some layered material made from the organic which disappears after calcination.

TABLE 14

Diquat synthesis results in fluoride media, 175° C.:

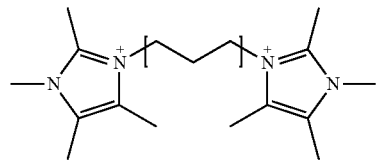

n = 3, 4, 5, 6, 8, 10

| Linker length | Pure Pure Si, $H_2O/SiO_2 = 4$ | Pure Si, $H_2O/SiO_2 = 7$ | $H_2O/SiO_2 = 4$, Si/Al = 20 | $H_2O/SiO_2 = 7$, Si/Al = 20 | $H_2O/SiO_2 = 4$, Si/Al = 50 | $H_2O/SiO_2 = 7$, Si/Al = 50 |
|---|---|---|---|---|---|---|
| 3 | STW | Amph | PREFER | CIT-8P + PREFER | CIT-7 | dense |
| 4 | CIT-7, STW + CIT-7 | Layered + STW | CIT-8P, CIT-7 | CIT-7 | CIT-7 | CIT-7 |
| 5 | RTH, Layered STW | BEA | CIT-8P | CIT-8P | CIT-7 + CIT-8P | IWV |
| 6 | BEA | BEA | CIP-8P | BEA | Unknown | STF |
| 8 | BEA | BEA | BEA | dense | BEA | BEA |
| 10 | BEA | MTW | BEA | BEA | BEA | BEA |

In general the longest diquats gave products which are commonly found in microporous materials syntheses such as MTW and BEA. However, the diquats with carbon chains of 3, 4, and 5 carbon atoms gave a wide range of interesting products. In pure silica media the 3 carbon diquat gave STW as a product. Under different conditions this diquat also gave Additional experiments showed that the window for producing the HEU material is narrow, at least for the tested diquat, as shown in Table 15:

TABLE 15

Diquat synthesis results in fluoride media, using the diquat with the four carbon chain linker:

for the system 1 $SiO_2$:x Al:0.5 ROH:0.5 HF:4 $H_2O$:

| Gel Si/Al | Gel Na/Si | Gel ROH/Si | Gel $H_2O$/Si | Temp, ° C. | Seeds | Time (days) | Product | Product Si/Al |
|---|---|---|---|---|---|---|---|---|
| 5[a] | 0.25 | 0.16 | 30 | 160 | None | 43 | HEU | 7.3 |
| 5[a] | 0.25 | 0.16 | 30 | 160 | Silica CIT-7 | 35 | CIT-7 | 9 |
| 5[a] | 0.25 | 0.16 | 30 | 160 | HEU | 24 | HEU | |
| 7.5[a] | 0.25 | 0.16 | 30 | 160 | HEU | 20 | CIT-7 | |
| 10[a] | 0.25 | 0.16 | 30 | 160 | HEU | 20 | CIT-7 | |
| 10[a] | 0.25 | 0.16 | 30 | 160 | HEU | 20 | CIT-7 | 12 |
| 15[a] | 0.16 | 0.16 | 30 | 160 | None | 35 | CIT-7 | |
| 15[a] | 0.16 | 0.16 | 30 | 160 | Silica CIT-7 | 10 | IWV | 18.4 prot.form |
| 15[a] | 0.16 | 0.16 | 30 | 160 | Silica CIT-7 | 10 | CIT-7 | 9 |
| 30[b] | | | | 175 | None | 18 | IWV | 29 |
| 30[b] | | | | 175 | Silica CIT-7 | 23 | IWV + CIT-7 | |

TABLE 15-continued

Diquat synthesis results in fluoride media, using the diquat with the four carbon chain linker:

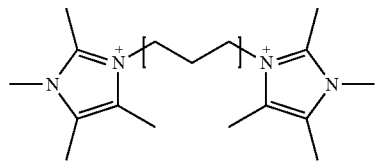

| | | | for the system 1 SiO$_2$:x Al:0.5 ROH:0.5 HF:4 H$_2$O: | | | | |
|---|---|---|---|---|---|---|---|
| Gel Si/Al | Gel Na/Si | Gel ROH/Si | Gel H$_2$O/Si | Temp, ° C. | Seeds | Time (days) | Product | Product Si/Al |

[a] Made using Ludox AS-40 and sodium aluminate
[b] Masde from CBV760

The five carbon diquat led to a wide variety of products. In the low-water, pure-silica case both RTH and layered STW were observed as products. The material called layered STW, is different than the one formed with the four carbon diquat, but is also likely pure silica STW plus some layered material made from the organic which disappears after calcination. Besides CIT-7 and CIT-8P the other product formed by the five carbon diquat was IWV. IWV is a 2-dimensional 12-membered ring material that contains 14-membered rings which are only accessible through 12-membered rings. This aluminosilicate was first reported as ITQ-27, and was made using diphenyldimethylphosphonium as the OSDA. The synthesis is only reported at a difficult to achieve composition of 1SiO$_2$:0.014Al$_2$O$_3$: 0.50Me$_2$Ph$_2$POH:0.50HF:4.2H$_2$O, and takes 59 days to form, which can only be shortened by one week using seeds.

In hydroxide media using the 4 carbon chain diquat, CIT-8 was found to form by direct synthesis at low Si/Al ratios. With a gel composition of 1 SiO$_2$:0.1 Al$_2$O$_3$:0.125 Na$_2$O:0.16 R$_{1/2}$OH:30 H$_2$O, HEU was found as the product after 43 days, which could be shortened to 24 days by adding seeds, a representative PXRD of the calcined material is shown in FIG. 29. This material was stable to ammonium exchange and subsequent calcination and it was found that in proton form the material had a nitrogen adsorption isotherm micropore volume of 0.095 cc/g (t-plot method). The material had an organic content of 8.4 wt % and a product Si/Al=7.3, high than what is reported for any previous HEU syntheses. When the Si/Al ratio was increased above about 5 in hydroxide media, CIT-7 was found as the product instead of HEU, even when seeds were used.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A crystalline microporous solid of CIT-7 topology having micropores and comprising:
   (a) (i) silicon oxide, germanium oxide, or combination thereof; and optionally
   (ii) aluminum oxide, boron oxide, gallium oxide, hafnium oxide, iron oxide, tin oxide, titanium oxide, indium oxide, vanadium oxide, zirconium oxide, or combination or mixture thereof; and optionally
   (b) an organic structure directing agent occluded within at least some of the micropores, the organic structure directing agent comprising:
   (i) a linked pair of quaternary imidazolium cations of a structure:

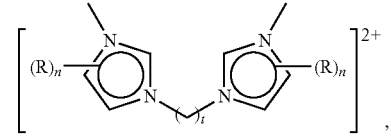

or
   (ii) an imidazolium cation comprising methyl and ethyl groups and having a C/N+ ratio in a range of from 6:1 to 10:1;
   wherein t is 3, 4, 5, or 6; and
   R is independently methyl or ethyl, and n is independently 1, 2, or 3; wherein
   the crystalline microporous solid of CIT-7 topology exhibits a powder XRD pattern having at least five of the characteristic peaks at 7.43±0.15° 2-Theta, 8.26±0.15° 2-Theta, 9.62±0.15° 2-Theta, 10.08±0.15° 2-Theta, 10.48±0.15° 2-Theta, 14.83±0.15° 2-Theta, 18.42±0.15° 2-Theta, 22.96±0.15° 2-Theta, 23.55±0.15° 2-Theta, or 25.02±0.15° 2-Theta.

2. The crystalline microporous solid of CIT-7 topology of claim 1, wherein at least some of the micropores are occluded with linked pairs of quaternary imidazolium cations having a structure:

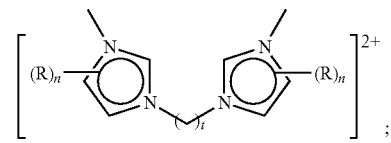

wherein t is 3, 4, 5, or 6;
   R is independently methyl or ethyl, and n is independently 1, 2, or 3.

3. The crystalline microporous solid of CIT-7 topology of claim 2, wherein the linked pairs of quaternary imidazolium cations have a structure of:

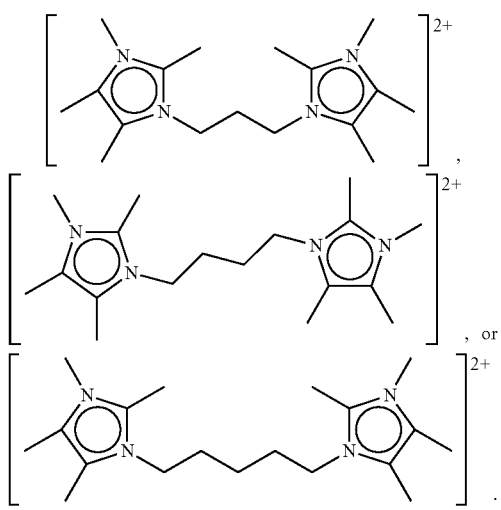

4. The crystalline microporous solid of CIT-7 topology of claim 1, wherein at least some of the micropores are occluded with an organic complex comprising imidazolium cations comprising methyl and ethyl groups and having a C/N+ ratio in a range of from 6:1 to 10:1.

5. The crystalline microporous solid of CIT-7 topology of claim 4, wherein the imidazolium cations are described by a resonance form that is:

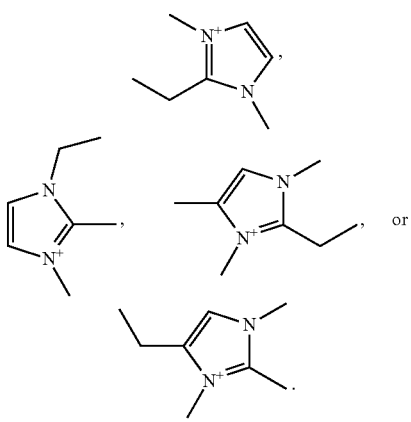

6. A crystalline microporous solid comprising (a) silicon oxide, germanium oxide, or combination thereof and optionally (b) aluminum oxide, boron oxide, gallium oxide, hafnium oxide, iron oxide, tin oxide, titanium oxide, indium oxide, vanadium oxide, zirconium oxide, or combination thereof and having a pore structure with 8-membered and 10-membered rings, the calcined crystalline microporous solid containing practically no organic structure directing agent and exhibiting at least one of the following:
  (a) an $^{29}$Si MAS spectrum having a plurality of chemical shifts of about 115.59 ppm, about 115.19 ppm, about 111.2 ppm, about 109.58 ppm, about 109.27 ppm, about 108.81 ppm, and about 106.73 ppm downfield of a peak corresponding to an external standard of tetramethylsilane; or
  (b) a powder XRD diffraction pattern-having at least five of the characteristic peaks at 7.43±0.15° 2-Theta, 8.26±0.15° 2-Theta, 9.62±0.15° 2-Theta, 10.08±0.15° 2-Theta, 10.48±0.15° 2-Theta, 14.83±0.15° 2-Theta, 18.42±0.15° 2-Theta, 22.96±0.15° 2-Theta, 23.55±0.15° 2-Theta, or 25.02±0.15° 2-Theta.

7. A calcined microporous silicate solid having a framework characterized by unit cell parameters:

| Chemical composition | [Si$_{20}$O$_{40}$] |
|---|---|
| Unit cell | |
| a (Å) | 13.0187 (1) |
| B (Å) | 11.2063 (1) |
| c (Å) | 9.3758 (1) |
| α (°) | 92.8224 (6) |
| β (°) | 107.2048 (5) |
| γ (°) | 103.2565 (5) |
| Space group | P-1 |
| R$_F$ | 0.041 |
| R$_{wp}$ | 0.077 |
| R$_{exp}$ | 0.068 |
| Selected bond distances (Å) and angles (°) | | | |
| Si—O (Å) | min: 1.59 | max: 1.62 | avg: 1.61 |
| O—Si—O (°) | min: 106.4 | max: 112.2 | avg: 109.5 |
| Si—O—Si (°) | min: 142.1 | max: 157.3 | avg: 148.9 |

8. The crystalline microporous solid of claim 1, where the crystalline microporous solid is a pure silicate, an aluminosilicate, or a titanosilicate.

9. The crystalline microporous solid of claim 6, wherein the solid exhibits an $^{29}$Si MAS spectrum having a plurality of chemical shifts of about 115.59 ppm, about 115.19 ppm, about 111.2 ppm, about 109.58 ppm, about 109.27 ppm, about 108.81 ppm, and about 106.73 ppm downfield of a peak corresponding to an external standard of tetramethylsilane.

10. The crystalline microporous solid of claim 6, wherein the solid exhibits a powder XRD diffraction pattern that is substantially the same as any one of those shown in FIG. 11, FIG. 12, FIG. 13A, or FIG. 13B.

11. The crystalline microporous solid of claim 6, wherein the solid exhibits a powder XRD pattern having at least five of the characteristic peaks at 7.43±0.15° 2-Theta, 8.26±0.15° 2-Theta, 9.62±0.15° 2-Theta, 10.08±0.15° 2-Theta, 10.48±0.15° 2-Theta, 14.83±0.15° 2-Theta, 18.42±0.15° 2-Theta, 22.96±0.15° 2-Theta, 23.55±0.15° 2-Theta, or 25.02±0.15° 2-Theta.

12. The crystalline microporous solid of claim 6, wherein the solid exhibits a powder XRD pattern having at least seven of the characteristic peaks at 7.43±0.15° 2-Theta, 8.26±0.15° 2-Theta, 9.62±0.15° 2-Theta, 10.08±0.15° 2-Theta, 10.48±0.15° 2-Theta, 14.83±0.15° 2-Theta, 18.42±0.15° 2-Theta, 22.96±0.15° 2-Theta, 23.55±0.15° 2-Theta, or 25.02±0.15° 2-Theta.

13. The crystalline microporous solid of claim 6, where the crystalline microporous solid is a silicate.

14. The crystalline microporous solid of claim 6, where the crystalline microporous solid is a pure silicate, an aluminosilicate, or a titanosilicate.

15. The crystalline microporous solid of claim 6, further comprising (b) aluminum oxide, boron oxide, gallium oxide, hafnium oxide, iron oxide, tin oxide, titanium oxide, indium oxide, vanadium oxide, zirconium oxide, or any combination thereof.

16. The crystalline microporous solid of claim 6, present as a crystalline microporous pure silicate solid, wherein the crystalline microporous silicate solid exhibits:

(a) an $^{29}$Si MAS spectrum having a plurality of chemical shifts of about 115.59 ppm, about 115.19 ppm, about 111.2 ppm, about 109.58 ppm, about 109.27 ppm, about 108.81 ppm, and about 106.73 ppm downfield of a peak corresponding to an external standard of tetramethylsilane.

17. The crystalline microporous solid of claim 6, present as a crystalline microporous silicate solid, wherein the crystalline microporous silicate solid exhibits exhibits a powder XRD diffraction pattern that is substantially the same as any one of those shown in FIG. 11, FIG. 12, FIG. FIG. 13A, or FIG. 13B.

18. The crystalline microporous solid of claim 6, present as a crystalline microporous silicate solid, wherein the crystalline microporous silicate solid exhibits a powder XRD pattern with at least five characteristic peaks at 7.43±0.15° 2-theta, 8.26±0.15° 2-theta, 9.62±0.15° 2-theta, 10.08±0.15° 2-theta, 10.48±0.15° 2-theta, 14.83±0.15° 2-theta, 18.42±0.15° 2-theta, 22.96±0.15° 2-theta, 23.55±0.15° 2-theta, or 25.02±0.15° 2-theta.

19. A process of preparing the crystalline microporous solid of CIT-7 topology of claim 1 comprising hydrothermally treating a composition comprising:
(a) (i) at least one source of a silicon oxide, germanium oxide, or combination thereof; and optionally
(ii) at least one source of aluminum oxide, boron oxide, gallium oxide, hafnium oxide, iron oxide, tin oxide, titanium oxide, indium oxide, vanadium oxide, zirconium oxide, or combination or mixture thereof; and
(b) a linked pair of quaternary imidazolium cations of a structure:

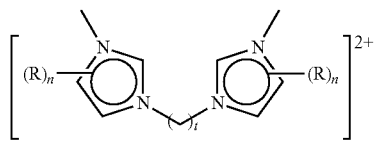

under conditions effective to crystallize the crystalline microporous solid of claim 1;
wherein t is 3, 4, 5, or 6; and
R is independently methyl or ethyl, and n is independently 1, 2, or 3;
said linked pair of quaternary imidazolium cations having associated fluoride or hydroxide ions.

20. The process of claim 19, wherein the composition being hydrothermally treated comprises either (i) at least one source of silicon oxide or (ii) at least one form of silicon oxide and at least one source of aluminum oxide, for the preparation of crystalline microporous silicate and aluminosilicate solids, respectively.

21. The process of claim 19, wherein the linked pair of quaternary imidazolium cations has a structure:

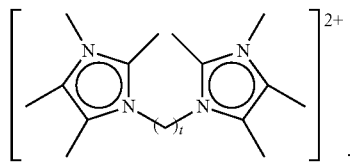

22. The process of claim 19, wherein the linked pair of quaternary imidazolium cations has a structure:

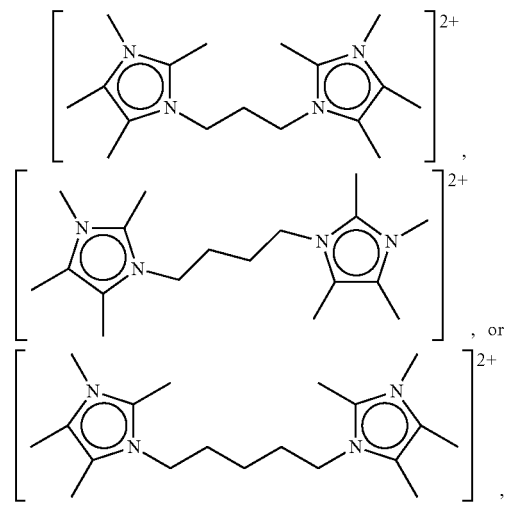

said linked pair of quaternary imidazolium cations having associated hydroxide ions.

23. The process of claim 19, wherein the conditions effective to crystallize the crystalline microporous solid of CIT-7 topology comprise hydrothermally treating a gel composition of the at least one source of a silicon oxide, the organic structure directing agent in its hydroxide form, aqueous HF, and water, the total water being present at a ratio of water:silicon dioxide of 4:1 to less than 7:1 at a temperature in a range of from 160° C. to 175° C. for a period of at least six days.

24. The process of claim 19, wherein the conditions effective to crystallize the crystalline microporous solid of CIT-7 topology comprise hydrothermally treating a gel composition of the at least one source of a silicon oxide, the at least one source of aluminum oxide, the ratio of Si:Al being in a range of from 15 to 250, the organic structure directing agent in its hydroxide form, aqueous HF, and water, the total water being present at a ratio of water:silicon dioxide of 4:1 to less than 7:1 at a temperature in a range of from 160° C. to 175° C. for a period of at least six days.

25. The process of claim 19, wherein the conditions effective to crystallize the crystalline microporous solid of CIT-7 topology comprise hydrothermally treating a gel composition of the at least one source of a silicon oxide, the at least one source of aluminum oxide, the ratio of Si:Al being in a range of from 5 to 300, the organic structure directing agent in its hydroxide form, sodium hydroxide, water, and seed crystals of CIT-topology at a temperature in a range of from 160° C. to 175° C. for a period of at least six days.

26. A process of preparing the crystalline microporous solid of CIT-7 topology of claim 1, comprising hydrothermally treating a composition comprising:
(a) (i) at least one source of silicon oxide and optionally
(ii) at least one source of aluminum oxide, boron oxide, gallium oxide, hafnium oxide, iron oxide, tin oxide, titanium oxide, indium oxide, vanadium oxide, zirconium oxide, or combination or mixture thereof, in the presence of an organic complex comprising
(b) an imidazolium cation comprising methyl and ethyl groups and having a C/N+ ratio in a range of from 6:1 to 10:1; and
(c) an associated hydroxide or fluoride anion;

under conditions effective to crystallize a crystalline microporous solid of claim 1, wherein the crystalline microporous solid is a crystalline microporous silicate solid.

27. The process of claim 26, comprising hydrothermally treating a composition comprising
(a) (i) at least one source of a silicon oxide, germanium oxide, or combination thereof;
(ii) at least one source of aluminum oxide; and optionally
(iii) at least one source of boron oxide, gallium oxide, hafnium oxide, iron oxide, tin oxide, titanium oxide, indium oxide, vanadium oxide, zirconium oxide, or combination or mixture thereof and
(b) an imidazolium cation comprising methyl and ethyl groups and having a C/N+ ratio in a range of from 6:1 to 8:1 and an associated hydroxide or fluoride anion, under conditions effective to crystallize a crystalline microporous aluminosilicate solid.

28. The process of claim 26, wherein the imidazolium cation is described by a resonance form that is:

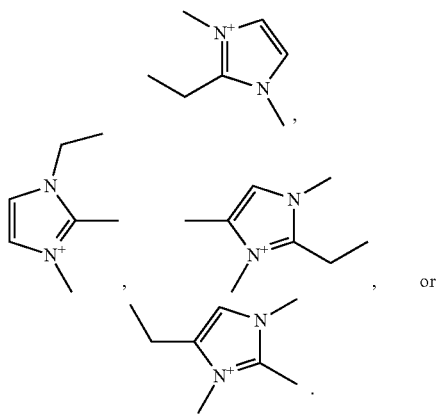

29. The process of claim 19 or 26, wherein the composition further comprises aqueous HF.

30. The process of claim 19 or 26, wherein the composition further comprises aqueous hydroxide.

31. The process of claim 19 or 26, wherein the hydrothermally treating is done at a temperature in a range of from about 100° C. to about 200° C. for a time effective for crystallizing the crystalline microporous solid of claim 1.

32. The process of claim 19 or 26, further comprising isolating the crystalline microporous solid of claim 1.

33. The process of claim 32, further comprising calcining the crystalline microporous solid of claim 1 at a temperature in a range of from about 350° C. to about 850° C. so as to produce a calcined crystalline microporous solid.

34. The process of claim 33, further comprising treating the calcined crystalline microporous solid with an aqueous ammonium salt.

35. The process of claim 33, further comprising treating at least some pores of the calcined crystalline microporous solid with at least one type of transition metal or transition metal oxide.

36. The process of claim 26, wherein the conditions effective to crystallize the crystalline microporous solid of CIT-7 topology comprise hydrothermally treating a gel composition of the at least one source of a silicon oxide, the organic structure directing agent in its hydroxide form, aqueous HF, and water, the total water being present at a ratio of water:silicon dioxide of 4:1 to less than 7:1 at a temperature in a range of from 160° C. to 175° C. for a period of at least six days.

37. The process of claim 26, wherein the conditions effective to crystallize the crystalline microporous solid of CIT-7 topology comprise hydrothermally treating a gel composition of the at least one source of a silicon oxide, the at least one source of aluminum oxide, the ratio of Si:Al being in a range of from 15 to 250, the organic structure directing agent in its hydroxide form, aqueous HF, and water, the total water being present at a ratio of water:silicon dioxide of 4:1 to less than 7:1 at a temperature in a range of from 160° C. to 175° C. for a period of at least six days.

38. The process of claim 26, wherein the conditions effective to crystallize the crystalline microporous solid of CIT-7 topology comprise hydrothermally treating a gel composition of the at least one source of a silicon oxide, the at least one source of aluminum oxide, the ratio of Si:Al being in a range of from 5 to 300, the organic structure directing agent in its hydroxide form, sodium hydroxide, water, and seed crystals of CIT-topology at a temperature in a range of from 160° C. to 175° C. for a period of at least six days.

39. A process for affecting an organic transformation, the process comprising:
(a) carbonylating dimethyl ether (DME) with CO at low temperatures;
(b) reducing NOx with methane;
(c) cracking or dehydrogenating;
(d) converting paraffins to aromatics;
(e) methanol to olefins (MTO) conversion;
(f) isomerizing xylenes;
(g) disproportionating toluene;
(h) alkylating aromatic hydrocarbons;
(i) oligomerizing alkenes;
(j) aminating lower alcohols;
(k) separating and sorbing lower alkanes;
(l) hydrocracking a hydrocarbon;
(m) dewaxing a hydrocarbon feedstock;
(n) isomerizing an olefin;
(o) producing a higher molecular weight hydrocarbon from lower molecular weight hydrocarbon;
(p) reforming a hydrocarbon;
(q) converting a lower alcohol or other oxygenated hydrocarbon to produce olefin products;
(r) reducing the content of an oxide of nitrogen contained in a gas stream in the presence of oxygen; or
(s) separating nitrogen from a nitrogen-containing gas mixture;

by contacting the respective feedstock with a catalyst comprising the crystalline microporous solid of claim 6, under conditions sufficient to affect the named organic transformation.

* * * * *